(12) United States Patent
Ledoussal et al.

(10) Patent No.: US 6,900,224 B2
(45) Date of Patent: May 31, 2005

(54) ANTIMICROBIAL QUINOLONES, THEIR COMPOSITIONS AND USES

(75) Inventors: Benoit Ledoussal, Mason, OH (US); Xiufeng Eric Hu, Cincinnati, OH (US); Ji-In Kim Almstead, Holmdel, NJ (US); Jeffrey Lyle Gray, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/462,554

(22) Filed: Jun. 16, 2003

(65) Prior Publication Data

US 2004/0038975 A1 Feb. 26, 2004

Related U.S. Application Data

(60) Provisional application No. 60/400,014, filed on Jul. 31, 2002.

(51) Int. Cl.[7] .................... A61K 31/47; C07D 401/02
(52) U.S. Cl. .................... 514/306; 514/312; 546/138; 546/153; 546/156
(58) Field of Search .................... 514/306, 312; 546/138, 153, 156

(56) References Cited

U.S. PATENT DOCUMENTS

| | | | |
|---|---|---|---|
| 6,235,751 B1 * | 5/2001 | Park | .......................... 514/306 |
| 6,329,391 B1 | 12/2001 | Ledoussal et al. | |
| 6,387,928 B1 | 5/2002 | Ledoussal et al. | |

FOREIGN PATENT DOCUMENTS

| | | |
|---|---|---|
| EP | 0 342 675 | 11/1989 |
| WO | WO 9510519 * | 4/1995 |
| WO | WO 9639407 * | 12/1996 |
| WO | WO 00/21952 A1 | 4/2000 |
| WO | WO 00/78748 A1 | 12/2000 |
| WO | WO 2001053273 * | 7/2001 |
| WO | WO 02/48138 A1 | 6/2002 |

OTHER PUBLICATIONS

Jaen–Oltra, J Med Chem, vol. 43, pp 1143–1148, 2000.*
Ma, J Med Chem, vol. 42, pp 4202–4213, 1999.*
Suto, M.J. et al., "Fluoroquinolones: Relationships between Structural Variations, Mammalian Cell Cytotoxicity, and Antimicrobial Activity", *J. Med. Chem.*, 1992, vol. 35, pp. 4745–4750.
Tabarrini, O. et al., 6–Hydroxy Derivative as New Desfluoroquinolone (DFQ): Synthesis and DNA– Binding Study, *Nucleosides, Nucleotides & Nucleic Acids*, 2000, pp. 1327–1336, vol. 19, No. 8, US.

* cited by examiner

*Primary Examiner*—Zinna Northington Davis
(74) *Attorney, Agent, or Firm*—Naishadh N. Desai; Andrew A. Paul; David V. Upite

(57) ABSTRACT

Compounds of the following formula:

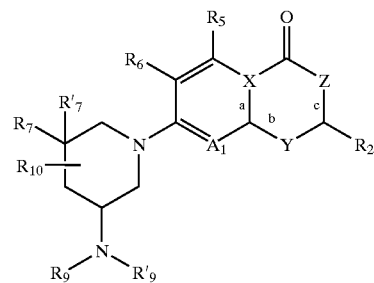

are effective antimicrobial agents.

39 Claims, No Drawings

ANTIMICROBIAL QUINOLONES, THEIR COMPOSITIONS AND USES

CROSS REFERENCE TO RELATED APPLICATION

This application claims priority under Title 35, United States Code 119(e) from Provisional Application Ser. No. 60/400,014 filed Jul. 31, 2002.

FIELD OF THE INVENTION

The subject invention relates to novel antimicrobial compounds, their compositions and their uses.

BACKGROUND

The chemical and medical literature describes compounds that are said to be antimicrobial, i.e., capable of destroying or suppressing the growth or reproduction of microorganisms, such as bacteria. For example, such antibacterials and other antimicrobials are described in *Antibiotics, Chemotherapeutics, and Antibacterial Agents for Disease Control* (M. Grayson, editor, 1982), and E. Gale et al., *The Molecular Basis of Antibiotic Action* 2d edition (1981).

The mechanism of action of these antibacterials vary. However, they are generally believed to function in one or more of the following ways: by inhibiting cell wall synthesis or repair; by altering cell wall permeability; by inhibiting protein synthesis; or by inhibiting synthesis of nucleic acids. For example, beta-lactam antibacterials act through inhibiting the essential penicillin binding proteins (PBPs) in bacteria, which are responsible for cell wall synthesis. As another example, quinolones act, at least in part, by inhibiting synthesis of DNA, thus preventing the cell from replicating.

The pharmacological characteristics of antimicrobials, and their suitability for any given clinical use, vary. For example, the classes of antimicrobials (and members within a class) may vary in 1) their relative efficacy against different types of microorganisms, 2) their susceptibility to development of microbial resistance and 3) their pharmacological characteristics, such as their bioavailability, and biodistribution. Accordingly, selection of an appropriate antibacterial (or other antimicrobial) in a given clinical situation requires analysis of many factors, including the type of organism involved, the desired method of administration, the location of the infection to be treated and other considerations.

However, many such attempts to produce improved antimicrobials yield equivocal results. Indeed, few antimicrobials are produced that are truly clinically-acceptable in terms of their spectrum of antimicrobial activity, avoidance of microbial resistance, and pharmacology. Thus there is a continuing need for broad spectrum antimicrobials, which are effective against resistant microbes.

Some 1,4-dihydroquinolone, naphthyridine or related heterocyclic moieties are known in the art to have antimicrobial activity and are described in the following references: R. Albrecht, *Prog. Drug Research*, Vol. 21, p. 9 (1977); J. Wolfson et al., "The Fluoroquinolones: Structures, Mechanisms of Action and Resistance, and Spectra of Activity In Vitro", *Antimicrob. Agents and Chemother.*, Vol. 28, p. 581 (1985); G. Klopman et al., *Antimicrob. Agents and Chemother.*, Vol. 31, p. 1831 (1987); M. P. Wentland et al., *Ann. Rep. Med. Chem.*, Vol. 20, p. 145 (1986); J. B. Cornett et al., *Ann. Rep. Med. Chem.*, Vol. 21, p. 139 (1986); P. B. Fernandes et al., *Ann. Rep. Med. Chem.*, Vol. 22, p. 117 (1987); A. Koga, et al., "Structure-Activity Relationships of Antibacterial 6,7- and 7,8-Disubstituted 1-alkyl-1,4-dihydro-4-oxoquinoline-3-carboxylic Acids", *J. Med. Chem.*, Vol. 23, pp. 1358–1363 (1980); J. M. Domagala et al., *J. Med. Chem.*, Vol. 31, p. 991 (1988); T. Rosen et al., *J. Med. Chem.*, Vol. 31, p. 1586 (1988); T. Rosen et al., *J. Med. Chem.*, Vol. 31, p. 1598 (1988); B. Ledoussal et al., "Non 6-Fluoro Substituted Quinolone Antibacterials: Structure and Activity", *J. Med Chem.*, Vol. 35, p. 198–200 (1992); J. M. Domagala et al., "Quinolone Antibacterials Containing the New 7-[3-(1-Aminoethyl)-1-pyrrolidinyl] Side Chain: The Effects of the 1-Aminoethyl Moiety and Its Stereochemical Configurations on Potency and in Vivo Efficacy", *J. Med. Chem.*, Vol. 36, pp. 871–882 (1993); Hagen et al., "Synthesis and Antibacterial Activity of New Quinolones Containing a 7-[3-(1-Amino-1-methylethyl)-1-pyrrolidinyl]Moiety. Gram Positive Agents with Excellent Oral Activity and Low Side-Effect Potential", *J. Med. Chem.* Vol. 37, pp. 733–738 (1994); V. Cecchetti et al., "Studies on 6-Aminoquinolines: Synthesis and Antibacterial Evaluation of 6-Amino-8-methylquinolones", *J. Med. Chem.*, Vol. 39, pp. 436–445 (1996); V. Cecchetti et al., "Potent 6-Desfluoro-8-methylquinolones as New Lead Compounds in Antibacterial Chemotherapy", *J. Med. Chem.*, Vol. 39, pp. 4952–4957 (1996); Hong et al., "Novel 5-Amino-6-methylquinolone Antibacterials: a New Class of Non-6-fluoroquinolones", *Bioorg. of Med. Chem. Let.*, Vol. 7, pp. 1875–1878 (1997); U.S. Pat. No. 4,844,902 to Grohe on Jul. 4, 1989; U.S. Pat. No. 5,072,001 to Hagen & Suto on Dec. 10, 1991; U.S. Pat. No. 5,328,908 to Demuth & White on Jul. 12, 1994; U.S. Pat. No. 5,457,104 to Bartel et al. on Oct. 10, 1995; U.S. Pat. No. 5,556,979 to Philipps et al. on Sep. 17, 1996; European Patent Appl. 572,259 of Ube Ind. pub. Dec. 1, 1993; European Patent Appl. 775,702 of Toyama Chem. Co. pub. May 28, 1997; Japanese Patent Pub. 62/255, 482 of Kyorin Pharm. Co. pub. Mar. 1, 1995.

Examples of bacterial infections resistant to antibiotic therapy have been reported in the past; they are now a significant threat to public health in the developed world. The development of microbial resistance (perhaps as a result of the intense use of antibacterials over extended periods of time) is of increasing concern in medical science. "Resistance" can be defined as existence of organisms, within a population of a given microbial species, that are less susceptible to the action of a given antimicrobial agent. This resistance is of particular concern in environments such as hospitals and nursing homes, where relatively high rates of infection and intense use of antibacterials are common. See, e.g., W. Sanders, Jr. et al., "Inducible Beta-lactamases: Clinical and Epidemiologic Implications for Use of Newer Cephalosporins", *Reviews of Infectious Diseases*, p. 830 (1988).

Pathogenic bacteria are known to acquire resistance via several distinct mechanisms including inactivation of the antibiotic by bacterial enzymes (e.g., b-lactamases hydrolyzing penicillin and cephalosporins); removal of the antibiotic using efflux pumps; modification of the target of the antibiotic via mutation and genetic recombination (e.g., penicillin-resistance in *Neiserria gonorrhoeae*); and acquisition of a readily transferable gene from an external source to create a resistant target (e.g., methicillin-resistance in *Staphylococcus aureus*). There are certain Gram positive pathogens, such as vancomycin-resistant *Enterococcus faecium*, which are resistant to virtually all commercially available antibiotics. Hence existing antibacterials have limited capacity in overcoming the threat of resistance.

In addition to overcoming resistance, many commercially available quinolone antibiotics exhibit undesirable side effects. For example, gatifloxacin ((±)-1-cyclopropyl-6-fluoro-1,4-dihydro-8-methoxy-7-(3-methyl-1-piperazinyl)-4-oxo-3-quinoline carboxylic acid) is reported to exhibit clastogenicity, *Journal of Antimicrobial Chemotherapy*, Vol. 33, pp. 685–706 (1994). Hence existing antibacterials have demonstrated undesirable side effects such as clastogenicity Thus it would be advantageous to provide antimicrobials with useful properties, including a favorable clastogenecity profile, which can be used against resistant microbes.

SUMMARY OF THE INVENTION

Applicants have found a novel series of quinolones and related compounds that are effective against resistant microbes, and provide significant activity advantages over the art including a favorable clastogenecity profile. In particular, the invention relates to compounds having a structure according to Formula (I)

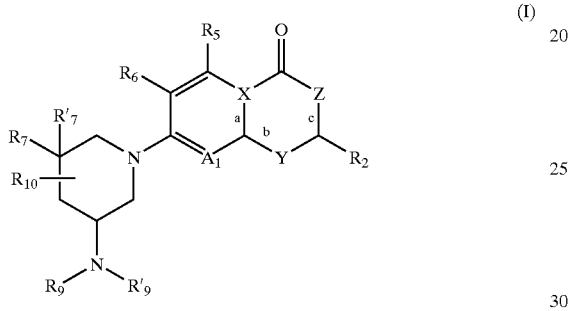

(I)

wherein:
(A)(1) $A^1$ is selected from —N— and —C($R^8$)—, where $R^8$ is selected from hydrogen, halo, $C_1$ to about $C_6$ alkyl, $C_2$ to about $C_6$ alkene or alkyne and $C_1$ to about $C_6$ alkoxy, all such alkyl, alkene, alkyne and alkoxy moieties being unsubstituted or substituted with from 1 to about 3 fluoro;
(2) a, b and c are each independently a single or double bond;
(3) (a) X is either from —C— or —N—; where (i) if X is —C—, a is a double bond and b is a single bond, and (ii) if X is —N—, a is a single bond and b is a double bond;
  (b) Y is selected from —N($R^1$)— and —C$R°R^1$—; wherein R° is selected from hydrogen and nil, wherein R° is hydrogen when b is single bond and R° is nil when b is a double bond;
  (c) Z is selected from —C(COR$^3$)—, —N($R^3$)— and —N(NHR$^3$)—; where (i) if Z is —C(COR$^3$)—, c is a double bond, and (ii) if Z is either —N($R^3$)— and —N(NHR$^3$)—, c is a single bond;
  (d) provided that Y is —N($R^1$)— only if X is —C—;
  (e) provided that Y is —C($R^1$)— only if X is —N— and Z is —C(COR$^3$)—;
  (f) provided that Z is either —N(OH)— or —N(NHR$^3$)— only if X is —C—, Y is —N($R^1$)— and $A^1$ is —C($R^8$)—;
(4) $R^1$ is selected from $C_3$ to about $C_6$ cycloalkyl, $C_3$ to about $C_6$ heterocycloalkyl, $C_1$ to about $C_6$ alkyl, $C_2$ to about $C_6$ alkene or alkyne, $C_1$ to about $C_6$ alkyloxy, 6-membered aryl and 6-membered heteroaryl, all such alkyl, alkene, alkyne, alkoxy, cycloalkyl, aryl and heteroaryl being unsubstituted or substituted with from 1 to 3 fluoro, all such aryl and heteroaryl also being unsubstituted or substituted with one hydroxy in the 4-position;

(5) $R^2$ is selected from hydrogen, double bond oxygen, $C_1$ to about $C_6$ alkyl, $C_2$ to about $C_6$ alkene or alkyne, $C_1$ to about $C_6$ alkoxy and $C_1$ to about $C_6$ thioalkyl; provided that $R^2$ is double bond oxygen only if Z is either —N(OH)— or —N(NHR$^3$)—;
(6) $R^3$ is selected from hydrogen, hydroxy, $C_1$ to about $C_6$ alkyl, $C_2$ to about $C_6$ alkene or alkyne, $C_1$ to about $C_6$ alkoxy and $C_1$ to about $C_6$ thioalkyl;
(7) $R^5$ is selected from hydrogen, hydroxy, amino, halo, $C_1$ to about $C_6$ alkyl, $C_2$ to about $C_4$ alkene or alkyne and $C_1$ to about $C_4$ alkoxy, all such alkyl, alkene, alkyne and alkoxy moieties being unsubstituted or substituted with from 1 to 3 fluoro;
(8) $R^6$ is selected from hydroxy, aminocarbonyl, fluoro, chloro, bromo, cyano, $C_1$ to about $C_2$ alkyl and $C_2$ to about $C_4$ alkenyl or alkynyl, all such alkyl, alkenyl and alkynyl moieties being unsubstituted or substituted with from 1 to about 3 fluoro;
(9) $R^7$ and $R^{7'}$ are each independently selected from:
  (a) hydrogen, $C_1$ to about $C_6$ alkyl, $C_2$ to about $C_6$ alkene or alkyne, $C_1$ to about $C_6$ alkoxy, $C_1$ to about $C_6$ alkylthio and $C_1$ to about $C_6$ heteroalkyl; provided $R^7$ and $R^{7'}$ are not both hydrogen;
  (b) or $R^7$ and $R^{7'}$ join to form a $C_3$ to about $C_6$ cycloalkyl or heterocyclic ring containing the carbon atom to which they are bonded;
  (c) all such alkyl, alkene, alkyne, alkoxy, alkythio, heteroalkyl, cycloalkyl and heterocyclic moieties being unsubstituted or substituted with from 1 to 3 fluoro;
(10) $R^9$ and $R^{9'}$ are each independently selected from hydrogen and $C_1$ to about $C_3$ alkyl, or $R^9$ and $R^{9'}$ join to form a $C_3$ to about $C_6$ heterocyclic ring containing the nitrogen atom to which they are bonded; and
(11) $R^{10}$ represents the moieties on the piperidine ring other than $R^7$, $R^{7'}$ and —NR$^9$R$^{9'}$, where each $R^{10}$ is independently selected from hydrogen, $C_1$ to about $C_6$ alkyl, $C_2$ to about $C_6$ alkene or alkyne, $C_1$ to about $C_6$ alkoxy and $C_3$–$C_6$ cycloalkyl all such alkyl, alkene, alkyne, alkoxy and cycloalkyl moieties being unsubstituted or substituted with from 1 to 3 fluoro;
or
(B) if $A^1$ is —C($R^8$)—, X is —C— and Y is —N($R^1$)—, then $R^8$ and $R^1$ can join to form a 6-membered heterocyclic ring, where $R^2$, $R^3$, $R^5$, $R^6$, $R^7$, $R^{7'}$, $R^9$, $R^{9'}$ and $R^{10}$ are as described in (A); or
(C) if $A^1$ is —C($R^8$)—, X is —C—, Y is —N($R^1$)—, and Z is —C(COR$^3$) then $R^1$ and $R^2$ can join to form a monocyclic or bicyclic heterocyclic ring, where $R^3$, $R^5$, $R^6$, $R^7$, $R^{7'}$, $R^8$, $R^9$, $R^{9'}$ and $R^{10}$ are as described in (A); or
(D) if $A^1$ is —C($R^8$)—, X is —C—, Y is —N($R^1$)— and Z is —C(COR$^3$), then $R^2$ and $R^3$ can join to form a 5-membered heterocycloalkyl that is substituted with a carbonyl moiety, where $R^1$, $R^5$, $R^6$, $R^7$, $R^{7'}$, $R^8$, $R^9$, $R^{9'}$ and $R^{10}$ are as described in (A);

or an optical isomer, diastereomer or enantiomer thereof; a pharmaceutically-acceptable salt, hydrate, or biohydrolyzable ester, amide or imide thereof. In addition, compounds incorporating the compounds of the invention, or using compounds of the invention as starting materials are also contemplated in this invention.

It has been found that the compounds of this invention, and compositions containing these compounds, are effective antimicrobial agents against a broad range of pathogenic microorganisms with advantages in low susceptibility to microbial resistance, reduced toxicity, and improved pharmacology.

It has been also found that the compounds of this invention, and compositions containing these compounds, exhibit a favorable clastogenecity profile.

DESCRIPTION OF THE INVENTION

I. Terms and Definitions:

The following is a list of definitions for terms used herein:

"Acyl" is a radical formed by removal of the hydroxy from a carboxylic acid (i.e., R—C(=O)—). Preferred acyl groups include (for example) acetyl, formyl, and propionyl.

"Alkyl" is a saturated hydrocarbon chain having 1 to 15 carbon atoms, preferably 1 to 10, more preferably 1 to 4 carbon atoms. "Alkene" is a hydrocarbon chain having at least one (preferably only one) carbon-carbon double bond and having 2 to 15 carbon atoms, preferably 2 to 10, more preferably 2 to 4 carbon atoms. "Alkyne" is a hydrocarbon chain having at least one (preferably only one) carbon-carbon triple bond and having 2 to 15 carbon atoms, preferably 2 to 10, more preferably 2 to 4 carbon atoms. Alkyl, alkene and alkyne chains (referred to collectively as "hydrocarbon chains") may be straight or branched and may be unsubstituted or substituted. Preferred branched alkyl, alkene and alkyne chains have one or two branches, preferably one branch. Preferred chains are alkyl. Alkyl, alkene and alkyne hydrocarbon chains each may be unsubstituted or substituted with from 1 to 4 substituents; when substituted, preferred chains are mono-, di-, or tri-substituted. Alkyl, alkene and alkyne hydrocarbon chains each may be substituted with halo, hydroxy, aryloxy (e.g., phenoxy), heteroaryloxy, acyloxy (e.g., acetoxy), carboxy, aryl (e.g., phenyl), heteroaryl, cycloalkyl, heterocycloalkyl, spirocycle, amino, amido, acylamino, keto, thioketo, cyano, or any combination thereof. Preferred hydrocarbon groups include methyl, ethyl, propyl, isopropyl, butyl, vinyl, allyl, butenyl, and exomethylenyl.

"Alkoxy" is an oxygen radical having a hydrocarbon chain substituent, where the hydrocarbon chain is an alkyl or alkenyl (i.e., —O-alkyl or —O-alkenyl). Preferred alkoxy groups include (for example) methoxy, ethoxy, propoxy and allyloxy.

"Alkylthio" is —S-alkyl (e.g. —S—CH$_3$).

Also, as referred to herein, a "lower" alkoxy, alkylthio, alkyl, alkene or alkyne moiety (e.g., "lower alkyl") is a chain comprised of 1 to 6, preferably from 1 to 4, carbon atoms in the case of alkyl, alkoxy and alkylthio, and 2 to 6, preferably 2 to 4, carbon atoms in the case of alkene and alkyne.

"Amino" refers to a primary (—NH$_2$), secondary (—NH(alkyl), also referred to herein as "alkylamino") or tertiary (—N(alkyl)$_2$, also referred to herein as "dialkylamino").

"Aminoalkyl" is an alkyl moiety substituted with an amino, alkyl amino or dialkyl amino group (e.g., —CH$_2$NH$_2$, —CH$_2$CH$_2$NH$_2$, —CH$_2$NHCH$_3$, —CH$_2$N(CH$_3$)$_2$).

"Aryl" is an aromatic hydrocarbon ring. Aryl rings are monocyclic or fused bicyclic ring systems. Monocyclic aryl rings contain 6 carbon atoms in the ring. Monocyclic aryl rings are also referred to as phenyl rings. Bicyclic aryl rings contain from 8 to 17 carbon atoms, preferably 9 to 12 carbon atoms, in the ring. Bicyclic aryl rings include ring systems wherein one ring is aryl and the other ring is aryl, cycloalkyl, or heterocycloakyl. Preferred bicyclic aryl rings comprise 5-, 6- or 7-membered rings fused to 5-, 6-, or 7-membered rings. Aryl rings may be unsubstituted or substituted with from 1 to 4 substituents on the ring. Aryl may be substituted with halo, cyano, nitro, hydroxy, carboxy, amino, acylamino, alkyl, heteroalkyl, haloalkyl, phenyl, aryloxy, alkoxy, heteroalkyloxy, carbamyl, haloalkyl, methylenedioxy, heteroaryloxy, or any combination thereof. Preferred aryl rings include naphthyl, tolyl, xylyl, and phenyl. The most preferred aryl ring radical is phenyl.

"Aryloxy" is an oxygen radical having an aryl substituent (i.e., —O-aryl). Preferred aryloxy groups include (for example) phenoxy, napthyloxy, methoxyphenoxy, and methylenedioxyphenoxy.

"Carbocyclic ring" encompasses both cycloalkyl and aryl moieties, as those terms are defined herein.

"Carbonyl" is —C(=O)—.

"Cycloalkyl" is a saturated or unsaturated hydrocarbon ring. Cycloalkyl rings are not aromatic. Cycloalkyl rings are monocyclic, or are fused, spiro, or bridged bicyclic ring systems. Monocyclic cycloalkyl rings contain from about 3 to about 9 carbon atoms, preferably from 3 to 7 carbon atoms, in the ring. Bicyclic cycloalkyl rings contain from 7 to 17 carbon atoms, preferably from 7 to 12 carbon atoms, in the ring. Preferred bicyclic cycloalkyl rings comprise 4-, 5-, 6- or 7-membered rings fused to 5-, 6-, or 7-membered rings. Cycloalkyl rings may be unsubstituted or substituted with from 1 to 4 substituents on the ring. Cycloalkyl may be substituted with halo, cyano, alkyl, heteroalkyl, haloalkyl, phenyl, keto, hydroxy, carboxy, amino, acylamino, aryloxy, heteroaryloxy, or any combination thereof. Preferred cycloalkyl rings include cyclopropyl, cyclopentyl, and cyclohexyl.

"Halo" or "halogen" is fluoro, chloro, bromo or iodo. Preferred halo are fluoro, chloro and bromo; more preferred typically are chloro and fluoro, especially fluoro.

"Haloalkyl" is a straight, branched, or cyclic hydrocarbon substituted with one or more halo substituents. Preferred are C$_1$–C$_{12}$ haloalkyls; more preferred are C$_1$–C$_6$ haloalkyls; still more preferred still are C$_1$–C$_3$ haloalkyls. Preferred halo substituents are fluoro and chloro. The most preferred haloalkyl is trifluoromethyl.

"Heteroatom" is a nitrogen, sulfur, or oxygen atom. Groups containing more than one heteroatom may contain different heteroatoms.

"Heteroalkyl" is a saturated or unsaturated chain containing carbon and at least one heteroatom, wherein no two heteroatoms are adjacent. Heteroalkyl chains contain from 2 to 15 member atoms (carbon and heteroatoms) in the chain, preferably 2 to 10, more preferably 2 to 5. For example, alkoxy (i.e., —O-alkyl or —O-heteroalkyl) radicals are included in heteroalkyl. Heteroalkyl chains may be straight or branched. Preferred branched heteroalkyl have one or two branches, preferably one branch. Preferred heteroalkyl are saturated. Unsaturated heteroalkyl have one or more carbon-carbon double bonds and/or one or more carbon-carbon triple bonds. Preferred unsaturated heteroalkyls have one or two double bonds or one triple bond, more preferably one double bond. Heteroalkyl chains may be unsubstituted or substituted with from 1 to 4 substituents. Preferred substituted heteroalkyl are mono-, di-, or tri-substituted. Heteroalkyl may be substituted with lower alkyl, haloalkyl, halo, hydroxy, aryloxy, heteroaryloxy, acyloxy, carboxy, monocyclic aryl, heteroaryl, cycloalkyl, heterocycloalkyl, spirocycle, amino, acylamino, amido, keto, thioketo, cyano, or any combination thereof.

"Heteroaryl" is an aromatic ring containing carbon atoms and from 1 to about 6 heteroatoms in the ring. Heteroaryl rings are monocyclic or fused bicyclic ring systems. Monocyclic heteroaryl rings contain from about 5 to about 9 member atoms (carbon and heteroatoms), preferably 5 or 6 member atoms, in the ring. Bicyclic heteroaryl rings contain from 8 to 17 member atoms, preferably 8 to 12 member atoms, in the ring. Bicyclic heteroaryl rings include ring systems wherein one ring is heteroaryl and the other ring is aryl, heteroaryl, cycloalkyl, or heterocycloalkyl. Preferred bicyclic heteroaryl ring systems comprise 5-, 6- or 7-membered rings fused to 5-, 6-, or 7-membered rings. Heteroaryl rings may be unsubstituted or substituted with from 1 to 4 substituents on the ring. Heteroaryl may be substituted with halo, cyano, nitro, hydroxy, carboxy, amino, acylamino, alkyl, heteroalkyl, haloalkyl, phenyl, alkoxy, aryloxy, heteroaryloxy, or any combination thereof. Preferred heteroaryl rings include, but are not limited to, the following:

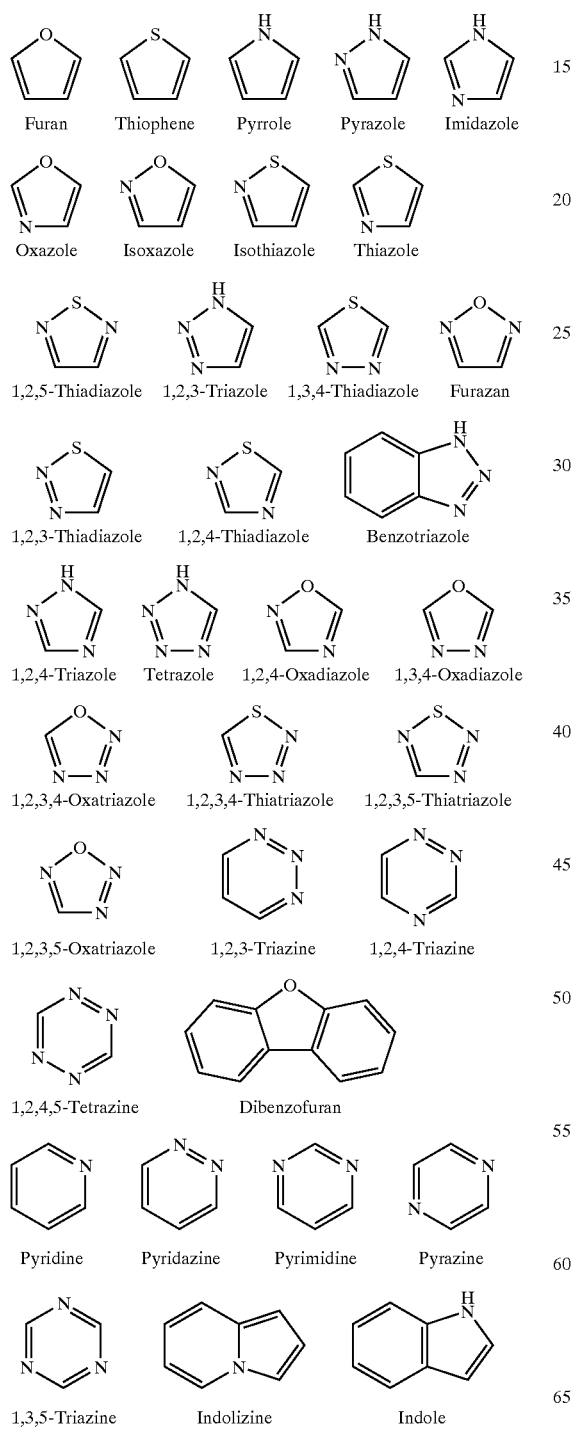

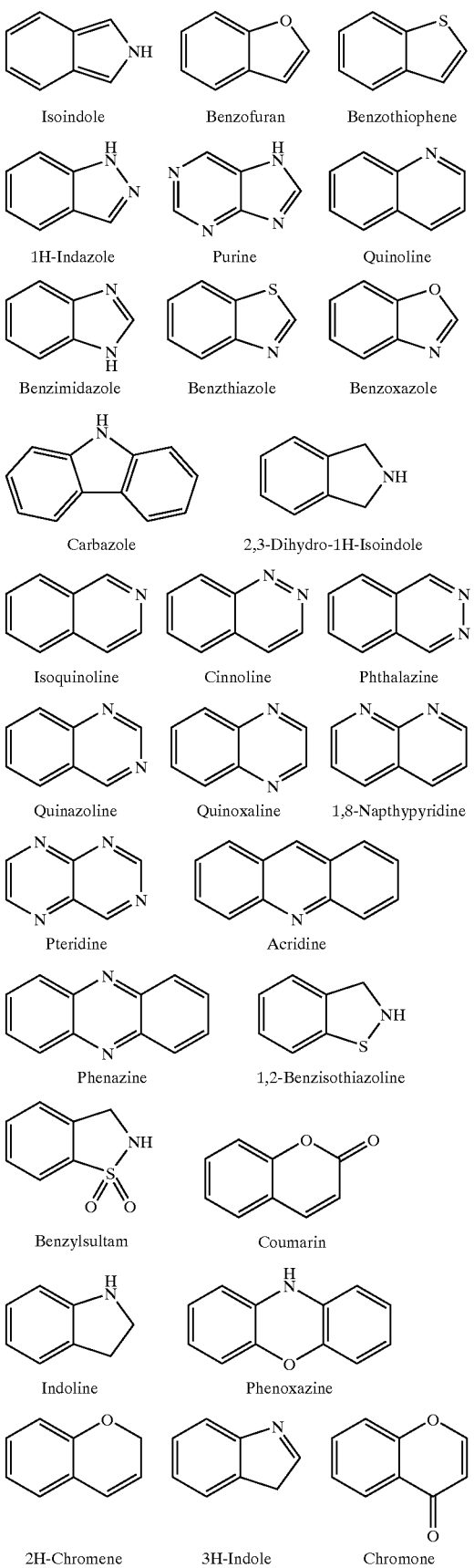

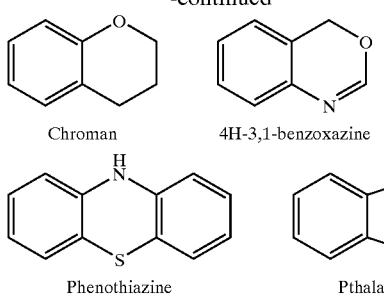

Chroman  4H-3,1-benzoxazine

Phenothiazine  Pthalan

"Heteroaryloxy" is an oxygen radical having a heteroaryl substituent (i.e., —O-heteroaryl). Preferred heteroaryloxy groups include (for example) pyridyloxy, furanyloxy, (thiophene)oxy, (oxazole)oxy, (thiazole)oxy, (isoxazole)oxy, pyrmidinyloxy, pyrazinyloxy, and benzothiazolyloxy.

"Heterocycloalkyl" is a saturated or unsaturated ring containing carbon atoms and from 1 to about 4 (preferably 1 to 3) heteroatoms in the ring. Heterocycloalkyl rings are not aromatic. Heterocycloalkyl rings are monocyclic or bicyclic ring systems. Monocyclic heterocycloalkyl rings contain from about 3 to about 9 member atoms (carbon and heteroatoms), preferably from 5 to 7 member atoms, in the ring. Bicyclic heterocycloalkyl rings contain from 7 to 17 member atoms, preferably 7 to 12 member atoms, in the ring. Bicyclic heterocycloalkyl rings contain from about 7 to about 17 ring atoms, preferably from 7 to 12 ring atoms. Bicyclic heterocycloalkyl rings may be fused, spiro, or bridged ring systems. Preferred bicyclic heterocycloalkyl rings comprise 5-, 6- or 7-membered rings fused to 5-, 6-, or 7-membered rings. Heterocycloalkyl rings may be unsubstituted or substituted with from 1 to 4 substituents on the ring. Heterocycloalkyl may be substituted with halo, cyano, hydroxy, carboxy, keto, thioketo, amino, acylamino, acyl, amido, alkyl, heteroalkyl, haloalkyl, phenyl, alkoxy, aryloxy or any combination thereof. Preferred substituents on heterocycloalkyl include halo and haloalkyl. Preferred heterocycloalkyl rings include, but are not limited to, the following:

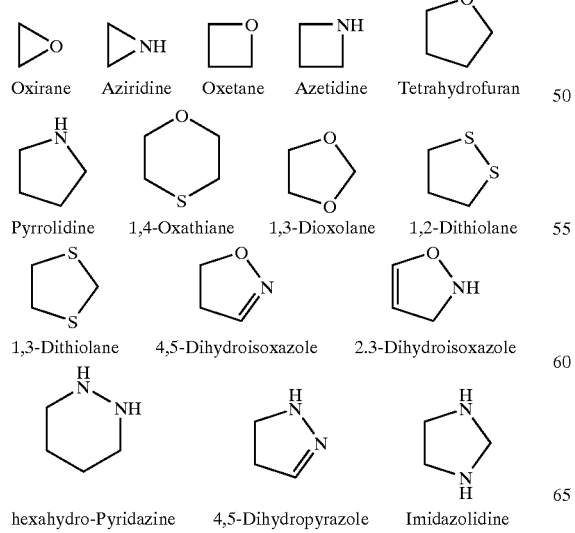

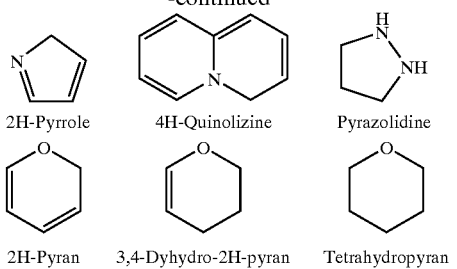

2H-Pyrrole  4H-Quinolizine  Pyrazolidine

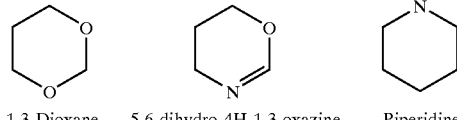

2H-Pyran  3,4-Dyhydro-2H-pyran  Tetrahydropyran

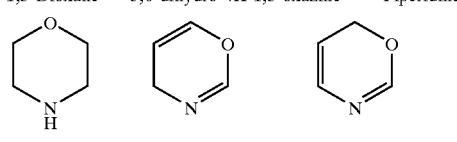

1,3-Dioxane  5,6-dihydro-4H-1,3-oxazine  Piperidine

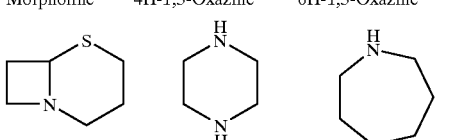

Morpholine  4H-1,3-Oxazine  6H-1,3-Oxazine

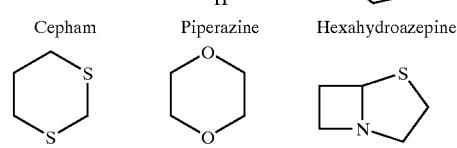

Cepham  Piperazine  Hexahydroazepine

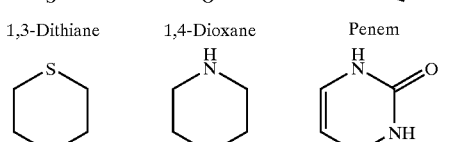

1,3-Dithiane  1,4-Dioxane  Penem

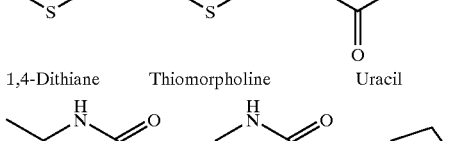

1,4-Dithiane  Thiomorpholine  Uracil

Thymine  Cytosine  Thiolane

"Heterocyclic ring" encompasses both hetercycloalkyl and heteroaryl moieties, as those terms are defined herein.

"Spirocycle" is an alkyl or heteroalkyl diradical substituent of alkyl or heteroalkyl wherein said diradical substituent is attached geminally and wherein said diradical substituent forms a ring, said ring containing 4 to 8 member atoms (carbon or heteroatom), preferably 5 or 6 member atoms.

"Lower" alkoxy, alkylthio, alkyl, alkene or alkyne moiety (e.g., "lower alkyl") is a chain comprised of 1 to 6, preferably from 1 to 4, carbon atoms in the case of alkyl, alkoxy and alkylthio, and 2 to 6, preferably 2 to 4, carbon atoms in the case of alkene and alkyne.

While alkyl, heteroalkyl, cycloalkyl, and heterocycloalkyl groups may be substituted with hydroxy, amino, and amido groups as stated above, the following are not envisioned in the invention:

1. Enols (OH attached to an alkene carbon).
2. Amino groups attached to a carbon bearing a double bond (except for vinylogous amides).
3. More than one hydroxy, amino, or amido attached to a single carbon (except where two nitrogen atoms are attached to a single carbon atom and all three atoms are member atoms within a heterocycloalkyl ring).
4. Hydroxy, amino, or amido attached to a carbon that also has a heteroatom attached to it.
5. Hydroxy, amino, or amido attached to a carbon that also has a halogen attached to it.

A "pharmaceutically-acceptable salt" is a cationic salt formed at any acidic (e.g., carboxyl) group, or an anionic salt formed at any basic (e.g., amino, alkylamino, dialkylamino, morphylino, and the like) group on the compound of the invention. Since many of the compounds of the invention are zwitterionic, either salt is possible and acceptable. Many such salts are known in the art. Preferred cationic salts include the alkali metal salts (such as sodium and potassium), alkaline earth metal salts (such as magnesium and calcium) and organic salts, such as ammonio. Preferred anionic salts include halides, sulfonates, carboxylates, phosphates, and the like. Clearly contemplated in such salts are addition salts that may provide an optical center, where once there is none. For example, a chiral tartrate salt may be prepared from the compounds of the invention, and this definition includes such chiral salts. Salts contemplated are nontoxic in the amounts administered to the patient-animal, mammal or human.

The compounds of the invention are sufficiently basic to form acid-addition salts. The compounds are useful both in the free-base form and the form of acid-addition salts, and both forms are within the purview of the invention. The acid-addition salts are in some cases a more convenient form for use. In practice, the use of the salt form inherently amounts to the use of the base form of the active. Acids used to prepare acid-addition salts include preferably those which produce, when combined with the free base, medicinally acceptable salts. These salts have anions that are relatively innocuous to the animal organism, such as a mammal, in medicinal doses of the salts so that the beneficial property inherent in the free base are not vitiated by any side effects ascribable to the acid's anions.

Examples of appropriate acid-addition salts include, but are not limited to hydrochloride, hydrobromide, hydroiodide, sulfate, hydrogensulfate, acetate, trifluoroacetate, nitrate, citrate, fumarate, formate, stearate, succinate, maleate, malonate, adipate, glutarate, lactate, propionate, butyrate, tartrate, methanesulfonate, trifluoromethanesulfonate, p-toluenesulfonate, dodecyl sulfate, cyclohexanesulfamate, and the like. However, other appropriate medicinally acceptable salts within the scope of the invention are those derived from other mineral acids and organic acids. The acid-addition salts of the basic compounds are prepared by several methods. For example, the free base can be dissolved in an aqueous alcohol solution containing the appropriate acid and the salt is isolated by evaporation of the solution. Alternatively, they may be prepared by reacting the free base with an acid in an organic solvent so that the salt separates directly. Where separation of the salt is difficult, it can be precipitated with a second organic solvent, or can be obtained by concentration of the solution.

Although medicinally acceptable salts of the basic compounds are preferred, all acid-addition salts are within the scope of the present invention. All acid-addition salts are useful as sources of the free base form, even if the particular salt per se is desired only as an intermediate product. For example, when the salt is formed only for purposes of purification or identification, or when it is used as an intermediate in preparing a medicinally acceptable salt by ion exchange procedures, these salts are clearly contemplated to be a part of this invention.

Such salts are well understood by the skilled artisan, and the skilled artisan is able to prepare any number of salts given the knowledge in the art. Furthermore, it is recognized that the skilled artisan may prefer one salt over another for reasons of solubility, stability, formulation ease and the like. Determination and optimization of such salts is within the purview of the skilled artisan's practice.

"Host" is a substrate capable of sustaining a microbe, preferably it is a living organism, more preferably an animal, more preferably a mammal, more preferably still a human.

"Biohydrolyzable amides" are aminoacyl, acylamino, or other amides of the compounds of the invention, where the amide does not essentially interfere, preferably does not interfere, with the activity of the compound, or where the amide is readily converted in vivo by a host to yield an active compound.

"Biohydrolyzable imides" are imides of compounds of the invention, where the imide does not essentially interfere, preferably does not interfere, with the activity of the compound, or where the imide is readily converted in vivo by a host to yield an active compound. Preferred imides are hydroxyimides.

"Biohydrolyzable esters" are esters of compounds of the invention, where the ester does not essentially interfere, preferably does not interfere, with the antimicrobial activity of the compound, or where the ester is readily converted in a host to yield an active compound. Many such esters are known in the art, as described in U.S. Pat. No. 4,783,443, issued to Johnston and Mobashery on Nov. 8, 1988 (incorporated by reference herein). Such esters include lower alkyl esters, lower acyloxy-alkyl esters (such as acetoxymethyl, acetoxyethyl, aminocarbonyloxymethyl, pivaloyloxymethyl and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters and alkylacylaminoalkyl esters (such as acetamidomethyl esters).

The illustration of specific protected forms and other derivatives of the Formula I compounds is not intended to be limiting. The application of other useful protecting groups, salt forms, etc. is within the ability of the skilled artisan.

A "solvate" is a complex formed by the combination of a solute (e.g., a quinolone) and a solvent (e.g., water). See J. Honig et al., *The Van Nostrand Chemist's Dictionary*, p. 650 (1953). Pharmaceutically-acceptable solvents used according to this invention include those that do not interfere with the biological activity of the quinolone or quinolone derivative (e.g., water, ethanol, acetic acid, N,N-dimethylformamide and others known or readily determined by the skilled artisan).

The terms "optical isomer", "stereoisomer", and "diastereomer" have the standard art recognized meanings (see, e.g., *Hawley's Condensed Chemical Dictionary*, 11th Ed.). The illustration of specific protected forms and other derivatives of the compounds of the instant invention is not intended to be limiting. The application of other useful protecting groups, salt forms, etc. is within the ability of the skilled artisan.

The compounds of the invention may have one or more chiral centers. As a result, one may selectively prepare one optical isomer, including diastereomer and enantiomer, over another, for example by use of chiral starting materials, catalysts or solvents, one may prepare both stereoisomers or both optical isomers, including diastereomers and enantiomers at once (a racemic mixture). Since the compounds of the invention may exist as racemic mixtures, mixtures of optical isomers, including diastereomers and enantiomers, or stereoisomers, they may be separated using known methods, such as chiral resolution, chiral chromatography and the like.

In addition, it is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

As used herein, a quinolone derivative includes prodrugs of a quinolone, or an active drug made from a quinolone. Preferably, such derivatives include lactams (e.g., cephems, carbacephems, penems, monolactams, etc.) covalently linked to the quinolone optionally via a spacer. Such derivatives and methods to make and use them are apparent to the skilled artisan, given the teachings of this specification.

II. Compounds:

The subject invention involves compounds of Formula (I):

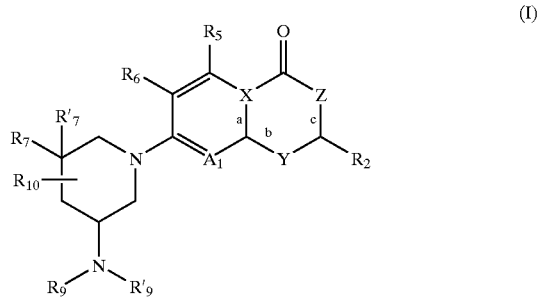

(I)

wherein $A^1$, X, Y, Z, a, b, c, $R^2$, $R^5$, $R^6$, $R^7$, $R^{7'}$, $R^9$, $R^{9'}$ and $R^{10}$ are as defined in the Summary of the Invention section above.

With reference to Formula (I), the description above indicates that in one embodiment (defined in sub-part (A)), the nucleus of the compounds will include only two fused rings as depicted. Alternatively, the nucleus of the compounds will include three or four fused rings, as defined in sub-parts (B) through (D). These alternative embodiments are depicted as Formula (D), Formula (E) and Formula (F), Formula (G), and Formula (H) respectively, below.

With respect to each of the embodiments described, a non-limiting list of preferred compounds is also set forth in tabular form. It will be recognized that for purification, administration and the like, salts and other derivatives of the above compounds are often used. Thus, a pharmaceutically-acceptable salt, hydrate, or biohydrolyzable ester, amide or imide thereof is contemplated as part of the subject invention and is meant to be included in the tables.

Table I contains a non-limiting list of compounds of Formula (A)

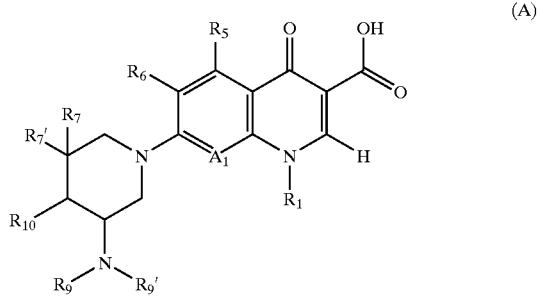

(A)

These compounds are those of Formula (I) where X is a carbon atom, Z is $—C(COR^3)—$, $R^2$ is hydrogen, $R^3$ is hydroxy, a represents a double bond, b represents a single bond, c is a double bond, Y is $N(R^1)$, and no additional fused rings are formed (i.e., compounds of sub-part (A)).

For purposes herein, Cy=Cyclopropyl; F-Cy=2-fluorocyclopropyl; 4F-Ph=4-fluorophenyl; 2,4diFPh=2,4-difluorophenyl.

TABLE I

| A1 | R1 | R5 | R6 | R7 | R'7 | R10 | R9 | R'9 |
|---|---|---|---|---|---|---|---|---|
| N | Cy | H | F | Me | H | H | H | H |
| C—H | Cy | H | F | Me | H | H | H | H |
| CF | Cy | H | F | Me | H | H | H | H |
| C—Cl | Cy | H | F | Me | H | H | H | H |
| C—Ome | Cy | H | F | Me | H | H | H | H |
| C—Me | Cy | H | F | Me | H | H | H | H |
| N | F—Cy | H | F | Me | H | H | H | H |
| C—H | F—Cy | H | F | Me | H | H | H | H |
| CF | F—Cy | H | F | Me | H | H | H | H |
| C—Cl | F—Cy | H | F | Me | H | H | H | H |
| C—Ome | F—Cy | H | F | Me | H | H | H | H |
| C—Me | F—Cy | H | F | Me | H | H | H | H |
| N | Et | H | F | Me | H | H | H | H |
| CH | Et | H | F | Me | H | H | H | H |
| CF | Et | H | F | Me | H | H | H | H |
| C—Cl | Et | H | F | Me | H | H | H | H |
| C—Ome | Et | H | F | Me | H | H | H | H |
| C—Me | Et | H | F | Me | H | H | H | H |
| N | tBu | H | F | Me | H | H | H | H |
| CH | tBu | H | F | Me | H | H | H | H |
| N | 4F—Ph | H | F | Me | H | H | H | H |
| CH | 4F—Ph | H | F | Me | H | H | H | H |
| CF | 4F—Ph | H | F | Me | H | H | H | H |
| C—Cl | 4F—Ph | H | F | Me | H | H | H | H |
| N | 2,4diFPh | H | F | Me | H | H | H | H |
| CH | 2,4diFPh | H | F | Me | H | H | H | H |
| CF | 2,4diFPh | H | F | Me | H | H | H | H |
| C—Cl | 2,4diFPh | H | F | Me | H | H | H | H |
| N | Cy | NH2 | F | Me | H | H | H | H |
| C—H | Cy | NH2 | F | Me | H | H | H | H |
| CF | Cy | NH2 | F | Me | H | H | H | H |
| C—Cl | Cy | NH2 | F | Me | H | H | H | H |
| C—Ome | Cy | NH2 | F | Me | H | H | H | H |
| C—Me | Cy | NH2 | F | Me | H | H | H | H |
| N | F—Cy | NH2 | F | Me | H | H | H | H |
| C—H | F—Cy | NH2 | F | Me | H | H | H | H |
| CF | F—Cy | NH2 | F | Me | H | H | H | H |
| C—Cl | F—Cy | NH2 | F | Me | H | H | H | H |
| C—Ome | F—Cy | NH2 | F | Me | H | H | H | H |
| C—Me | F—Cy | NH2 | F | Me | H | H | H | H |
| N | Et | NH2 | F | Me | H | H | H | H |
| CH | Et | NH2 | F | Me | H | H | H | H |
| CF | Et | NH2 | F | Me | H | H | H | H |
| C—Cl | Et | NH2 | F | Me | H | H | H | H |
| C—Ome | Et | NH2 | F | Me | H | H | H | H |
| C—Me | Et | NH2 | F | Me | H | H | H | H |
| N | tBu | NH2 | F | Me | H | H | H | H |
| CH | tBu | NH2 | F | Me | H | H | H | H |
| N | 4F—Ph | NH2 | F | Me | H | H | H | H |

TABLE I-continued

| A1 | R1 | R5 | R6 | R7 | R'7 | R10 | R9 | R'9 |
|---|---|---|---|---|---|---|---|---|
| CH | 4F—Ph | NH2 | F | Me | H | H | H | H |
| CF | 4F—Ph | NH2 | F | Me | H | H | H | H |
| C—Cl | 4F—Ph | NH2 | F | Me | H | H | H | H |
| N | 2,4diFPh | NH2 | F | Me | H | H | H | H |
| CH | 2,4diFPh | NH2 | F | Me | H | H | H | H |
| CF | 2,4diFPh | NH2 | F | Me | H | H | H | H |
| C—Cl | 2,4diFPh | NH2 | F | Me | H | H | H | H |
| N | Cy | Me | F | Me | H | H | H | H |
| C—H | Cy | Me | F | Me | H | H | H | H |
| CF | Cy | Me | F | Me | H | H | H | H |
| C—Cl | Cy | Me | F | Me | H | H | H | H |
| C—Ome | Cy | Me | F | Me | H | H | H | H |
| C—Me | Cy | Me | F | Me | H | H | H | H |
| N | F—Cy | Me | F | Me | H | H | H | H |
| C—H | F—Cy | Me | F | Me | H | H | H | H |
| CF | F—Cy | Me | F | Me | H | H | H | H |
| C—Cl | F—Cy | Me | F | Me | H | H | H | H |
| C—Ome | F—Cy | Me | F | Me | H | H | H | H |
| C—Me | F—Cy | Me | F | Me | H | H | H | H |
| N | Et | Me | F | Me | H | H | H | H |
| CH | Et | Me | F | Me | H | H | H | H |
| CF | Et | Me | F | Me | H | H | H | H |
| C—Cl | Et | Me | F | Me | H | H | H | H |
| C—Ome | Et | Me | F | Me | H | H | H | H |
| C—Me | Et | Me | F | Me | H | H | H | H |
| N | tBu | Me | F | Me | H | H | H | H |
| CH | tBu | Me | F | Me | H | H | H | H |
| N | 4F—Ph | Me | F | Me | H | H | H | H |
| CH | 4F—Ph | Me | F | Me | H | H | H | H |
| CF | 4F—Ph | Me | F | Me | H | H | H | H |
| C—Cl | 4F—Ph | Me | F | Me | H | H | H | H |
| N | 2,4diFPh | Me | F | Me | H | H | H | H |
| CH | 2,4diFPh | Me | F | Me | H | H | H | H |
| CF | 2,4diFPh | Me | F | Me | H | H | H | H |
| C—Cl | 2,4diFPh | Me | F | Me | H | H | H | H |
| N | Cy | H | Cl | Me | H | H | H | H |
| C—H | Cy | H | Cl | Me | H | H | H | H |
| CF | Cy | H | Cl | Me | H | H | H | H |
| C—Cl | Cy | H | Cl | Me | H | H | H | H |
| C—Ome | Cy | H | Cl | Me | H | H | H | H |
| C—Me | Cy | H | Cl | Me | H | H | H | H |
| N | F—Cy | H | Cl | Me | H | H | H | H |
| C—H | F—Cy | H | Cl | Me | H | H | H | H |
| CF | F—Cy | H | Cl | Me | H | H | H | H |
| C—Cl | F—Cy | H | Cl | Me | H | H | H | H |
| C—Ome | F—Cy | H | Cl | Me | H | H | H | H |
| C—Me | F—Cy | H | Cl | Me | H | H | H | H |
| N | Et | H | Cl | Me | H | H | H | H |
| CH | Et | H | Cl | Me | H | H | H | H |
| CF | Et | H | Cl | Me | H | H | H | H |
| C—Cl | Et | H | Cl | Me | H | H | H | H |
| C—Ome | Et | H | Cl | Me | H | H | H | H |
| C—Me | Et | H | Cl | Me | H | H | H | H |
| N | tBu | H | Cl | Me | H | H | H | H |
| CH | tBu | H | Cl | Me | H | H | H | H |
| N | 4F—Ph | H | Cl | Me | H | H | H | H |
| CH | 4F—Ph | H | Cl | Me | H | H | H | H |
| CF | 4F—Ph | H | Cl | Me | H | H | H | H |
| C—Cl | 4F—Ph | H | Cl | Me | H | H | H | H |
| N | 2,4diFPh | H | Cl | Me | H | H | H | H |
| CH | 2,4diFPh | H | Cl | Me | H | H | H | H |
| CF | 2,4diFPh | H | Cl | Me | H | H | H | H |
| C—Cl | 2,4diFPh | H | Cl | Me | H | H | H | H |
| N | Cy | H | OH | Me | H | H | H | H |
| C—H | Cy | H | OH | Me | H | H | H | H |
| CF | Cy | H | OH | Me | H | H | H | H |
| C—Cl | Cy | H | OH | Me | H | H | H | H |
| C—Ome | Cy | H | OH | Me | H | H | H | H |
| C—Me | Cy | H | OH | Me | H | H | H | H |
| N | F—Cy | H | OH | Me | H | H | H | H |
| C—H | F—Cy | H | OH | Me | H | H | H | H |
| CF | F—Cy | H | OH | Me | H | H | H | H |
| C—Cl | F—Cy | H | OH | Me | H | H | H | H |
| C—Ome | F—Cy | H | OH | Me | H | H | H | H |
| C—Me | F—Cy | H | OH | Me | H | H | H | H |
| N | Et | H | OH | Me | H | H | H | H |
| CH | Et | H | OH | Me | H | H | H | H |
| CF | Et | H | OH | Me | H | H | H | H |
| C—Cl | Et | H | OH | Me | H | H | H | H |
| C—Ome | Et | H | OH | Me | H | H | H | H |
| C—Me | Et | H | OH | Me | H | H | H | H |
| N | tBu | H | OH | Me | H | H | H | H |
| CH | tBu | H | OH | Me | H | H | H | H |
| N | 4F—Ph | H | OH | Me | H | H | H | H |
| CH | 4F—Ph | H | OH | Me | H | H | H | H |
| CF | 4F—Ph | H | OH | Me | H | H | H | H |
| C—Cl | 4F—Ph | H | OH | Me | H | H | H | H |
| N | 2,4diFPh | H | OH | Me | H | H | H | H |
| CH | 2,4diFPh | H | OH | Me | H | H | H | H |
| CF | 2,4diFPh | H | OH | Me | H | H | H | H |
| C—Cl | 2,4diFPh | H | OH | Me | H | H | H | H |
| N | Cy | H | F | Et | H | H | H | H |
| C—H | Cy | H | F | Et | H | H | H | H |
| CF | Cy | H | F | Et | H | H | H | H |
| C—Cl | Cy | H | F | Et | H | H | H | H |
| C—Ome | Cy | H | F | Et | H | H | H | H |
| C—Me | Cy | H | F | Et | H | H | H | H |
| N | F—Cy | H | F | Et | H | H | H | H |
| C—H | F—Cy | H | F | Et | H | H | H | H |
| CF | F—Cy | H | F | Et | H | H | H | H |
| C—Cl | F—Cy | H | F | Et | H | H | H | H |
| C—Ome | F—Cy | H | F | Et | H | H | H | H |
| C—Me | F—Cy | H | F | Et | H | H | H | H |
| N | Et | H | F | Et | H | H | H | H |
| CH | Et | H | F | Et | H | H | H | H |
| CF | Et | H | F | Et | H | H | H | H |
| C—Cl | Et | H | F | Et | H | H | H | H |
| C—Ome | Et | H | F | Et | H | H | H | H |
| C—Me | Et | H | F | Et | H | H | H | H |
| N | tBu | H | F | Et | H | H | H | H |
| CH | tBu | H | F | Et | H | H | H | H |
| N | 4F—Ph | H | F | Et | H | H | H | H |
| CH | 4F—Ph | H | F | Et | H | H | H | H |
| CF | 4F—Ph | H | F | Et | H | H | H | H |
| C—Cl | 4F—Ph | H | F | Et | H | H | H | H |
| N | 2,4diFPh | H | F | Et | H | H | H | H |
| CH | 2,4diFPh | H | F | Et | H | H | H | H |
| CF | 2,4diFPh | H | F | Et | H | H | H | H |
| C—Cl | 2,4diFPh | H | F | Et | H | H | H | H |
| N | Cy | NH2 | F | Et | H | H | H | H |
| C—H | Cy | NH2 | F | Et | H | H | H | H |
| CF | Cy | NH2 | F | Et | H | H | H | H |
| C—Cl | Cy | NH2 | F | Et | H | H | H | H |
| C—Ome | Cy | NH2 | F | Et | H | H | H | H |
| C—Me | Cy | NH2 | F | Et | H | H | H | H |
| N | F—Cy | NH2 | F | Et | H | H | H | H |
| C—H | F—Cy | NH2 | F | Et | H | H | H | H |
| CF | F—Cy | NH2 | F | Et | H | H | H | H |
| C—Cl | F—Cy | NH2 | F | Et | H | H | H | H |
| C—Ome | F—Cy | NH2 | F | Et | H | H | H | H |
| C—Me | F—Cy | NH2 | F | Et | H | H | H | H |
| N | Et | NH2 | F | Et | H | H | H | H |
| CH | Et | NH2 | F | Et | H | H | H | H |
| CF | Et | NH2 | F | Et | H | H | H | H |
| C—Cl | Et | NH2 | F | Et | H | H | H | H |
| C—Ome | Et | NH2 | F | Et | H | H | H | H |
| C—Me | Et | NH2 | F | Et | H | H | H | H |
| N | tBu | NH2 | F | Et | H | H | H | H |
| CH | tBu | NH2 | F | Et | H | H | H | H |
| N | 4F—Ph | NH2 | F | Et | H | H | H | H |
| CH | 4F—Ph | NH2 | F | Et | H | H | H | H |
| CF | 4F—Ph | NH2 | F | Et | H | H | H | H |
| C—Cl | 4F—Ph | NH2 | F | Et | H | H | H | H |
| N | 2,4diFPh | NH2 | F | Et | H | H | H | H |
| CH | 2,4diFPh | NH2 | F | Et | H | H | H | H |
| CF | 2,4diFPh | NH2 | F | Et | H | H | H | H |
| C—Cl | 2,4diFPh | NH2 | F | Et | H | H | H | H |
| N | Cy | Me | F | Et | H | H | H | H |
| C—H | Cy | Me | F | Et | H | H | H | H |
| CF | Cy | Me | F | Et | H | H | H | H |
| C—Cl | Cy | Me | F | Et | H | H | H | H |
| C—Ome | Cy | Me | F | Et | H | H | H | H |
| C—Me | Cy | Me | F | Et | H | H | H | H |
| N | F—Cy | Me | F | Et | H | H | H | H |

TABLE I-continued

| A1 | R1 | R5 | R6 | R7 | R'7 | R10 | R9 | R'9 |
|---|---|---|---|---|---|---|---|---|
| C—H | F—Cy | Me | F | Et | H | H | H | H |
| CF | F—Cy | Me | F | Et | H | H | H | H |
| C—Cl | F—Cy | Me | F | Et | H | H | H | H |
| C—Ome | F—Cy | Me | F | Et | H | H | H | H |
| C—Me | F—Cy | Me | F | Et | H | H | H | H |
| N | Et | Me | F | Et | H | H | H | H |
| CH | Et | Me | F | Et | H | H | H | H |
| CF | Et | Me | F | Et | H | H | H | H |
| C—Cl | Et | Me | F | Et | H | H | H | H |
| C—Ome | Et | Me | F | Et | H | H | H | H |
| C—Me | Et | Me | F | Et | H | H | H | H |
| N | tBu | Me | F | Et | H | H | H | H |
| CH | tBu | Me | F | Et | H | H | H | H |
| N | 4F—Ph | Me | F | Et | H | H | H | H |
| CH | 4F—Ph | Me | F | Et | H | H | H | H |
| CF | 4F—Ph | Me | F | Et | H | H | H | H |
| C—Cl | 4F—Ph | Me | F | Et | H | H | H | H |
| N | 2,4diFPh | Me | F | Et | H | H | H | H |
| CH | 2,4diFPh | Me | F | Et | H | H | H | H |
| CF | 2,4diFPh | Me | F | Et | H | H | H | H |
| C—Cl | 2,4diFPh | Me | F | Et | H | H | H | H |
| N | Cy | H | Cl | Et | H | H | H | H |
| C—H | Cy | H | Cl | Et | H | H | H | H |
| CF | Cy | H | Cl | Et | H | H | H | H |
| C—Cl | Cy | H | Cl | Et | H | H | H | H |
| C—Ome | Cy | H | Cl | Et | H | H | H | H |
| C—Me | Cy | H | Cl | Et | H | H | H | H |
| N | F—Cy | H | Cl | Et | H | H | H | H |
| C—H | F—Cy | H | Cl | Et | H | H | H | H |
| CF | F—Cy | H | Cl | Et | H | H | H | H |
| C—Cl | F—Cy | H | Cl | Et | H | H | H | H |
| C—Ome | F—Cy | H | Cl | Et | H | H | H | H |
| C—Me | F—Cy | H | Cl | Et | H | H | H | H |
| N | Et | H | Cl | Et | H | H | H | H |
| CH | Et | H | Cl | Et | H | H | H | H |
| CF | Et | H | Cl | Et | H | H | H | H |
| C—Cl | Et | H | Cl | Et | H | H | H | H |
| C—Ome | Et | H | Cl | Et | H | H | H | H |
| C—Me | Et | H | Cl | Et | H | H | H | H |
| N | tBu | H | Cl | Et | H | H | H | H |
| CH | tBu | H | Cl | Et | H | H | H | H |
| N | 4F—Ph | H | Cl | Et | H | H | H | H |
| CH | 4F—Ph | H | Cl | Et | H | H | H | H |
| CF | 4F—Ph | H | Cl | Et | H | H | H | H |
| C—Cl | 4F—Ph | H | Cl | Et | H | H | H | H |
| N | 2,4diFPh | H | Cl | Et | H | H | H | H |
| CH | 2,4diFPh | H | Cl | Et | H | H | H | H |
| CF | 2,4diFPh | H | Cl | Et | H | H | H | H |
| C—Cl | 2,4diFPh | H | Cl | Et | H | H | H | H |
| N | Cy | H | OH | Et | H | H | H | H |
| C—H | Cy | H | OH | Et | H | H | H | H |
| CF | Cy | H | OH | Et | H | H | H | H |
| C—Cl | Cy | H | OH | Et | H | H | H | H |
| C—Ome | Cy | H | OH | Et | H | H | H | H |
| C—Me | Cy | H | OH | Et | H | H | H | H |
| N | F—Cy | H | OH | Et | H | H | H | H |
| C—H | F—Cy | H | OH | Et | H | H | H | H |
| CF | F—Cy | H | OH | Et | H | H | H | H |
| C—Cl | F—Cy | H | OH | Et | H | H | H | H |
| C—Ome | F—Cy | H | OH | Et | H | H | H | H |
| C—Me | F—Cy | H | OH | Et | H | H | H | H |
| N | Et | H | OH | Et | H | H | H | H |
| CH | Et | H | OH | Et | H | H | H | H |
| CF | Et | H | OH | Et | H | H | H | H |
| C—Cl | Et | H | OH | Et | H | H | H | H |
| C—Ome | Et | H | OH | Et | H | H | H | H |
| C—Me | Et | H | OH | Et | H | H | H | H |
| N | tBu | H | OH | Et | H | H | H | H |
| CH | tBu | H | OH | Et | H | H | H | H |
| N | 4F—Ph | H | OH | Et | H | H | H | H |
| CH | 4F—Ph | H | OH | Et | H | H | H | H |
| CF | 4F—Ph | H | OH | Et | H | H | H | H |
| C—Cl | 4F—Ph | H | OH | Et | H | H | H | H |
| N | 2,4diFPh | H | OH | Et | H | H | H | H |
| CH | 2,4diFPh | H | OH | Et | H | H | H | H |
| CF | 2,4diFPh | H | OH | Et | H | H | H | H |
| C—Cl | 2,4diFPh | H | OH | Et | H | H | H | H |
| N | Cy | H | F | OMe | H | H | H | H |
| C—H | Cy | H | F | OMe | H | H | H | H |
| CF | Cy | H | F | OMe | H | H | H | H |
| C—Cl | Cy | H | F | OMe | H | H | H | H |
| C—Ome | Cy | H | F | OMe | H | H | H | H |
| C—Me | Cy | H | F | OMe | H | H | H | H |
| N | F—Cy | H | F | OMe | H | H | H | H |
| C—H | F—Cy | H | F | OMe | H | H | H | H |
| CF | F—Cy | H | F | OMe | H | H | H | H |
| C—Cl | F—Cy | H | F | OMe | H | H | H | H |
| C—Ome | F—Cy | H | F | OMe | H | H | H | H |
| C—Me | F—Cy | H | F | OMe | H | H | H | H |
| N | Et | H | F | OMe | H | H | H | H |
| CH | Et | H | F | OMe | H | H | H | H |
| CF | Et | H | F | OMe | H | H | H | H |
| C—Cl | Et | H | F | OMe | H | H | H | H |
| C—Ome | Et | H | F | OMe | H | H | H | H |
| C—Me | Et | H | F | OMe | H | H | H | H |
| N | tBu | H | F | OMe | H | H | H | H |
| CH | tBu | H | F | OMe | H | H | H | H |
| N | 4F—Ph | H | F | OMe | H | H | H | H |
| CH | 4F—Ph | H | F | OMe | H | H | H | H |
| CF | 4F—Ph | H | F | OMe | H | H | H | H |
| C—Cl | 4F—Ph | H | F | OMe | H | H | H | H |
| N | 2,4diFPh | H | F | OMe | H | H | H | H |
| CH | 2,4diFPh | H | F | OMe | H | H | H | H |
| CF | 2,4diFPh | H | F | OMe | H | H | H | H |
| C—Cl | 2,4diFPh | H | F | OMe | H | H | H | H |
| N | Cy | H | F | CH$_2$F | H | H | H | H |
| C—H | Cy | H | F | CH$_2$F | H | H | H | H |
| CF | Cy | H | F | CH$_2$F | H | H | H | H |
| C—Cl | Cy | H | F | CH$_2$F | H | H | H | H |
| C—Ome | Cy | H | F | CH$_2$F | H | H | H | H |
| C—Me | Cy | H | F | CH$_2$F | H | H | H | H |
| N | F—Cy | H | F | CH$_2$F | H | H | H | H |
| C—H | F—Cy | H | F | CH$_2$F | H | H | H | H |
| CF | F—Cy | H | F | CH$_2$F | H | H | H | H |
| C—Cl | F—Cy | H | F | CH$_2$F | H | H | H | H |
| C—Ome | F—Cy | H | F | CH$_2$F | H | H | H | H |
| C—Me | F—Cy | H | F | CH$_2$F | H | H | H | H |
| N | Et | H | F | CH$_2$F | H | H | H | H |
| CH | Et | H | F | CH$_2$F | H | H | H | H |
| CF | Et | H | F | CH$_2$F | H | H | H | H |
| C—Cl | Et | H | F | CH$_2$F | H | H | H | H |
| C—Ome | Et | H | F | CH$_2$F | H | H | H | H |
| C—Me | Et | H | F | CH$_2$F | H | H | H | H |
| N | tBu | H | F | CH$_2$F | H | H | H | H |
| CH | tBu | H | F | CH$_2$F | H | H | H | H |
| N | 4F—Ph | H | F | CH$_2$F | H | H | H | H |
| CH | 4F—Ph | H | F | CH$_2$F | H | H | H | H |
| CF | 4F—Ph | H | F | CH$_2$F | H | H | H | H |
| C—Cl | 4F—Ph | H | F | CH$_2$F | H | H | H | H |
| N | 2,4diFPh | H | F | CH$_2$F | H | H | H | H |
| CH | 2,4diFPh | H | F | CH$_2$F | H | H | H | H |
| CF | 2,4diFPh | H | F | CH$_2$F | H | H | H | H |
| C—Cl | 2,4diFPh | H | F | CH$_2$F | H | H | H | H |
| N | Cy | H | F | Me | Me | H | H | H |
| C—H | Cy | H | F | Me | Me | H | H | H |
| CF | Cy | H | F | Me | Me | H | H | H |
| C—Cl | Cy | H | F | Me | Me | H | H | H |
| C—Ome | Cy | H | F | Me | Me | H | H | H |
| C—Me | Cy | H | F | Me | Me | H | H | H |
| N | F—Cy | H | F | Me | Me | H | H | H |
| C—H | F—Cy | H | F | Me | Me | H | H | H |
| CF | F—Cy | H | F | Me | Me | H | H | H |
| C—Cl | F—Cy | H | F | Me | Me | H | H | H |
| C—Ome | F—Cy | H | F | Me | Me | H | H | H |
| C—Me | F—Cy | H | F | Me | Me | H | H | H |
| N | Et | H | F | Me | Me | H | H | H |
| CH | Et | H | F | Me | Me | H | H | H |
| CF | Et | H | F | Me | Me | H | H | H |
| C—Cl | Et | H | F | Me | Me | H | H | H |
| C—Ome | Et | H | F | Me | Me | H | H | H |
| C—Me | Et | H | F | Me | Me | H | H | H |
| N | tBu | H | F | Me | Me | H | H | H |
| CH | tBu | H | F | Me | Me | H | H | H |
| N | 4F—Ph | H | F | Me | Me | H | H | H |

TABLE I-continued

| A1 | R1 | R5 | R6 | R7 | R'7 | R10 | R9 | R'9 |
|---|---|---|---|---|---|---|---|---|
| CH | 4F—Ph | H | F | Me | Me | H | H | H |
| CF | 4F—Ph | H | F | Me | Me | H | H | H |
| C—Cl | 4F—Ph | H | F | Me | Me | H | H | H |
| N | 2,4diFPh | H | F | Me | Me | H | H | H |
| CH | 2,4diFPh | H | F | Me | Me | H | H | H |
| CF | 2,4diFPh | H | F | Me | Me | H | H | H |
| C—Cl | 2,4diFPh | H | F | Me | Me | H | H | H |
| N | Cy | H | F | Me | H | Me | H | H |
| C—H | Cy | H | F | Me | H | Me | H | H |
| CF | Cy | H | F | Me | H | Me | H | H |
| C—Cl | Cy | H | F | Me | H | Me | H | H |
| C—Ome | Cy | H | F | Me | H | Me | H | H |
| C—Me | Cy | H | F | Me | H | Me | H | H |
| N | F—Cy | H | F | Me | H | Me | H | H |
| C—H | F—Cy | H | F | Me | H | Me | H | H |
| CF | F—Cy | H | F | Me | H | Me | H | H |
| C—Cl | F—Cy | H | F | Me | H | Me | H | H |
| C—Ome | F—Cy | H | F | Me | H | Me | H | H |
| C—Me | F—Cy | H | F | Me | H | Me | H | H |
| N | Et | H | F | Me | H | Me | H | H |
| CH | Et | H | F | Me | H | Me | H | H |
| CF | Et | H | F | Me | H | Me | H | H |
| C—Cl | Et | H | F | Me | H | Me | H | H |
| C—Ome | Et | H | F | Me | H | Me | H | H |
| C—Me | Et | H | F | Me | H | Me | H | H |
| N | tBu | H | F | Me | H | Me | H | H |
| CH | tBu | H | F | Me | H | Me | H | H |
| N | 4F—Ph | H | F | Me | H | Me | H | H |
| CH | 4F—Ph | H | F | Me | H | Me | H | H |
| CF | 4F—Ph | H | F | Me | H | Me | H | H |
| C—Cl | 4F—Ph | H | F | Me | H | Me | H | H |
| N | 2,4diFPh | H | F | Me | H | Me | H | H |
| CH | 2,4diFPh | H | F | Me | H | Me | H | H |
| CF | 2,4diFPh | H | F | Me | H | Me | H | H |
| C—Cl | 2,4diFPh | H | F | Me | H | Me | H | H |
| N | Cy | H | F | Me | H | Et | H | H |
| C—H | Cy | H | F | Me | H | Et | H | H |
| CF | Cy | H | F | Me | H | Et | H | H |
| C—Cl | Cy | H | F | Me | H | Et | H | H |
| C—Ome | Cy | H | F | Me | H | Et | H | H |
| C—Me | Cy | H | F | Me | H | Et | H | H |
| N | F—Cy | H | F | Me | H | Et | H | H |
| C—H | F—Cy | H | F | Me | H | Et | H | H |
| CF | F—Cy | H | F | Me | H | Et | H | H |
| C—Cl | F—Cy | H | F | Me | H | Et | H | H |
| C—Ome | F—Cy | H | F | Me | H | Et | H | H |
| C—Me | F—Cy | H | F | Me | H | Et | H | H |
| N | Et | H | F | Me | H | Et | H | H |
| CH | Et | H | F | Me | H | Et | H | H |
| CF | Et | H | F | Me | H | Et | H | H |
| C—Cl | Et | H | F | Me | H | Et | H | H |
| C—Ome | Et | H | F | Me | H | Et | H | H |
| C—Me | Et | H | F | Me | H | Et | H | H |
| N | tBu | H | F | Me | H | Et | H | H |
| CH | tBu | H | F | Me | H | Et | H | H |
| N | 4F—Ph | H | F | Me | H | Et | H | H |
| CH | 4F—Ph | H | F | Me | H | Et | H | H |
| CF | 4F—Ph | H | F | Me | H | Et | H | H |
| C—Cl | 4F—Ph | H | F | Me | H | Et | H | H |
| N | 2,4diFPh | H | F | Me | H | Et | H | H |
| CH | 2,4diFPh | H | F | Me | H | Et | H | H |
| CF | 2,4diFPh | H | F | Me | H | Et | H | H |
| C—Cl | 2,4diFPh | H | F | Me | H | Et | H | H |
| N | Cy | H | F | Me | H | H | Me | H |
| C—H | Cy | H | F | Me | H | H | Me | H |
| CF | Cy | H | F | Me | H | H | Me | H |
| C—Cl | Cy | H | F | Me | H | H | Me | H |
| C—Ome | Cy | H | F | Me | H | H | Me | H |
| C—Me | Cy | H | F | Me | H | H | Me | H |
| N | F—Cy | H | F | Me | H | H | Me | H |
| C—H | F—Cy | H | F | Me | H | H | Me | H |
| CF | F—Cy | H | F | Me | H | H | Me | H |
| C—Cl | F—Cy | H | F | Me | H | H | Me | H |
| C—Ome | F—Cy | H | F | Me | H | H | Me | H |
| C—Me | F—Cy | H | F | Me | H | H | Me | H |
| N | Et | H | F | Me | H | H | Me | H |
| CH | Et | H | F | Me | H | H | Me | H |
| CF | Et | H | F | Me | H | H | Me | H |
| C—Cl | Et | H | F | Me | H | H | Me | H |
| C—Ome | Et | H | F | Me | H | H | Me | H |
| C—Me | Et | H | F | Me | H | H | Me | H |
| N | tBu | H | F | Me | H | H | Me | H |
| CH | tBu | H | F | Me | H | H | Me | H |
| N | 4F—Ph | H | F | Me | H | H | Me | H |
| CH | 4F—Ph | H | F | Me | H | H | Me | H |
| CF | 4F—Ph | H | F | Me | H | H | Me | H |
| C—Cl | 4F—Ph | H | F | Me | H | H | Me | H |
| N | 2,4diFPh | H | F | Me | H | H | Me | H |
| CH | 2,4diFPh | H | F | Me | H | H | Me | H |
| CF | 2,4diFPh | H | F | Me | H | H | Me | H |
| C—Cl | 2,4diFPh | H | F | Me | H | H | Me | H |
| N | Cy | H | F | Me | H | H | Me | Me |
| C—H | Cy | H | F | Me | H | H | Me | Me |
| CF | Cy | H | F | Me | H | H | Me | Me |
| C—Cl | Cy | H | F | Me | H | H | Me | Me |
| C—Ome | Cy | H | F | Me | H | H | Me | Me |
| C—Me | Cy | H | F | Me | H | H | Me | Me |
| N | F—Cy | H | F | Me | H | H | Me | Me |
| C—H | F—Cy | H | F | Me | H | H | Me | Me |
| CF | F—Cy | H | F | Me | H | H | Me | Me |
| C—Cl | F—Cy | H | F | Me | H | H | Me | Me |
| C—Ome | F—Cy | H | F | Me | H | H | Me | Me |
| C—Me | F—Cy | H | F | Me | H | H | Me | Me |
| N | Et | H | F | Me | H | H | Me | Me |
| CH | Et | H | F | Me | H | H | Me | Me |
| CF | Et | H | F | Me | H | H | Me | Me |
| C—Cl | Et | H | F | Me | H | H | Me | Me |
| C—Ome | Et | H | F | Me | H | H | Me | Me |
| C—Me | Et | H | F | Me | H | H | Me | Me |
| N | tBu | H | F | Me | H | H | Me | Me |
| CH | tBu | H | F | Me | H | H | Me | Me |
| N | 4F—Ph | H | F | Me | H | H | Me | Me |
| CH | 4F—Ph | H | F | Me | H | H | Me | Me |
| CF | 4F—Ph | H | F | Me | H | H | Me | Me |
| C—Cl | 4F—Ph | H | F | Me | H | H | Me | Me |
| N | 2,4diFPh | H | F | Me | H | H | Me | Me |
| CH | 2,4diFPh | H | F | Me | H | H | Me | Me |
| CF | 2,4diFPh | H | F | Me | H | H | Me | Me |
| C—Cl | 2,4diFPh | H | F | Me | H | H | Me | Me |

Table II contains a non-limiting list of compounds of Formula (B).

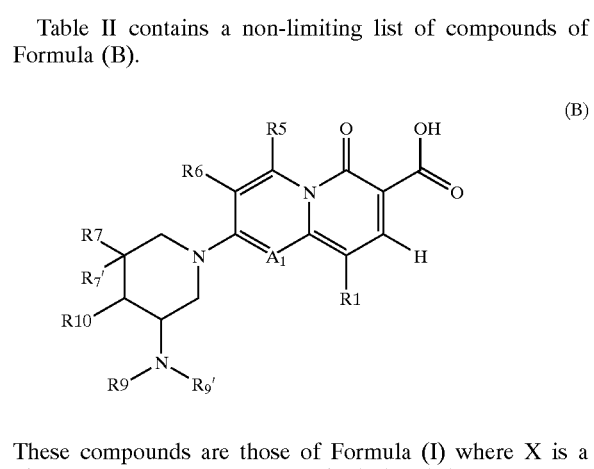

These compounds are those of Formula (I) where X is a nitrogen atom, a represents a single bond, b represents a double bond, c represents a double bond, and Y is —CR$^1$—.

| A1 | R1 | R5 | R6 | R7 | R7' | R10 | R9 | R9' |
|---|---|---|---|---|---|---|---|---|
| N | Cy | H | F | Me | H | H | H | H |
| C—H | Cy | H | F | Me | H | H | H | H |
| CF | Cy | H | F | Me | H | H | H | H |
| C—Cl | Cy | H | F | Me | H | H | H | H |

-continued

| A1 | R1 | R5 | R6 | R7 | R7' | R10 | R9 | R9' |
|---|---|---|---|---|---|---|---|---|
| C—Ome | Cy | H | F | Me | H | H | H | H |
| C—Me | Cy | H | F | Me | H | H | H | H |
| N | F—Cy | H | F | Me | H | H | H | H |
| C—H | F—Cy | H | F | Me | H | H | H | H |
| CF | F—Cy | H | F | Me | H | H | H | H |
| C—Cl | F—Cy | H | F | Me | H | H | H | H |
| C—Ome | F—Cy | H | F | Me | H | H | H | H |
| C—Me | F—Cy | H | F | Me | H | H | H | H |
| N | Et | H | F | Me | H | H | H | H |
| CH | Et | H | F | Me | H | H | H | H |
| CF | Et | H | F | Me | H | H | H | H |
| C—Cl | Et | H | F | Me | H | H | H | H |
| C—Ome | Et | H | F | Me | H | H | H | H |
| C—Me | Et | H | F | Me | H | H | H | H |
| N | tBu | H | F | Me | H | H | H | H |
| CH | tBu | H | F | Me | H | H | H | H |
| N | 4F—Ph | H | F | Me | H | H | H | H |
| CH | 4F—Ph | H | F | Me | H | H | H | H |
| CF | 4F—Ph | H | F | Me | H | H | H | H |
| C—Cl | 4F—Ph | H | F | Me | H | H | H | H |
| N | 2,4diFPh | H | F | Me | H | H | H | H |
| CH | 2,4diFPh | H | F | Me | H | H | H | H |
| CF | 2,4diFPh | H | F | Me | H | H | H | H |
| C—Cl | 2,4diFPh | H | F | Me | H | H | H | H |
| N | Cy | Me | F | Et | H | H | H | H |
| C—H | Cy | Me | F | Et | H | H | H | H |
| CF | Cy | Me | F | Et | H | H | H | H |
| C—Cl | Cy | Me | F | Et | H | H | H | H |
| C—Ome | Cy | Me | F | Et | H | H | H | H |
| C—Me | Cy | Me | F | Et | H | H | H | H |
| N | F—Cy | Me | F | Et | H | H | H | H |
| C—H | F—Cy | Me | F | Et | H | H | H | H |
| CF | F—Cy | Me | F | Et | H | H | H | H |
| C—Cl | F—Cy | Me | F | Et | H | H | H | H |
| C—Ome | F—Cy | Me | F | Et | H | H | H | H |
| C—Me | F—Cy | Me | F | Et | H | H | H | H |
| N | Et | Me | F | Et | H | H | H | H |
| CH | Et | Me | F | Et | H | H | H | H |
| CF | Et | Me | F | Et | H | H | H | H |
| C—Cl | Et | Me | F | Et | H | H | H | H |
| C—Ome | Et | Me | F | Et | H | H | H | H |
| C—Me | Et | Me | F | Et | H | H | H | H |
| N | tBu | Me | F | Et | H | H | H | H |
| CH | tBu | Me | F | Et | H | H | H | H |
| N | 4F—Ph | Me | F | Et | H | H | H | H |
| CH | 4F—Ph | Me | F | Et | H | H | H | H |
| CF | 4F—Ph | Me | F | Et | H | H | H | H |
| C—Cl | 4F—Ph | Me | F | Et | H | H | H | H |
| N | 2,4diFPh | Me | F | Et | H | H | H | H |
| CH | 2,4diFPh | Me | F | Et | H | H | H | H |
| CF | 2,4diFPh | Me | F | Et | H | H | H | H |
| C—Cl | 2,4diFPh | Me | F | Et | H | H | H | H |
| N | Cy | H | F | OMe | H | H | H | H |
| C—H | Cy | H | F | OMe | H | H | H | H |
| CF | Cy | H | F | OMe | H | H | H | H |
| C—Cl | Cy | H | F | OMe | H | H | H | H |
| C—Ome | Cy | H | F | OMe | H | H | H | H |
| C—Me | Cy | H | F | OMe | H | H | H | H |
| N | F—Cy | H | F | OMe | H | H | H | H |
| C—H | F—Cy | H | F | OMe | H | H | H | H |
| CF | F—Cy | H | F | OMe | H | H | H | H |
| C—Cl | F—Cy | H | F | OMe | H | H | H | H |
| C—Ome | F—Cy | H | F | OMe | H | H | H | H |
| C—Me | F—Cy | H | F | OMe | H | H | H | H |
| N | Et | H | F | OMe | H | H | H | H |
| CH | Et | H | F | OMe | H | H | H | H |
| CF | Et | H | F | OMe | H | H | H | H |
| C—Cl | Et | H | F | OMe | H | H | H | H |
| C—Ome | Et | H | F | OMe | H | H | H | H |
| C—Me | Et | H | F | OMe | H | H | H | H |
| N | tBu | H | F | OMe | H | H | H | H |
| CH | tBu | H | F | OMe | H | H | H | H |
| N | 4F—Ph | H | F | OMe | H | H | H | H |
| CH | 4F—Ph | H | F | OMe | H | H | H | H |
| CF | 4F—Ph | H | F | OMe | H | H | H | H |
| C—Cl | 4F—Ph | H | F | OMe | H | H | H | H |
| N | 2,4diFPh | H | F | OMe | H | H | H | H |
| CH | 2,4diFPh | H | F | OMe | H | H | H | H |
| CF | 2,4diFPh | H | F | OMe | H | H | H | H |
| C—Cl | 2,4diFPh | H | F | OMe | H | H | H | H |
| N | Cy | H | F | $CH_2F$ | H | H | H | H |
| C—H | Cy | H | F | $CH_2F$ | H | H | H | H |
| CF | Cy | H | F | $CH_2F$ | H | H | H | H |
| C—Cl | Cy | H | F | $CH_2F$ | H | H | H | H |
| C—Ome | Cy | H | F | $CH_2F$ | H | H | H | H |
| C—Me | Cy | H | F | $CH_2F$ | H | H | H | H |
| N | F—Cy | H | F | $CH_2F$ | H | H | H | H |
| C—H | F—Cy | H | F | $CH_2F$ | H | H | H | H |
| CF | F—Cy | H | F | $CH_2F$ | H | H | H | H |
| C—Cl | F—Cy | H | F | $CH_2F$ | H | H | H | H |
| C—Ome | F—Cy | H | F | $CH_2F$ | H | H | H | H |
| C—Me | F—Cy | H | F | $CH_2F$ | H | H | H | H |
| N | Et | H | F | $CH_2F$ | H | H | H | H |
| CH | Et | H | F | $CH_2F$ | H | H | H | H |
| CF | Et | H | F | $CH_2F$ | H | H | H | H |
| C—Cl | Et | H | F | $CH_2F$ | H | H | H | H |
| C—Ome | Et | H | F | $CH_2F$ | H | H | H | H |
| C—Me | Et | H | F | $CH_2F$ | H | H | H | H |
| N | tBu | H | F | $CH_2F$ | H | H | H | H |
| CH | tBu | H | F | $CH_2F$ | H | H | H | H |
| N | 4F—Ph | H | F | $CH_2F$ | H | H | H | H |
| CH | 4F—Ph | H | F | $CH_2F$ | H | H | H | H |
| CF | 4F—Ph | H | F | $CH_2F$ | H | H | H | H |
| C—Cl | 4F—Ph | H | F | $CH_2F$ | H | H | H | H |
| N | 2,4diFPh | H | F | $CH_2F$ | H | H | H | H |
| CH | 2,4diFPh | H | F | $CH_2F$ | H | H | H | H |
| CF | 2,4diFPh | H | F | $CH_2F$ | H | H | H | H |
| C—Cl | 2,4diFPh | H | F | $CH_2F$ | H | H | H | H |
| N | Cy | H | F | Me | Me | H | H | H |
| C—H | Cy | H | F | Me | Me | H | H | H |
| CF | Cy | H | F | Me | Me | H | H | H |
| C—Cl | Cy | H | F | Me | Me | H | H | H |
| C—Ome | Cy | H | F | Me | Me | H | H | H |
| C—Me | Cy | H | F | Me | Me | H | H | H |
| N | F—Cy | H | F | Me | Me | H | H | H |
| C—H | F—Cy | H | F | Me | Me | H | H | H |
| CF | F—Cy | H | F | Me | Me | H | H | H |
| C—Cl | F—Cy | H | F | Me | Me | H | H | H |
| C—Ome | F—Cy | H | F | Me | Me | H | H | H |
| C—Me | F—Cy | H | F | Me | Me | H | H | H |
| N | Et | H | F | Me | Me | H | H | H |
| CH | Et | H | F | Me | Me | H | H | H |
| CF | Et | H | F | Me | Me | H | H | H |
| C—Cl | Et | H | F | Me | Me | H | H | H |
| C—Ome | Et | H | F | Me | Me | H | H | H |
| C—Me | Et | H | F | Me | Me | H | H | H |
| N | tBu | H | F | Me | Me | H | H | H |
| CH | tBu | H | F | Me | Me | H | H | H |
| N | 4F—Ph | H | F | Me | Me | H | H | H |
| CH | 4F—Ph | H | F | Me | Me | H | H | H |
| CF | 4F—Ph | H | F | Me | Me | H | H | H |
| C—Cl | 4F—Ph | H | F | Me | Me | H | H | H |
| N | 2,4diFPh | H | F | Me | Me | H | H | H |
| CH | 2,4diFPh | H | F | Me | Me | H | H | H |
| CF | 2,4diFPh | H | F | Me | Me | H | H | H |
| C—Cl | 2,4diFPh | H | F | Me | Me | H | H | H |
| N | Cy | H | F | Me | H | Me | H | H |
| C—H | Cy | H | F | Me | H | Me | H | H |
| CF | Cy | H | F | Me | H | Me | H | H |
| C—Cl | Cy | H | F | Me | H | Me | H | H |
| C—Ome | Cy | H | F | Me | H | Me | H | H |
| C—Me | Cy | H | F | Me | H | Me | H | H |
| N | F—Cy | H | F | Me | H | Me | H | H |
| C—H | F—Cy | H | F | Me | H | Me | H | H |
| CF | F—Cy | H | F | Me | H | Me | H | H |
| C—Cl | F—Cy | H | F | Me | H | Me | H | H |
| C—Ome | F—Cy | H | F | Me | H | Me | H | H |
| C—Me | F—Cy | H | F | Me | H | Me | H | H |
| N | Et | H | F | Me | H | Me | H | H |
| CH | Et | H | F | Me | H | Me | H | H |
| CF | Et | H | F | Me | H | Me | H | H |
| C—Cl | Et | H | F | Me | H | Me | H | H |
| C—Ome | Et | H | F | Me | H | Me | H | H |
| C—Me | Et | H | F | Me | H | Me | H | H |

-continued

| A1 | R1 | R5 | R6 | R7 | R7' | R10 | R9 | R9' |
|---|---|---|---|---|---|---|---|---|
| N | tBu | H | F | Me | H | Me | H | H |
| CH | tBu | H | F | Me | H | Me | H | H |
| N | 4F—Ph | H | F | Me | H | Me | H | H |
| CH | 4F—Ph | H | F | Me | H | Me | H | H |
| CF | 4F—Ph | H | F | Me | H | Me | H | H |
| C—Cl | 4F—Ph | H | F | Me | H | Me | H | H |
| N | 2,4diFPh | H | F | Me | H | Me | H | H |
| CH | 2,4diFPh | H | F | Me | H | Me | H | H |
| CF | 2,4diFPh | H | F | Me | H | Me | H | H |
| C—Cl | 2,4diFPh | H | F | Me | H | Me | H | H |
| N | Cy | H | F | Me | H | Et | H | H |
| C—H | Cy | H | F | Me | H | Et | H | H |
| CF | Cy | H | F | Me | H | Et | H | H |
| C—Cl | Cy | H | F | Me | H | Et | H | H |
| C—Ome | Cy | H | F | Me | H | Et | H | H |
| C—Me | Cy | H | F | Me | H | Et | H | H |
| N | F—Cy | H | F | Me | H | Et | H | H |
| C—H | F—Cy | H | F | Me | H | Et | H | H |
| CF | F—Cy | H | F | Me | H | Et | H | H |
| C—Cl | F—Cy | H | F | Me | H | Et | H | H |
| C—Ome | F—Cy | H | F | Me | H | Et | H | H |
| C—Me | F—Cy | H | F | Me | H | Et | H | H |
| N | Et | H | F | Me | H | Et | H | H |
| CH | Et | H | F | Me | H | Et | H | H |
| CF | Et | H | F | Me | H | Et | H | H |
| C—Cl | Et | H | F | Me | H | Et | H | H |
| C—Ome | Et | H | F | Me | H | Et | H | H |
| C—Me | Et | H | F | Me | H | Et | H | H |
| N | tBu | H | F | Me | H | Et | H | H |
| CH | tBu | H | F | Me | H | Et | H | H |
| N | 4F—Ph | H | F | Me | H | Et | H | H |
| CH | 4F—Ph | H | F | Me | H | Et | H | H |
| CF | 4F—Ph | H | F | Me | H | Et | H | H |
| C—Cl | 4F—Ph | H | F | Me | H | Et | H | H |
| N | 2,4diFPh | H | F | Me | H | Et | H | H |
| CH | 2,4diFPh | H | F | Me | H | Et | H | H |
| CF | 2,4diFPh | H | F | Me | H | Et | H | H |
| C—Cl | 2,4diFPh | H | F | Me | H | Et | H | H |
| N | Cy | H | F | Me | H | H | Me | H |
| C—H | Cy | H | F | Me | H | H | Me | H |
| CF | Cy | H | F | Me | H | H | Me | H |
| C—Cl | Cy | H | F | Me | H | H | Me | H |
| C—Ome | Cy | H | F | Me | H | H | Me | H |
| C—Me | Cy | H | F | Me | H | H | Me | H |
| N | F—Cy | H | F | Me | H | H | Me | H |
| C—H | F—Cy | H | F | Me | H | H | Me | H |
| CF | F—Cy | H | F | Me | H | H | Me | H |
| C—Cl | F—Cy | H | F | Me | H | H | Me | H |
| C—Ome | F—Cy | H | F | Me | H | H | Me | H |
| C—Me | F—Cy | H | F | Me | H | H | Me | H |
| N | Et | H | F | Me | H | H | Me | H |
| CH | Et | H | F | Me | H | H | Me | H |
| CF | Et | H | F | Me | H | H | Me | H |
| C—Cl | Et | H | F | Me | H | H | Me | H |
| C—Ome | Et | H | F | Me | H | H | Me | H |
| C—Me | Et | H | F | Me | H | H | Me | H |
| N | tBu | H | F | Me | H | H | Me | H |
| CH | tBu | H | F | Me | H | H | Me | H |
| N | 4F—Ph | H | F | Me | H | H | Me | H |
| CH | 4F—Ph | H | F | Me | H | H | Me | H |
| CF | 4F—Ph | H | F | Me | H | H | Me | H |
| C—Cl | 4F—Ph | H | F | Me | H | H | Me | H |
| N | 2,4diFPh | H | F | Me | H | H | Me | H |
| CH | 2,4diFPh | H | F | Me | H | H | Me | H |
| CF | 2,4diFPh | H | F | Me | H | H | Me | H |
| C—Cl | 2,4diFPh | H | F | Me | H | H | Me | H |
| N | Cy | H | F | Me | H | H | Me | Me |
| C—H | Cy | H | F | Me | H | H | Me | Me |
| CF | Cy | H | F | Me | H | H | Me | Me |
| C—Cl | Cy | H | F | Me | H | H | Me | Me |
| C—Ome | Cy | H | F | Me | H | H | Me | Me |
| C—Me | Cy | H | F | Me | H | H | Me | Me |
| N | F—Cy | H | F | Me | H | H | Me | Me |
| C—H | F—Cy | H | F | Me | H | H | Me | Me |
| CF | F—Cy | H | F | Me | H | H | Me | Me |
| C—Cl | F—Cy | H | F | Me | H | H | Me | Me |
| C—Ome | F—Cy | H | F | Me | H | H | Me | Me |
| C—Me | F—Cy | H | F | Me | H | H | Me | Me |
| N | Et | H | F | Me | H | H | Me | Me |
| CH | Et | H | F | Me | H | H | Me | Me |
| CF | Et | H | F | Me | H | H | Me | Me |
| C—Cl | Et | H | F | Me | H | H | Me | Me |
| C—Ome | Et | H | F | Me | H | H | Me | Me |
| C—Me | Et | H | F | Me | H | H | Me | Me |
| N | tBu | H | F | Me | H | H | Me | Me |
| CH | tBu | H | F | Me | H | H | Me | Me |
| N | 4F—Ph | H | F | Me | H | H | Me | Me |
| CH | 4F—Ph | H | F | Me | H | H | Me | Me |
| CF | 4F—Ph | H | F | Me | H | H | Me | Me |
| C—Cl | 4F—Ph | H | F | Me | H | H | Me | Me |
| N | 2,4diFPh | H | F | Me | H | H | Me | Me |
| CH | 2,4diFPh | H | F | Me | H | H | Me | Me |
| CF | 2,4diFPh | H | F | Me | H | H | Me | Me |
| C—Cl | 2,4diFPh | H | F | Me | H | H | Me | Me |

Table III contains compounds of Formula (C).

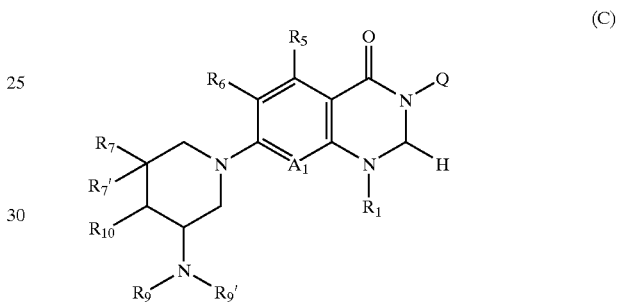

These compounds are those of Formula (I) where X is carbon, Y is —N9(R1)-, a is a double bond, b is a single bond, c is a single bond, and R2 is a double bond oxygen.

| A1 | R1 | R5 | R6 | R7 | R7' | R10 | R9 | R9' | Q |
|---|---|---|---|---|---|---|---|---|---|
| N | Cy | H | F | Me | H | H | H | H | NH$_2$ |
| C—H | Cy | H | F | Me | H | H | H | H | NH$_2$ |
| CF | Cy | H | F | Me | H | H | H | H | NH$_2$ |
| C—Cl | Cy | H | F | Me | H | H | H | H | NH$_2$ |
| C—Ome | Cy | H | F | Me | H | H | H | H | NH$_2$ |
| C—Me | Cy | H | F | Me | H | H | H | H | NH$_2$ |
| N | F—Cy | H | F | Me | H | H | H | H | NH$_2$ |
| C—H | F—Cy | H | F | Me | H | H | H | H | NH$_2$ |
| CF | F—Cy | H | F | Me | H | H | H | H | NH$_2$ |
| C—Cl | F—Cy | H | F | Me | H | H | H | H | NH$_2$ |
| C—Ome | F—Cy | H | F | Me | H | H | H | H | NH$_2$ |
| C—Me | F—Cy | H | F | Me | H | H | H | H | NH$_2$ |
| N | Et | H | F | Me | H | H | H | H | NH$_2$ |
| CH | Et | H | F | Me | H | H | H | H | NH$_2$ |
| CF | Et | H | F | Me | H | H | H | H | NH$_2$ |
| C—Cl | Et | H | F | Me | H | H | H | H | NH$_2$ |
| C—Ome | Et | H | F | Me | H | H | H | H | NH$_2$ |
| C—Me | Et | H | F | Me | H | H | H | H | NH$_2$ |
| N | tBu | H | F | Me | H | H | H | H | NH$_2$ |
| CH | tBu | H | F | Me | H | H | H | H | NH$_2$ |
| N | 4F—Ph | H | F | Me | H | H | H | H | NH$_2$ |
| CH | 4F—Ph | H | F | Me | H | H | H | H | NH$_2$ |
| CF | 4F—Ph | H | F | Me | H | H | H | H | NH$_2$ |
| C—Cl | 4F—Ph | H | F | Me | H | H | H | H | NH$_2$ |
| N | 2,4diFPh | H | F | Me | H | H | H | H | NH$_2$ |
| CH | 2,4diFPh | H | F | Me | H | H | H | H | NH$_2$ |
| CF | 2,4diFPh | H | F | Me | H | H | H | H | NH$_2$ |
| C—Cl | 2,4diFPh | H | F | Me | H | H | H | H | NH$_2$ |
| N | Cy | Me | F | Et | H | H | H | H | NH$_2$ |
| C—H | Cy | Me | F | Et | H | H | H | H | NH$_2$ |

-continued

| A1 | R1 | R5 | R6 | R7 | R7' | R10 | R9 | R9' | Q |
|---|---|---|---|---|---|---|---|---|---|
| CF | Cy | Me | F | Et | H | H | H | H | NH$_2$ |
| C—Cl | Cy | Me | F | Et | H | H | H | H | NH$_2$ |
| C—Ome | Cy | Me | F | Et | H | H | H | H | NH$_2$ |
| C—Me | Cy | Me | F | Et | H | H | H | H | NH$_2$ |
| N | F—Cy | Me | F | Et | H | H | H | H | NH$_2$ |
| C—H | F—Cy | Me | F | Et | H | H | H | H | NH$_2$ |
| CF | F—Cy | Me | F | Et | H | H | H | H | NH$_2$ |
| C—Cl | F—Cy | Me | F | Et | H | H | H | H | NH$_2$ |
| C—Ome | F—Cy | Me | F | Et | H | H | H | H | NH$_2$ |
| C—Me | F—Cy | Me | F | Et | H | H | H | H | NH$_2$ |
| N | Et | Me | F | Et | H | H | H | H | NH$_2$ |
| CH | Et | Me | F | Et | H | H | H | H | NH$_2$ |
| CF | Et | Me | F | Et | H | H | H | H | NH$_2$ |
| C—Cl | Et | Me | F | Et | H | H | H | H | NH$_2$ |
| C—Ome | Et | Me | F | Et | H | H | H | H | NH$_2$ |
| C—Me | Et | Me | F | Et | H | H | H | H | NH$_2$ |
| N | tBu | Me | F | Et | H | H | H | H | NH$_2$ |
| CH | tBu | Me | F | Et | H | H | H | H | NH$_2$ |
| N | 4F—Ph | Me | F | Et | H | H | H | H | NH$_2$ |
| CH | 4F—Ph | Me | F | Et | H | H | H | H | NH$_2$ |
| CF | 4F—Ph | Me | F | Et | H | H | H | H | NH$_2$ |
| C—Cl | 4F—Ph | Me | F | Et | H | H | H | H | NH$_2$ |
| N | 2,4diFPh | Me | F | Et | H | H | H | H | NH$_2$ |
| CH | 2,4diFPh | Me | F | Et | H | H | H | H | NH$_2$ |
| CF | 2,4diFPh | Me | F | Et | H | H | H | H | NH$_2$ |
| C—Cl | 2,4diFPh | Me | F | Et | H | H | H | H | NH$_2$ |
| N | Cy | H | F | OMe | H | H | H | H | NH$_2$ |
| C—H | Cy | H | F | OMe | H | H | H | H | NH$_2$ |
| CF | Cy | H | F | OMe | H | H | H | H | NH$_2$ |
| C—Cl | Cy | H | F | OMe | H | H | H | H | NH$_2$ |
| C—Ome | Cy | H | F | OMe | H | H | H | H | NH$_2$ |
| C—Me | Cy | H | F | OMe | H | H | H | H | NH$_2$ |
| N | F—Cy | H | F | OMe | H | H | H | H | NH$_2$ |
| C—H | F—Cy | H | F | OMe | H | H | H | H | NH$_2$ |
| CF | F—Cy | H | F | OMe | H | H | H | H | NH$_2$ |
| C—Cl | F—Cy | H | F | OMe | H | H | H | H | NH$_2$ |
| C—Ome | F—Cy | H | F | OMe | H | H | H | H | NH$_2$ |
| C—Me | F—Cy | H | F | OMe | H | H | H | H | NH$_2$ |
| N | Et | H | F | OMe | H | H | H | H | NH$_2$ |
| CH | Et | H | F | OMe | H | H | H | H | NH$_2$ |
| CF | Et | H | F | OMe | H | H | H | H | NH$_2$ |
| C—Cl | Et | H | F | OMe | H | H | H | H | NH$_2$ |
| C—Ome | Et | H | F | OMe | H | H | H | H | NH$_2$ |
| C—Me | Et | H | F | OMe | H | H | H | H | NH$_2$ |
| N | tBu | H | F | OMe | H | H | H | H | NH$_2$ |
| CH | tBu | H | F | OMe | H | H | H | H | NH$_2$ |
| N | 4F—Ph | H | F | OMe | H | H | H | H | NH$_2$ |
| CH | 4F—Ph | H | F | OMe | H | H | H | H | NH$_2$ |
| CF | 4F—Ph | H | F | OMe | H | H | H | H | NH$_2$ |
| C—Cl | 4F—Ph | H | F | OMe | H | H | H | H | NH$_2$ |
| N | 2,4diFPh | H | F | OMe | H | H | H | H | NH$_2$ |
| CH | 2,4diFPh | H | F | OMe | H | H | H | H | NH$_2$ |
| CF | 2,4diFPh | H | F | OMe | H | H | H | H | NH$_2$ |
| C—Cl | 2,4diFPh | H | F | OMe | H | H | H | H | NH$_2$ |
| N | Cy | H | F | CH$_2$F | H | H | H | H | NH$_2$ |
| C—H | Cy | H | F | CH$_2$F | H | H | H | H | NH$_2$ |
| CF | Cy | H | F | CH$_2$F | H | H | H | H | NH$_2$ |
| C—Cl | Cy | H | F | CH$_2$F | H | H | H | H | NH$_2$ |
| C—Ome | Cy | H | F | CH$_2$F | H | H | H | H | NH$_2$ |
| C—Me | Cy | H | F | CH$_2$F | H | H | H | H | NH$_2$ |
| N | F—Cy | H | F | CH$_2$F | H | H | H | H | NH$_2$ |
| C—H | F—Cy | H | F | CH$_2$F | H | H | H | H | NH$_2$ |
| CF | F—Cy | H | F | CH$_2$F | H | H | H | H | NH$_2$ |
| C—Cl | F—Cy | H | F | CH$_2$F | H | H | H | H | NH$_2$ |
| C—Ome | F—Cy | H | F | CH$_2$F | H | H | H | H | NH$_2$ |
| C—Me | F—Cy | H | F | CH$_2$F | H | H | H | H | NH$_2$ |
| N | Et | H | F | CH$_2$F | H | H | H | H | NH$_2$ |
| CH | Et | H | F | CH$_2$F | H | H | H | H | NH$_2$ |
| CF | Et | H | F | CH$_2$F | H | H | H | H | NH$_2$ |
| C—Cl | Et | H | F | CH$_2$F | H | H | H | H | NH$_2$ |
| C—Ome | Et | H | F | CH$_2$F | H | H | H | H | NH$_2$ |
| C—Me | Et | H | F | CH$_2$F | H | H | H | H | NH$_2$ |
| N | tBu | H | F | CH$_2$F | H | H | H | H | NH$_2$ |
| CH | tBu | H | F | CH$_2$F | H | H | H | H | NH$_2$ |
| N | 4F—Ph | H | F | CH$_2$F | H | H | H | H | NH$_2$ |
| CH | 4F—Ph | H | F | CH$_2$F | H | H | H | H | NH$_2$ |
| CF | 4F—Ph | H | F | CH$_2$F | H | H | H | H | NH$_2$ |
| C—Cl | 4F—Ph | H | F | CH$_2$F | H | H | H | H | NH$_2$ |
| N | 2,4diFPh | H | F | CH$_2$F | H | H | H | H | NH$_2$ |
| CH | 2,4diFPh | H | F | CH$_2$F | H | H | H | H | NH$_2$ |
| CF | 2,4diFPh | H | F | CH$_2$F | H | H | H | H | NH$_2$ |
| C—Cl | 2,4diFPh | H | F | CH$_2$F | H | H | H | H | NH$_2$ |
| N | Cy | H | F | Me | Me | H | H | H | NH$_2$ |
| C—H | Cy | H | F | Me | Me | H | H | H | NH$_2$ |
| CF | Cy | H | F | Me | Me | H | H | H | NH$_2$ |
| C—Cl | Cy | H | F | Me | Me | H | H | H | NH$_2$ |
| C—Ome | Cy | H | F | Me | Me | H | H | H | NH$_2$ |
| C—Me | Cy | H | F | Me | Me | H | H | H | NH$_2$ |
| N | F—Cy | H | F | Me | Me | H | H | H | NH$_2$ |
| C—H | F—Cy | H | F | Me | Me | H | H | H | NH$_2$ |
| CF | F—Cy | H | F | Me | Me | H | H | H | NH$_2$ |
| C—Cl | F—Cy | H | F | Me | Me | H | H | H | NH$_2$ |
| C—Ome | F—Cy | H | F | Me | Me | H | H | H | NH$_2$ |
| C—Me | F—Cy | H | F | Me | Me | H | H | H | NH$_2$ |
| N | Et | H | F | Me | Me | H | H | H | NH$_2$ |
| CH | Et | H | F | Me | Me | H | H | H | NH$_2$ |
| CF | Et | H | F | Me | Me | H | H | H | NH$_2$ |
| C—Cl | Et | H | F | Me | Me | H | H | H | NH$_2$ |
| C—Ome | Et | H | F | Me | Me | H | H | H | NH$_2$ |
| C—Me | Et | H | F | Me | Me | H | H | H | NH$_2$ |
| N | tBu | H | F | Me | Me | H | H | H | NH$_2$ |
| CH | tBu | H | F | Me | Me | H | H | H | NH$_2$ |
| N | 4F—Ph | H | F | Me | Me | H | H | H | NH$_2$ |
| CH | 4F—Ph | H | F | Me | Me | H | H | H | NH$_2$ |
| CF | 4F—Ph | H | F | Me | Me | H | H | H | NH$_2$ |
| C—Cl | 4F—Ph | H | F | Me | Me | H | H | H | NH$_2$ |
| N | 2,4diFPh | H | F | Me | Me | H | H | H | NH$_2$ |
| CH | 2,4diFPh | H | F | Me | Me | H | H | H | NH$_2$ |
| CF | 2,4diFPh | H | F | Me | Me | H | H | H | NH$_2$ |
| C—Cl | 2,4diFPh | H | F | Me | Me | H | H | H | NH$_2$ |
| N | Cy | H | F | Me | H | Me | H | H | NH$_2$ |
| C—H | Cy | H | F | Me | H | Me | H | H | NH$_2$ |
| CF | Cy | H | F | Me | H | Me | H | H | NH$_2$ |
| C—Cl | Cy | H | F | Me | H | Me | H | H | NH$_2$ |
| C—Ome | Cy | H | F | Me | H | Me | H | H | NH$_2$ |
| C—Me | Cy | H | F | Me | H | Me | H | H | NH$_2$ |
| N | F—Cy | H | F | Me | H | Me | H | H | NH$_2$ |
| C—H | F—Cy | H | F | Me | H | Me | H | H | NH$_2$ |
| CF | F—Cy | H | F | Me | H | Me | H | H | NH$_2$ |
| C—Cl | F—Cy | H | F | Me | H | Me | H | H | NH$_2$ |
| C—Ome | F—Cy | H | F | Me | H | Me | H | H | NH$_2$ |
| C—Me | F—Cy | H | F | Me | H | Me | H | H | NH$_2$ |
| N | Et | H | F | Me | H | Me | H | H | NH$_2$ |
| CH | Et | H | F | Me | H | Me | H | H | NH$_2$ |
| CF | Et | H | F | Me | H | Me | H | H | NH$_2$ |
| C—Cl | Et | H | F | Me | H | Me | H | H | NH$_2$ |
| C—Ome | Et | H | F | Me | H | Me | H | H | NH$_2$ |
| C—Me | Et | H | F | Me | H | Me | H | H | NH$_2$ |
| N | tBu | H | F | Me | H | Me | H | H | NH$_2$ |
| CH | tBu | H | F | Me | H | Me | H | H | NH$_2$ |
| N | 4F—Ph | H | F | Me | H | Me | H | H | NH$_2$ |
| CH | 4F—Ph | H | F | Me | H | Me | H | H | NH$_2$ |
| CF | 4F—Ph | H | F | Me | H | Me | H | H | NH$_2$ |
| C—Cl | 4F—Ph | H | F | Me | H | Me | H | H | NH$_2$ |
| N | 2,4diFPh | H | F | Me | H | Me | H | H | NH$_2$ |
| CH | 2,4diFPh | H | F | Me | H | Me | H | H | NH$_2$ |
| CF | 2,4diFPh | H | F | Me | H | Me | H | H | NH$_2$ |
| C—Cl | 2,4diFPh | H | F | Me | H | Me | H | H | NH$_2$ |
| N | Cy | H | F | Me | H | Et | H | H | NH$_2$ |
| C—H | Cy | H | F | Me | H | Et | H | H | NH$_2$ |
| CF | Cy | H | F | Me | H | Et | H | H | NH$_2$ |
| C—Cl | Cy | H | F | Me | H | Et | H | H | NH$_2$ |
| C—Ome | Cy | H | F | Me | H | Et | H | H | NH$_2$ |
| C—Me | Cy | H | F | Me | H | Et | H | H | NH$_2$ |
| N | F—Cy | H | F | Me | H | Et | H | H | NH$_2$ |
| C—H | F—Cy | H | F | Me | H | Et | H | H | NH$_2$ |
| CF | F—Cy | H | F | Me | H | Et | H | H | NH$_2$ |
| C—Cl | F—Cy | H | F | Me | H | Et | H | H | NH$_2$ |
| C—Ome | F—Cy | H | F | Me | H | Et | H | H | NH$_2$ |
| C—Me | F—Cy | H | F | Me | H | Et | H | H | NH$_2$ |
| N | Et | H | F | Me | H | Et | H | H | NH$_2$ |
| CH | Et | H | F | Me | H | Et | H | H | NH$_2$ |
| CF | Et | H | F | Me | H | Et | H | H | NH$_2$ |
| C—Cl | Et | H | F | Me | H | Et | H | H | NH$_2$ |

| A1 | R1 | R5 | R6 | R7 | R7' | R10 | R9 | R9' | Q |
|---|---|---|---|---|---|---|---|---|---|
| C—Ome | Et | H | F | Me | H | Et | H | H | NH₂ |
| C—Me | Et | H | F | Me | H | Et | H | H | NH₂ |
| N | tBu | H | F | Me | H | Et | H | H | NH₂ |
| CH | tBu | H | F | Me | H | Et | H | H | NH₂ |
| N | 4F—Ph | H | F | Me | H | Et | H | H | NH₂ |
| CH | 4F—Ph | H | F | Me | H | Et | H | H | NH₂ |
| CF | 4F—Ph | H | F | Me | H | Et | H | H | NH₂ |
| C—Cl | 4F—Ph | H | F | Me | H | Et | H | H | NH₂ |
| N | 2,4diFPh | H | F | Me | H | Et | H | H | NH₂ |
| CH | 2,4diFPh | H | F | Me | H | Et | H | H | NH₂ |
| CF | 2,4diFPh | H | F | Me | H | Et | H | H | NH₂ |
| C—Cl | 2,4diFPh | H | F | Me | H | Et | H | H | NH₂ |
| N | Cy | H | F | Me | H | H | Me | H | NH₂ |
| C—H | Cy | H | F | Me | H | H | Me | H | NH₂ |
| CF | Cy | H | F | Me | H | H | Me | H | NH₂ |
| C—Cl | Cy | H | F | Me | H | H | Me | H | NH₂ |
| C—Ome | Cy | H | F | Me | H | H | Me | H | NH₂ |
| C—Me | Cy | H | F | Me | H | H | Me | H | NH₂ |
| N | F—Cy | H | F | Me | H | H | Me | H | NH₂ |
| C—H | F—Cy | H | F | Me | H | H | Me | H | NH₂ |
| CF | F—Cy | H | F | Me | H | H | Me | H | NH₂ |
| C—Cl | F—Cy | H | F | Me | H | H | Me | H | NH₂ |
| C—Ome | F—Cy | H | F | Me | H | H | Me | H | NH₂ |
| C—Me | F—Cy | H | F | Me | H | H | Me | H | NH₂ |
| N | Et | H | F | Me | H | H | Me | H | NH₂ |
| CH | Et | H | F | Me | H | H | Me | H | NH₂ |
| CF | Et | H | F | Me | H | H | Me | H | NH₂ |
| C—Cl | Et | H | F | Me | H | H | Me | H | NH₂ |
| C—Ome | Et | H | F | Me | H | H | Me | H | NH₂ |
| C—Me | Et | H | F | Me | H | H | Me | H | NH₂ |
| N | tBu | H | F | Me | H | H | Me | H | NH₂ |
| CH | tBu | H | F | Me | H | H | Me | H | NH₂ |
| N | 4F—Ph | H | F | Me | H | H | Me | H | NH₂ |
| CH | 4F—Ph | H | F | Me | H | H | Me | H | NH₂ |
| CF | 4F—Ph | H | F | Me | H | H | Me | H | NH₂ |
| C—Cl | 4F—Ph | H | F | Me | H | H | Me | H | NH₂ |
| N | 2,4diFPh | H | F | Me | H | H | Me | H | NH₂ |
| CH | 2,4diFPh | H | F | Me | H | H | Me | H | NH₂ |
| CF | 2,4diFPh | H | F | Me | H | H | Me | H | NH₂ |
| C—Cl | 2,4diFPh | H | F | Me | H | H | Me | H | NH₂ |
| N | Cy | H | F | Me | H | H | Me | Me | NH₂ |
| C—H | Cy | H | F | Me | H | H | Me | Me | NH₂ |
| CF | Cy | H | F | Me | H | H | Me | Me | NH₂ |
| C—Cl | Cy | H | F | Me | H | H | Me | Me | NH₂ |
| C—Ome | Cy | H | F | Me | H | H | Me | Me | NH₂ |
| C—Me | Cy | H | F | Me | H | H | Me | Me | NH₂ |
| N | F—Cy | H | F | Me | H | H | Me | Me | NH₂ |
| C—H | F—Cy | H | F | Me | H | H | Me | Me | NH₂ |
| CF | F—Cy | H | F | Me | H | H | Me | Me | NH₂ |
| C—Cl | F—Cy | H | F | Me | H | H | Me | Me | NH₂ |
| C—Ome | F—Cy | H | F | Me | H | H | Me | Me | NH₂ |
| C—Me | F—Cy | H | F | Me | H | H | Me | Me | NH₂ |
| N | Et | H | F | Me | H | H | Me | Me | NH₂ |
| CH | Et | H | F | Me | H | H | Me | Me | NH₂ |
| CF | Et | H | F | Me | H | H | Me | Me | NH₂ |
| C—Cl | Et | H | F | Me | H | H | Me | Me | NH₂ |
| C—Ome | Et | H | F | Me | H | H | Me | Me | NH₂ |
| C—Me | Et | H | F | Me | H | H | Me | Me | NH₂ |
| N | tBu | H | F | Me | H | H | Me | Me | NH₂ |
| CH | tBu | H | F | Me | H | H | Me | Me | NH₂ |
| N | 4F—Ph | H | F | Me | H | H | Me | Me | NH₂ |
| CH | 4F—Ph | H | F | Me | H | H | Me | Me | NH₂ |
| CF | 4F—Ph | H | F | Me | H | H | Me | Me | NH₂ |
| C—Cl | 4F—Ph | H | F | Me | H | H | Me | Me | NH₂ |
| N | 2,4diFPh | H | F | Me | H | H | Me | Me | NH₂ |
| CH | 2,4diFPh | H | F | Me | H | H | Me | Me | NH₂ |
| CF | 2,4diFPh | H | F | Me | H | H | Me | Me | NH₂ |
| C—Cl | 2,4diFPh | H | F | Me | H | H | Me | Me | NH₂ |
| N | Cy | H | F | Me | H | H | H | H | OH |
| C—H | Cy | H | F | Me | H | H | H | H | OH |
| CF | Cy | H | F | Me | H | H | H | H | OH |
| C—Cl | Cy | H | F | Me | H | H | H | H | OH |
| C—Ome | Cy | H | F | Me | H | H | H | H | OH |
| C—Me | Cy | H | F | Me | H | H | H | H | OH |
| N | F—Cy | H | F | Me | H | H | H | H | OH |
| C—H | F—Cy | H | F | Me | H | H | H | H | OH |
| CF | F—Cy | H | F | Me | H | H | H | H | OH |
| C—Cl | F—Cy | H | F | Me | H | H | H | H | OH |
| C—Ome | F—Cy | H | F | Me | H | H | H | H | OH |
| C—Me | F—Cy | H | F | Me | H | H | H | H | OH |
| N | Et | H | F | Me | H | H | H | H | OH |
| CH | Et | H | F | Me | H | H | H | H | OH |
| CF | Et | H | F | Me | H | H | H | H | OH |
| C—Cl | Et | H | F | Me | H | H | H | H | OH |
| C—Ome | Et | H | F | Me | H | H | H | H | OH |
| C—Me | Et | H | F | Me | H | H | H | H | OH |
| N | tBu | H | F | Me | H | H | H | H | OH |
| CH | tBu | H | F | Me | H | H | H | H | OH |
| N | 4F—Ph | H | F | Me | H | H | H | H | OH |
| CH | 4F—Ph | H | F | Me | H | H | H | H | OH |
| CF | 4F—Ph | H | F | Me | H | H | H | H | OH |
| C—Cl | 4F—Ph | H | F | Me | H | H | H | H | OH |
| N | 2,4diFPh | H | F | Me | H | H | H | H | OH |
| CH | 2,4diFPh | H | F | Me | H | H | H | H | OH |
| CF | 2,4diFPh | H | F | Me | H | H | H | H | OH |
| C—Cl | 2,4diFPh | H | F | Me | H | H | H | H | OH |
| N | Cy | Me | F | Et | H | H | H | H | OH |
| C—H | Cy | Me | F | Et | H | H | H | H | OH |
| CF | Cy | Me | F | Et | H | H | H | H | OH |
| C—Cl | Cy | Me | F | Et | H | H | H | H | OH |
| C—Ome | Cy | Me | F | Et | H | H | H | H | OH |
| C—Me | Cy | Me | F | Et | H | H | H | H | OH |
| N | F—Cy | Me | F | Et | H | H | H | H | OH |
| C—H | F—Cy | Me | F | Et | H | H | H | H | OH |
| CF | F—Cy | Me | F | Et | H | H | H | H | OH |
| C—Cl | F—Cy | Me | F | Et | H | H | H | H | OH |
| C—Ome | F—Cy | Me | F | Et | H | H | H | H | OH |
| C—Me | F—Cy | Me | F | Et | H | H | H | H | OH |
| N | Et | Me | F | Et | H | H | H | H | OH |
| CH | Et | Me | F | Et | H | H | H | H | OH |
| CF | Et | Me | F | Et | H | H | H | H | OH |
| C—Cl | Et | Me | F | Et | H | H | H | H | OH |
| C—Ome | Et | Me | F | Et | H | H | H | H | OH |
| C—Me | Et | Me | F | Et | H | H | H | H | OH |
| N | tBu | Me | F | Et | H | H | H | H | OH |
| CH | tBu | Me | F | Et | H | H | H | H | OH |
| N | 4F—Ph | Me | F | Et | H | H | H | H | OH |
| CH | 4F—Ph | Me | F | Et | H | H | H | H | OH |
| CF | 4F—Ph | Me | F | Et | H | H | H | H | OH |
| C—Cl | 4F—Ph | Me | F | Et | H | H | H | H | OH |
| N | 2,4diFPh | Me | F | Et | H | H | H | H | OH |
| CH | 2,4diFPh | Me | F | Et | H | H | H | H | OH |
| CF | 2,4diFPh | Me | F | Et | H | H | H | H | OH |
| C—Cl | 2,4diFPh | Me | F | Et | H | H | H | H | OH |
| N | Cy | H | F | OMe | H | H | H | H | OH |
| C—H | Cy | H | F | OMe | H | H | H | H | OH |
| CF | Cy | H | F | OMe | H | H | H | H | OH |
| C—Cl | Cy | H | F | OMe | H | H | H | H | OH |
| C—Ome | Cy | H | F | OMe | H | H | H | H | OH |
| C—Me | Cy | H | F | OMe | H | H | H | H | OH |
| N | F—Cy | H | F | OMe | H | H | H | H | OH |
| C—H | F—Cy | H | F | OMe | H | H | H | H | OH |
| CF | F—Cy | H | F | OMe | H | H | H | H | OH |
| C—Cl | F—Cy | H | F | OMe | H | H | H | H | OH |
| C—Ome | F—Cy | H | F | OMe | H | H | H | H | OH |
| C—Me | F—Cy | H | F | OMe | H | H | H | H | OH |
| N | Et | H | F | OMe | H | H | H | H | OH |
| CH | Et | H | F | OMe | H | H | H | H | OH |
| CF | Et | H | F | OMe | H | H | H | H | OH |
| C—Cl | Et | H | F | OMe | H | H | H | H | OH |
| C—Ome | Et | H | F | OMe | H | H | H | H | OH |
| C—Me | Et | H | F | OMe | H | H | H | H | OH |
| N | tBu | H | F | OMe | H | H | H | H | OH |
| CH | tBu | H | F | OMe | H | H | H | H | OH |
| N | 4F—Ph | H | F | OMe | H | H | H | H | OH |
| CH | 4F—Ph | H | F | OMe | H | H | H | H | OH |
| CF | 4F—Ph | H | F | OMe | H | H | H | H | OH |
| C—Cl | 4F—Ph | H | F | OMe | H | H | H | H | OH |
| N | 2,4diFPh | H | F | OMe | H | H | H | H | OH |
| CH | 2,4diFPh | H | F | OMe | H | H | H | H | OH |
| CF | 2,4diFPh | H | F | OMe | H | H | H | H | OH |
| C—Cl | 2,4diFPh | H | F | OMe | H | H | H | H | OH |
| N | Cy | H | F | CH₂F | H | H | H | H | OH |
| C—H | Cy | H | F | CH₂F | H | H | H | H | OH |

-continued

| A1 | R1 | R5 | R6 | R7 | R7' | R10 | R9 | R9' | Q |
|---|---|---|---|---|---|---|---|---|---|
| CF | Cy | H | F | CH$_2$F | H | H | H | H | OH |
| C—Cl | Cy | H | F | CH$_2$F | H | H | H | H | OH |
| C—Ome | Cy | H | F | CH$_2$F | H | H | H | H | OH |
| C—Me | Cy | H | F | CH$_2$F | H | H | H | H | OH |
| N | F—Cy | H | F | CH$_2$F | H | H | H | H | OH |
| C—H | F—Cy | H | F | CH$_2$F | H | H | H | H | OH |
| CF | F—Cy | H | F | CH$_2$F | H | H | H | H | OH |
| C—Cl | F—Cy | H | F | CH$_2$F | H | H | H | H | OH |
| C—Ome | F—Cy | H | F | CH$_2$F | H | H | H | H | OH |
| C—Me | F—Cy | H | F | CH$_2$F | H | H | H | H | OH |
| N | Et | H | F | CH$_2$F | H | H | H | H | OH |
| CH | Et | H | F | CH$_2$F | H | H | H | H | OH |
| CF | Et | H | F | CH$_2$F | H | H | H | H | OH |
| C—Cl | Et | H | F | CH$_2$F | H | H | H | H | OH |
| C—Ome | Et | H | F | CH$_2$F | H | H | H | H | OH |
| C—Me | Et | H | F | CH$_2$F | H | H | H | H | OH |
| N | tBu | H | F | CH$_2$F | H | H | H | H | OH |
| CH | tBu | H | F | CH$_2$F | H | H | H | H | OH |
| N | 4F—Ph | H | F | CH$_2$F | H | H | H | H | OH |
| CH | 4F—Ph | H | F | CH$_2$F | H | H | H | H | OH |
| CF | 4F—Ph | H | F | CH$_2$F | H | H | H | H | OH |
| C—Cl | 4F—Ph | H | F | CH$_2$F | H | H | H | H | OH |
| N | 2,4diFPh | H | F | CH$_2$F | H | H | H | H | OH |
| CH | 2,4diFPh | H | F | CH$_2$F | H | H | H | H | OH |
| CF | 2,4diFPh | H | F | CH$_2$F | H | H | H | H | OH |
| C—Cl | 2,4diFPh | H | F | CH$_2$F | H | H | H | H | OH |
| N | Cy | H | F | Me | Me | H | H | H | OH |
| C—H | Cy | H | F | Me | Me | H | H | H | OH |
| CF | Cy | H | F | Me | Me | H | H | H | OH |
| C—Cl | Cy | H | F | Me | Me | H | H | H | OH |
| C—Ome | Cy | H | F | Me | Me | H | H | H | OH |
| C—Me | Cy | H | F | Me | Me | H | H | H | OH |
| N | F—Cy | H | F | Me | Me | H | H | H | OH |
| C—H | F—Cy | H | F | Me | Me | H | H | H | OH |
| CF | F—Cy | H | F | Me | Me | H | H | H | OH |
| C—Cl | F—Cy | H | F | Me | Me | H | H | H | OH |
| C—Ome | F—Cy | H | F | Me | Me | H | H | H | OH |
| C—Me | F—Cy | H | F | Me | Me | H | H | H | OH |
| N | Et | H | F | Me | Me | H | H | H | OH |
| CH | Et | H | F | Me | Me | H | H | H | OH |
| CF | Et | H | F | Me | Me | H | H | H | OH |
| C—Cl | Et | H | F | Me | Me | H | H | H | OH |
| C—Ome | Et | H | F | Me | Me | H | H | H | OH |
| C—Me | Et | H | F | Me | Me | H | H | H | OH |
| N | tBu | H | F | Me | Me | H | H | H | OH |
| CH | tBU | H | F | Me | Me | H | H | H | OH |
| N | 4F—Ph | H | F | Me | Me | H | H | H | OH |
| CH | 4F—Ph | H | F | Me | Me | H | H | H | OH |
| CF | 4F—Ph | H | F | Me | Me | H | H | H | OH |
| C—Cl | 4F—Ph | H | F | Me | Me | H | H | H | OH |
| N | 2,4diFPh | H | F | Me | Me | H | H | H | OH |
| CH | 2,4diFPh | H | F | Me | Me | H | H | H | OH |
| CF | 2,4diFPh | H | F | Me | Me | H | H | H | OH |
| C—Cl | 2,4diFPh | H | F | Me | Me | H | H | H | OH |
| N | Cy | H | F | Me | H | Me | H | H | OH |
| C—H | Cy | H | F | Me | H | Me | H | H | OH |
| CF | Cy | H | F | Me | H | Me | H | H | OH |
| C—Cl | Cy | H | F | Me | H | Me | H | H | OH |
| C—Ome | Cy | H | F | Me | H | Me | H | H | OH |
| C—Me | Cy | H | F | Me | H | Me | H | H | OH |
| N | F—Cy | H | F | Me | H | Me | H | H | OH |
| C—H | F—Cy | H | F | Me | H | Me | H | H | OH |
| CF | F—Cy | H | F | Me | H | Me | H | H | OH |
| C—Cl | F—Cy | H | F | Me | H | Me | H | H | OH |
| C—Ome | F—Cy | H | F | Me | H | Me | H | H | OH |
| C—Me | F—Cy | H | F | Me | H | Me | H | H | OH |
| N | Et | H | F | Me | H | Me | H | H | OH |
| CH | Et | H | F | Me | H | Me | H | H | OH |
| CF | Et | H | F | Me | H | Me | H | H | OH |
| C—Cl | Et | H | F | Me | H | Me | H | H | OH |
| C—Ome | Et | H | F | Me | H | Me | H | H | OH |
| C—Me | Et | H | F | Me | H | Me | H | H | OH |
| N | tBu | H | F | Me | H | Me | H | H | OH |
| CH | tBu | H | F | Me | H | Me | H | H | OH |
| N | 4F—Ph | H | F | Me | H | Me | H | H | OH |
| CH | 4F—Ph | H | F | Me | H | Me | H | H | OH |
| CF | 4F—Ph | H | F | Me | H | Me | H | H | OH |
| C—Cl | 4F—Ph | H | F | Me | H | Me | H | H | OH |
| N | 2,4diFPh | H | F | Me | H | Me | H | H | OH |
| CH | 2,4diFPh | H | F | Me | H | Me | H | H | OH |
| CF | 2,4diFPh | H | F | Me | H | Me | H | H | OH |
| C—Cl | 2,4diFPh | H | F | Me | H | Me | H | H | OH |
| N | Cy | H | F | Me | H | Et | H | H | OH |
| C—H | Cy | H | F | Me | H | Et | H | H | OH |
| CF | Cy | H | F | Me | H | Et | H | H | OH |
| C—Cl | Cy | H | F | Me | H | Et | H | H | OH |
| C—Ome | Cy | H | F | Me | H | Et | H | H | OH |
| C—Me | Cy | H | F | Me | H | Et | H | H | OH |
| N | F—Cy | H | F | Me | H | Et | H | H | OH |
| C—H | F—Cy | H | F | Me | H | Et | H | H | OH |
| CF | F—Cy | H | F | Me | H | Et | H | H | OH |
| C—Cl | F—Cy | H | F | Me | H | Et | H | H | OH |
| C—Ome | F—Cy | H | F | Me | H | Et | H | H | OH |
| C—Me | F—Cy | H | F | Me | H | Et | H | H | OH |
| N | Et | H | F | Me | H | Et | H | H | OH |
| CH | Et | H | F | Me | H | Et | H | H | OH |
| CF | Et | H | F | Me | H | Et | H | H | OH |
| C—Cl | Et | H | F | Me | H | Et | H | H | OH |
| C—Ome | Et | H | F | Me | H | Et | H | H | OH |
| C—Me | Et | H | F | Me | H | Et | H | H | OH |
| N | tBu | H | F | Me | H | Et | H | H | OH |
| CH | tBu | H | F | Me | H | Et | H | H | OH |
| N | 4F—Ph | H | F | Me | H | Et | H | H | OH |
| CH | 4F—Ph | H | F | Me | H | Et | H | H | OH |
| CF | 4F—Ph | H | F | Me | H | Et | H | H | OH |
| C—Cl | 4F—Ph | H | F | Me | H | Et | H | H | OH |
| N | 2,4diFPh | H | F | Me | H | Et | H | H | OH |
| CH | 2,4diFPh | H | F | Me | H | Et | H | H | OH |
| CF | 2,4diFPh | H | F | Me | H | Et | H | H | OH |
| C—Cl | 2,4diFPh | H | F | Me | H | Et | H | H | OH |
| N | Cy | H | F | Me | H | H | Me | H | OH |
| C—H | Cy | H | F | Me | H | H | Me | H | OH |
| CF | Cy | H | F | Me | H | H | Me | H | OH |
| C—Cl | Cy | H | F | Me | H | H | Me | H | OH |
| C—Ome | Cy | H | F | Me | H | H | Me | H | OH |
| C—Me | Cy | H | F | Me | H | H | Me | H | OH |
| N | F—Cy | H | F | Me | H | H | Me | H | OH |
| C—H | F—Cy | H | F | Me | H | H | Me | H | OH |
| CF | F—Cy | H | F | Me | H | H | Me | H | OH |
| C—Cl | F—Cy | H | F | Me | H | H | Me | H | OH |
| C—Ome | F—Cy | H | F | Me | H | H | Me | H | OH |
| C—Me | F—Cy | H | F | Me | H | H | Me | H | OH |
| N | Et | H | F | Me | H | H | Me | H | OH |
| CH | Et | H | F | Me | H | H | Me | H | OH |
| CF | Et | H | F | Me | H | H | Me | H | OH |
| C—Cl | Et | H | F | Me | H | H | Me | H | OH |
| C—Ome | Et | H | F | Me | H | H | Me | H | OH |
| C—Me | Et | H | F | Me | H | H | Me | H | OH |
| N | tBu | H | F | Me | H | H | Me | H | OH |
| CH | tBu | H | F | Me | H | H | Me | H | OH |
| N | 4F—Ph | H | F | Me | H | H | Me | H | OH |
| CH | 4F—Ph | H | F | Me | H | H | Me | H | OH |
| CF | 4F—Ph | H | F | Me | H | H | Me | H | OH |
| C—Cl | 4F—Ph | H | F | Me | H | H | Me | H | OH |
| N | 2,4diFPh | H | F | Me | H | H | Me | H | OH |
| CH | 2,4diFPh | H | F | Me | H | H | Me | H | OH |
| CF | 2,4diFPh | H | F | Me | H | H | Me | H | OH |
| C—Cl | 2,4diFPh | H | F | Me | H | H | Me | H | OH |
| N | Cy | H | F | Me | H | H | Me | Me | OH |
| C—H | Cy | H | F | Me | H | H | Me | Me | OH |
| CF | Cy | H | F | Me | H | H | Me | Me | OH |
| C—Cl | Cy | H | F | Me | H | H | Me | Me | OH |
| C—Ome | Cy | H | F | Me | H | H | Me | Me | OH |
| C—Me | Cy | H | F | Me | H | H | Me | Me | OH |
| N | F—Cy | H | F | Me | H | H | Me | Me | OH |
| C—H | F—Cy | H | F | Me | H | H | Me | Me | OH |
| CF | F—Cy | H | F | Me | H | H | Me | Me | OH |
| C—Cl | F—Cy | H | F | Me | H | H | Me | Me | OH |
| C—Ome | F—Cy | H | F | Me | H | H | Me | Me | OH |
| C—Me | F—Cy | H | F | Me | H | H | Me | Me | OH |
| N | Et | H | F | Me | H | H | Me | Me | OH |
| CH | Et | H | F | Me | H | H | Me | Me | OH |
| CF | Et | H | F | Me | H | H | Me | Me | OH |
| C—Cl | Et | H | F | Me | H | H | Me | Me | OH |

-continued

| A1 | R1 | R5 | R6 | R7 | R7' | R10 | R9 | R9' | Q |
|---|---|---|---|---|---|---|---|---|---|
| C—Ome | Et | H | F | Me | H | H | Me | Me | OH |
| C—Me | Et | H | F | Me | H | H | Me | Me | OH |
| N | tBu | H | F | Me | H | H | Me | Me | OH |
| CH | tBu | H | F | Me | H | H | Me | Me | OH |
| N | 4F—Ph | H | F | Me | H | H | Me | Me | OH |
| CH | 4F—Ph | H | F | Me | H | H | Me | Me | OH |
| CF | 4F—Ph | H | F | Me | H | H | Me | Me | OH |
| C—Cl | 4F—Ph | H | F | Me | H | H | Me | Me | OH |
| N | 2,4diFPh | H | F | Me | H | H | Me | Me | OH |
| CH | 2,4diFPh | H | F | Me | H | H | Me | Me | OH |
| CF | 2,4diFPh | H | F | Me | H | H | Me | Me | OH |
| C—Cl | 2,4diFPh | H | F | Me | H | H | Me | Me | OH |

Table IV contains a non-limiting list of compounds according to Formula (D).

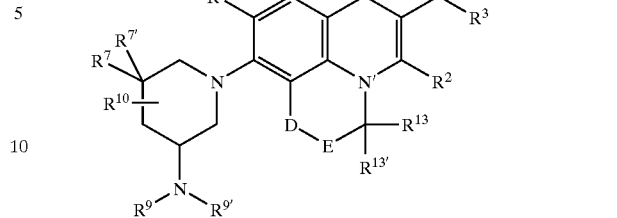

(D)

These compounds are those of Formula (I) where Z is —C(COR3)-, $R^1$ and $R^8$ join to form a 6-membered heterocycloalkyl. Formula (D) is defined such that D is substituted or unsubstituted —C— or —N— or D is —O— or S; $R^{13}$ and $R^{13'}$ are independently selected from hydrogen and C1–C6 alkyl; and E is selected from —O—, —S—, substituted or unsubstituted —C— and substituted or unsubstituted —N—. In one embodiment, D is —O—. In one embodiment, E is —CH$_2$—. In one embodiment, $R^{13}$ is hydrogen and $R^{13'}$ is C1–C6 alkyl, preferably methyl.

Table V contains a non-limiting list of preferred compounds of Formula (D).

TABLE V

| $R^2$ | $R^3$ | $R^5$ | $R^6$ | $R^7$ | $R^{7'}$ | $R^9$ | $R^{9'}$ | Each $R^{10}$ | $R^{13}$ | $R^{13'}$ | E | D |
|---|---|---|---|---|---|---|---|---|---|---|---|---|
| H | OH | H | F | Me | H | H | H | H | Me | H | CH$_2$ | O |
| H | OH | H | Cl | Me | H | H | H | H | Me | H | CH$_2$ | O |
| H | OH | NH$_2$ | F | Me | H | H | H | H | Me | H | CH$_2$ | O |
| H | OH | Me | F | Me | H | H | H | H | Me | H | CH$_2$ | O |
| H | OH | H | F | Me | H | H | H | H | Me | H | CH$_2$ | S |
| H | OH | NH$_2$ | F | Me | H | H | H | H | Me | H | CH$_2$ | S |
| H | OH | Me | F | Me | H | H | H | H | Me | H | CH$_2$ | S |
| H | OH | H | F | Me | H | Me | H | H | Me | H | CH$_2$ | O |
| H | OH | NH$_2$ | F | Me | H | Me | H | H | Me | H | CH$_2$ | O |
| H | OH | Me | F | Me | H | Me | H | H | Me | H | CH$_2$ | O |
| H | OH | H | F | Me | H | Me | H | H | Me | H | CH$_2$ | S |
| H | OH | NH$_2$ | F | Me | H | Me | H | H | Me | H | CH$_2$ | S |
| H | OH | Me | F | Me | H | Me | H | H | Me | H | CH$_2$ | S |
| H | OH | H | F | Me | H | H | H | H | Me | H | CH$_2$ | O |
| H | OH | H | Cl | Me | H | H | H | H | Me | H | CH$_2$ | O |
| H | OH | NH$_2$ | F | Me | H | H | H | H | Me | H | CH$_2$ | O |
| H | OH | Me | F | Me | H | H | H | H | Me | H | CH$_2$ | O |
| H | OH | H | F | Me | H | H | H | H | Me | H | CH$_2$ | S |
| H | OH | NH$_2$ | F | Me | H | H | H | H | Me | H | CH$_2$ | S |
| H | OH | Me | F | Me | H | H | H | H | Me | H | CH$_2$ | S |
| H | OH | H | F | Me | H | Me | H | H | Me | H | CH$_2$ | O |
| H | OH | NH$_2$ | F | Me | H | Me | H | H | Me | H | CH$_2$ | O |
| H | OH | Me | F | Me | H | Me | H | H | Me | H | CH$_2$ | O |
| H | OH | H | F | Me | H | Me | H | H | Me | H | CH$_2$ | S |
| H | OH | NH$_2$ | F | Me | H | Me | H | H | Me | H | CH$_2$ | S |
| H | OH | Me | F | Me | H | Me | H | H | Me | H | CH$_2$ | S |
| H | OH | H | F | Me | H | H | H | H | Me | H | CH$_2$ | O |
| H | OH | H | Cl | Me | H | H | H | H | Me | H | CH$_2$ | O |
| H | OH | NH$_2$ | F | Me | H | H | H | H | Me | H | CH$_2$ | O |
| H | OH | Me | F | Me | H | H | H | H | Me | H | CH$_2$ | O |
| H | OH | H | F | Me | H | H | H | H | Me | H | CH$_2$ | S |
| H | OH | NH$_2$ | F | Me | H | H | H | H | Me | H | CH$_2$ | S |
| H | OH | Me | F | Me | H | H | H | H | Me | H | CH$_2$ | S |
| H | OH | H | F | Me | H | Me | H | H | Me | H | CH$_2$ | O |
| H | OH | NH$_2$ | F | Me | H | Me | H | H | Me | H | CH$_2$ | O |
| H | OH | Me | F | Me | H | Me | H | H | Me | H | CH$_2$ | O |
| H | OH | H | F | Me | H | Me | H | H | Me | H | CH$_2$ | S |
| H | OH | NH$_2$ | F | Me | H | Me | H | H | Me | H | CH$_2$ | S |
| H | OH | Me | F | Me | H | Me | H | H | Me | H | CH$_2$ | S |

(Stereochemistry at the carbon atom bearing $R^{13}$ and $R^{13'}$ is preferably the S-configuration)

With regard to Formula (E), the compounds have a structure according to the following:

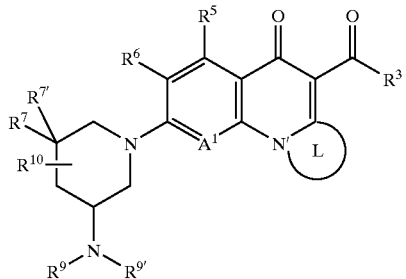

Formula (E)

These compounds are those of Formula (I) where Z is —C(COR3)-, and $R^1$ and $R^2$ join to form ring L, which is a mono- or bicyclic heterocycle comprising N'.

Table VI contains a non-limiting list of preferred compounds of Formula (F) having the following formula:

TABLE VI

| $A^1$ | $R^3$ | $R^5$ | $R^6$ | $R^7$ | $R^{7'}$ | $R^9$ | $R^{9'}$ | Each $R^{10}$ |
|---|---|---|---|---|---|---|---|---|
| CH | OH | H | F | Me | H | H | H | H |
| CH | OH | H | Cl | Me | H | H | H | H |
| CF | OH | H | F | Me | H | H | H | H |
| N | OH | H | F | Me | H | H | H | H |
| CH | OH | NH$_2$ | F | Me | H | H | H | H |
| CF | OH | NH$_2$ | F | Me | H | H | H | H |
| N | OH | NH$_2$ | F | Me | H | H | H | H |
| CH | OH | H | F | Me | H | Me | H | H |
| CF | OH | H | F | Me | H | Me | H | H |
| N | OH | H | F | Me | H | Me | H | H |
| CH | OH | NH$_2$ | F | Me | H | Me | H | H |
| CF | OH | NH$_2$ | F | Me | H | Me | H | H |
| N | OH | NH$_2$ | F | Me | H | Me | H | H |

Table VII contains a non-limiting list of preferred compounds of Formula (G) having the following formula:

TABLE VII

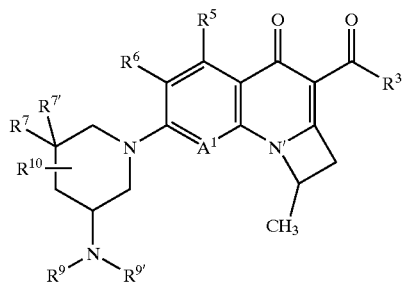

| $A^1$ | $R^3$ | $R^5$ | $R^6$ | $R^7$ | $R^{7'}$ | $R^9$ | $R^{9'}$ | Each $R^{10}$ |
|---|---|---|---|---|---|---|---|---|
| CH | OH | H | F | Me | H | H | H | H |
| CH | OH | H | Cl | Me | H | H | H | H |
| CF | OH | H | F | Me | H | H | H | H |
| N | OH | H | F | Me | H | H | H | H |
| CH | OH | NH$_2$ | F | Me | H | H | H | H |
| CF | OH | NH$_2$ | F | Me | H | H | H | H |
| N | OH | NH$_2$ | F | Me | H | H | H | H |
| CH | OH | H | F | Me | H | Me | H | H |
| CF | OH | H | F | Me | H | Me | H | H |
| N | OH | H | F | Me | H | Me | H | H |
| CH | OH | NH$_2$ | F | Me | H | Me | H | H |
| CF | OH | NH$_2$ | F | Me | H | Me | H | H |
| N | OH | NH$_2$ | F | Me | H | Me | H | H |

With regard to Formula (H), the compounds have a structure according to the following structure:

Formula (H)

These compounds are those of Formula (I) where Y is —N(R1)- where $R^2$ and $R^3$ of Formula (I) join to form a 5-membered heterocycloalkyl, where T is selected from —O—, —S— and substituted or unsubstituted —N—. In one embodiment, T is —S—.

Table VIII contains a non-limiting list of preferred compounds of Formula (H).

TABLE VIII

| $A^1$ | $R^1$ | $R^5$ | $R^6$ | $R^7$ | $R^{7'}$ | $R^9$ | $R^{9'}$ | Each $R^{10}$ | T |
|---|---|---|---|---|---|---|---|---|---|
| CH | cyclopropyl | H | F | Me | H | H | H | H | S |
| CH | cyclopropyl | H | Cl | Me | H | H | H | H | S |
| CF | cyclopropyl | H | F | Me | H | H | H | H | S |

TABLE VIII-continued

| $A^1$ | $R^1$ | $R^5$ | $R^6$ | $R^7$ | $R^{7'}$ | $R^9$ | $R^{9'}$ | Each $R^{10}$ | T |
|---|---|---|---|---|---|---|---|---|---|
| CH | cyclopropyl | $NH_2$ | F | Me | H | H | H | H | S |
| CF | cyclopropyl | $NH_2$ | F | Me | H | H | H | H | S |
| CH | cyclopropyl | H | F | Me | H | Me | H | H | S |
| CF | cyclopropyl | H | F | Me | H | Me | H | H | S |
| CH | cyclopropyl | $NH_2$ | F | Me | H | Me | H | H | S |
| CF | cyclopropyl | $NH_2$ | F | Me | H | Me | H | H | S |

The following provides a description of moiety embodiments with respect to each $A^1$, a, b and c, X, Y, Z, $R^2$, $R^5$, $R^6$, $R^7$, $R^{7'}$, $R^9$, $R^{9'}$ and $R^{10}$ of Formula (I).

$A^1$ is selected from —N— and —C($R^8$)—. In one embodiment $A^1$ is —C($R^8$)—, where $R^8$ is selected from hydrogen, halo, $C_1$ to about $C_6$ alkyl, $C_2$ to about $C_6$ alkene or alkyne and $C_1$ to about $C_6$ alkoxy, all such alkyl, alkene, alkyne and alkoxy moieties being unsubstituted or substituted with from 1 to about 3 fluoro. In one embodiment $R^8$ is hydrogen. In one embodiment $R^8$ is lower alkyl, preferred is where $R^8$ has from 1 to about 2 carbon atoms; methyl is preferred. In one embodiment $R^8$ is lower alkene, preferred $R^8$ has from 2 to about 4 carbon atoms; ethenyl is preferred. In one embodiment $R^8$ is lower alkoxy, preferred $R^8$ has from 1 to about 4 carbon atoms; methoxy is preferred. In one embodiment $R^8$ is lower alkylthio, preferred $R^8$ has from 1 to about 4 carbon atoms, methylthio is preferred. All $R^8$ alkyl and alkene moieties are unsubstituted or substituted with fluoro. In one embodiment $R^8$ is halo, preferred $R^8$ are chloro and fluoro. In one embodiment $R^8$ is selected from chloro, methyl, methoxy, methylthio, monofluoromethyl, difluoromethyl, trifluoromethyl, monofluoromethoxy, difluoromethoxy, and trifluoromethoxy. In one embodiment $R^8$ is selected from methyl substituted with from 1 to 3 fluoro, methoxy, methylthio, and chloro; especially either methoxy, methylthio or chloro.

a, b and c are each independently a single or double bond. In one embodiment, a is a double bond, b is a single bond, and c is a double bond. In one embodiment, a is a single bond, b is a double bond, and c is a double bond. In one embodiment, a is a double bond, b is a single bond, and c is a single bond.

X is selected from —C— or —N—. When X is —C—, a is a double bond and b is a single bond. In contrast, when X is —N—, a is a single bond and b is a double bond.

Y is selected from —N($R^1$)— and —CR°$R^1$—. However, Y is N($R^1$) only if X is —C— and Y is —C($R^1$)— only if X is —N— and Z is —C(COR$^3$)—.

Z is selected from —C(COR$^3$)—, —N($R^3$)— and —N(NHR$^3$)—. When Z is —C(COR$^3$)—, c is a double bond. In contrast, when Z is either —N($R^3$)— and —N(NHR$^3$)—, c is a single bond. However, Z is either —N($R^3$)— or —N(NHR$^3$)— only if X is —C—, Y is —N($R^1$)— and $A^1$ is —C($R^8$)—.

R° is selected from hydrogen and nil. When R° is hydrogen, b is single bond. In contrast, when R° is nil, b is a double bond.

$R^1$ is selected from $C_3$ to about $C_6$ cycloalkyl, $C_3$ to about $C_6$ heterocycloalkyl, $C_1$ to about $C_6$ alkyl, $C_2$ to about $C_6$ alkene or alkyne, $C_1$ to about $C_6$ alkyloxy, 6-membered aryl and 6-membered heteroaryl. All such alkyl, alkene, alkyne, alkoxy, cycloalkyl, aryl and heteroaryl substituents are unsubstituted or substituted with from 1 to 3 fluoro. All such aryl and heteroaryl are also unsubstituted or substituted with one hydroxy in the 4-position. In one embodiment, $R^1$ is selected from $C_3$ to about $C_6$ cycloalkyl, $C_3$ to about $C_6$ heterocycloalkyl, $C_1$ to about $C_4$ alkyl and $C_2$ to about $C_4$ alkene. In one embodiment, $R^1$ is selected from cyclopropyl, ethyl, t-butyl, 4-hydroxyphenyl and 2,4-difluorophenyl. In one embodiment $R^1$ is $C_3$ to about $C_6$ cycloalkyl. In one embodiment, $R^1$ is $C_1$ to about $C_4$ alkyl.

When $R^1$ is cycloalkyl, preferred are rings having from about 3 to about 5 ring carbon atoms, more preferably 3 ring carbon atoms. $R^1$ cycloalkyl moieties are preferably saturated or unsaturated with one double bond; more preferably $R^1$ cycloalkyl is saturated. When $R^1$ is linear lower alkyl, preferred is where $R^1$ contains from 1 to about 2 carbon atoms; methyl and ethyl are preferred, most preferred is ethyl. When $R^1$ is lower linear alkene, preferred is where $R^1$ contains from 2 to about 3 carbon atoms; ethenyl is preferred. When $R^1$ is branched lower alkyl or lower alkene, preferred is where $R^1$ contains from 3 to about 4 carbon atoms; branched lower alkyl is preferred; t-butyl is particularly preferred. All of the $R^1$ moieties mentioned in this paragraph are unsubstituted or substituted. When $R^1$ is substituted, preferred is one or more fluorine atoms.

When $R^1$ is a 6-membered aryl or a 6-membered heteroaryl aryl, the ring is unsubstituted or substituted with from 1 to about 3 fluorine atoms, one amino group (preferably at the 3-position of the ring), one hydroxy (preferably in the 4-position of the ring), or a combination of these substituents; substituted phenyl is preferred. Preferred $R^1$ moieties are selected from cyclopropyl, ethyl, phenyl substituted with 1 to 3 fluoro, and 4-hydroxyphenyl; more preferred is 2,4-difluorophenyl, and especially cyclopropyl or ethyl.

In one embodiment $R^1$ and $R^8$ combine to form a fused 6-membered heterocyclic ring $R^2$ is selected from hydrogen, double bond oxygen, $C_1$ to about $C_6$ alkyl, $C_2$ to about $C_6$ alkene or alkyne, $C_1$ to about $C_6$ alkoxy and $C_1$ to about $C_6$ thioalkyl. However, $R^2$ is double bond oxygen only if Z is either —N($R^3$)— or —N(NHR$^3$)—. In one embodiment, $R^2$ is hydrogen. In one embodiment $R^2$ is a double bond oxygen.

In one embodiment, $R^1$ and $R^2$ combine to form a fused 6-membered heterocyclic ring.

$R^3$ is selected from hydrogen, hydroxy, $C_1$ to about $C_6$ alkyl, $C_2$ to about $C_6$ alkene or alkyne, $C_1$ to about $C_6$ alkoxy and $C_1$ to about $C_6$ thioalkyl. In one embodiment, Z is —C(COR$^3$)— and $R^3$ is selected from hydrogen and hydroxy; preferred is hydroxy thereby forming a carboxylic acid moiety. This carboxylic moiety is a potential point of formation for the subject compounds of pharmaceutically-acceptable salts, and biohydrolizable esters, aminoacyls, and amides, as described herein. Compounds having any such variations at the $R^3$ position are included in the subject invention. In one embodiment, Z is —N($R^3$)— and $R^3$ is hydroxy. In one embodiment, Z is —N(NHR$^3$)— and $R^3$ is selected from hydrogen, hydroxy and $C_1$ to about $C_6$ alkyl.

In one embodiment, $R^2$ and $R^3$ combine to form a fused 6-membered heterocyclic ring.

$R^5$ is selected from hydrogen, hydroxy, amino, halo, $C_1$ to about $C_6$ alkyl, $C_2$ to about $C_4$ alkene or alkyne and $C_1$ to about $C_4$ alkoxy. All such alkyl, alkene, alkyne and alkoxy moieties are unsubstituted or substituted with from 1 to 3 fluoro. In one embodiment, $R^5$ is selected from $C_1$ to about $C_2$ alkyl, preferably $C_1$ alkyl. In one embodiment, $R^5$ is $C_2$ alkene. In one embodiment, $R^5$ is $C_1$ to about $C_2$ alkoxy. In one embodiment, $R^5$ is amino. All $R^5$ $C_1$ alkyl, $C_2$ alkene and $C_1$ to about $C_2$ alkoxy moieties are unsubstituted or substituted with fluoro moieties. In one embodiment $R^5$ is selected from hydrogen, hydroxy, chloro, bromo, amino, methyl, monofluoromethyl, difluoromethyl and trifluoromethyl. In one embodiment, $R^5$ is selected from hydrogen, hydroxy, amino, and methyl. In one embodiment, $R^5$ is hydrogen.

$R^6$ is selected from hydroxy, aminocarbonyl, fluoro, chloro, bromo, cyano, $C_1$ to about $C_2$ alkyl and $C_2$ to about $C_4$ alkenyl or alkynyl. All such alkyl, alkenyl and alkynyl moieties are unsubstituted or substituted with from 1 to about 3 fluoro. In one embodiment $R^6$ is selected from hydroxy, fluoro, chloro, bromo, and methyl. In one embodiment $R^6$ is selected from fluoro and chloro. In one embodiment $R^6$ is fluoro. In one embodiment $R^6$ is hydroxy. In one embodiment $R^6$ is methyl.

$R^7$ and $R^{7'}$ are each independently selected from hydrogen, $C_1$ to about $C_6$ alkyl, $C_2$ to about $C_6$ alkene or alkyne, $C_1$ to about $C_6$ alkoxy, $C_1$ to about $C_6$ alkylthio and $C_1$ to about $C_6$ heteroalkyl; provided $R^7$ and $R^{7'}$ are not both hydrogen; or $R^7$ and $R^{7'}$ join to form a $C_3$ to about $C_6$ cycloalkyl or heterocyclic ring containing the carbon atom to which they are bonded. All such alkyl, alkene, alkyne, alkoxy, alkythio, heteroalkyl, cycloalkyl and heterocyclic moieties are unsubstituted or substituted with from 1 to 3 fluoro. In one embodiment, $R^7$ and $R^{7'}$ join to form a $C_3$ to about $C_6$ cycloalkyl. In one embodiment, $R^7$ and $R^{7'}$ join to form a cyclopropyl. In one embodiment, $R^7$ and $R^{7'}$ are selected from $C_1$ to about $C_3$ alkyl or $C_1$ to about $C_3$ alkyloxy. In one embodiment, $R^{7'}$ is hydrogen and $R^7$ is selected from hydrogen $C_1$ to about $C_3$ alkyl and $C_1$ to about $C_3$ alkyloxy; provided $R^7$ and $R^{7'}$ are not both hydrogen. In one embodiment, $R^{7'}$ is hydrogen and $R^7$ is selected from methoxy, thiomethoxy, methyl and ethyl, all such methoxy, thiomethoxy, methyl and ethyl moieties being unsubstituted or substituted with from 1 to about 3 fluoro. In one embodiment, $R^{7'}$ is hydrogen and $R^7$ is selected from methyl and ethyl. In one embodiment, $R^{7'}$ is hydrogen and $R^7$ is selected from $C_1$ to about $C_6$ alkyl, $C_2$ to about $C_6$ alkene or alkyne, $C_1$ to about $C_6$ alkoxy, $C_1$ to about $C_6$ alkylthio and $C_1$ to about $C_6$ heteroalkyl and the carbon atom piperidine ring member, to which $R^7$ is attached, is of the S-configuration. In one embodiment, $R^{7'}$ is hydrogen and $R^7$ is methyl and the carbon atom piperidine ring member, to which $R^7$ is attached, is of the S-configuration.

$R^9$ and $R^{9'}$ are each independently selected from hydrogen and $C_1$ to about $C_3$ alkyl, or $R^9$ and $R^{9'}$ join to form a $C_3$ to about $C_6$ heterocyclic ring containing the nitrogen atom to which they are bonded. In one embodiment $R^9$ and $R^{9'}$ are each independently selected from hydrogen, methyl and ethyl. In one embodiment $R^9$ and $R^{9'}$ join to form a $C_3$ heterocyclic ring. In one embodiment, $R^9$ and $R^{9'}$ are each independently selected from hydrogen and methyl. In one embodiment $R^9$ and $R^{9'}$ are each hydrogen. In one embodiment, each $R^9$ and $R^{9'}$ are each independently selected from hydrogen and methyl, and the carbon atom piperidine ring member, to which —$NR^9R^{9'}$ is attached, is of the S-configuration. In one embodiment, $R^9$ and $R^{9'}$ are both hydrogen and the carbon atom piperidine ring member, to which —$NR^9R^{9'}$ is attached, is of the S-configuration.

$R^{10}$ represents the moieties on the piperidine ring other than $R^7$, $R^{7'}$ and —$NR^9R^{9'}$, where each $R^{10}$ is independently selected from hydrogen, $C_1$ to about $C_6$ alkyl, $C_2$ to about $C_6$ alkene or alkyne, $C_1$ to about $C_6$ alkoxy, $C_3$–$C_6$ cycloalkyl all such alkyl, alkene, alkyne, alkoxy and cycloalkyl moieties being unsubstituted or substituted with from 1 to 3 fluoro. In one embodiment, each $R^{10}$ is selected from hydrogen, methyl, ethyl, isopropyl, cyclopropyl and methoxy. In one embodiment, each $R^{10}$ is selected from hydrogen, methyl and ethyl. In one embodiment, each $R^{10}$ is hydrogen. In one embodiment, the carbon atom piperidine ring member to which $R^{10}$ is attached is of the S-configuration.

As used herein, any radical is independently selected each time it is used (e.g., $R^1$ and $R^5$ need not be the same in all occurrences in defining a given compound of this invention).

The compounds of the invention may contain chiral center(s), thus any such compound includes and contemplates each optical isomer, diastereomer or enantiomer thereof, in purified or substantially purified form, and mixtures thereof, including racemic mixtures.

The following exemplary compounds are made using the procedures described herein and variations thereof which are within the purview of the skilled artisan's practice. The examples below do not limit the invention, but rather serve to illustrate some of the embodiments of the invention.

In one aspect, the present invention is directed to compounds of Formula (I) wherein X is —C—, Y is —N($R^1$)—, Z is —C(COR$^1$)—, a is a double bond, b is a single bond, c is a double bond, and $R^9$ and $R^{9'}$ are both hydrogen. In this aspect, compounds have a structure according to the following Formula (II):

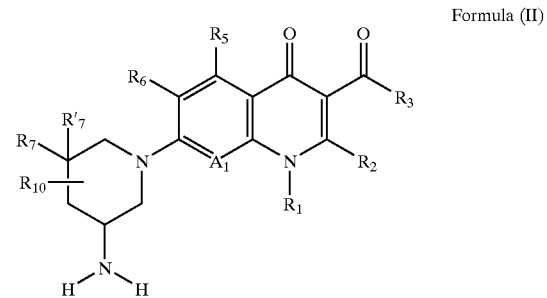

Formula (II)

where $A^1$, $R^1$, $R^2$, $R^3$, $R^5$, $R^6$, $R^7$, $R^{7'}$ and $R^{10}$ are as defined with regard to Formula (I). In one embodiment, the compounds are those of Formula (II) where $A^1$ is —C($R^8$)—. In one embodiment, compounds of Formula (II) are those where $R^8$ and $R^1$ do not join to form a ring.

In another aspect, the present invention is directed to compounds of Formula (I) where X is —N—, $A^1$ is —C($R^8$)—, Y is —C($R^1$)—, Z is —C(COR$^3$)—, a is a single bond, b is a double bond, c is a double bond, and $R^9$ and $R^{9'}$ are both hydrogen. In this aspect, compounds have a structure according to the following Formula (III):

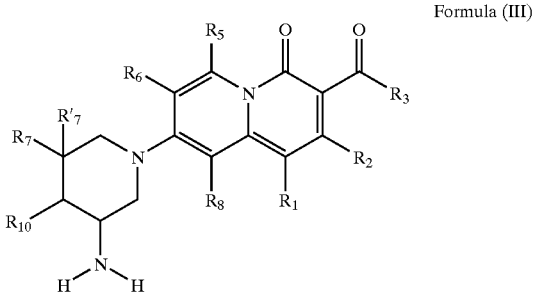

Formula (III)

where $R^1$, $R^2$, $R^3$, $R^5$, $R^6$, $R^7$, $R^{7'}$ and $R^{10}$ are as defined with regard to Formula (I). In one embodiment, compounds of Formula (III) are those where $R^8$ and $R^1$ do not join to form a ring.

In another aspect, the present invention is directed to compounds of Formula (I) where X is —C—, $A^1$ is —C($R^8$)—, Y is —N($R^1$)—, $R^2$ is a double bond oxygen, a is a double bond, b is a single bond, c is a single bond, and $R^9$ and $R^{9'}$ are both hydrogen. In this aspect, compounds have a structure according to the following Formula (IV):

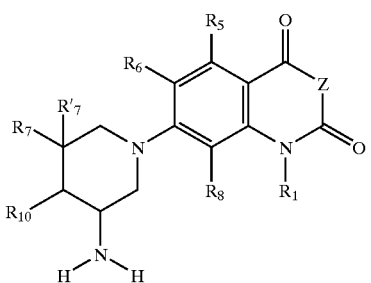

where Z, $R^1$, $R^5$, $R^6$, $R^7$, $R^{7'}$, $R^8$ and $R^{10}$ are as defined with regard to Formula (I).

The subject invention compounds above are also useful precursors for compounds of formula Q-L-B, wherein Q is a compound of Formula I, L is a linking moiety, and B is a lactam-containing moiety. This formula includes optical isomers, disatereomers or enantiomers thereof; pharmaceutically-acceptable salts, hydrates, or biohydrolyzable esters, amides and imides thereof. These compounds and their uses are disclosed in U.S. Pat. No. 5,180,719 issued Jan. 19, 1993; U.S. Pat. No. 5,387,748 issued Feb. 7, 1995; U.S. Pat. No. 5,491,139 issued Feb. 13, 1996; U.S. Pat. No. 5,530,116 issued Jun. 25, 1996; and European Patent Publication Nos. 366,189, published May 2, 1990, and 366,640 published May 2, 1990, all incorporated herein by reference. For compositions and methods of use, the compounds of formula Q-L-B are useful in the same way as compounds of Formula I. Thus, they can be interchanged in the composition examples herein.

Biological activities of the invention compounds can be compared to ciprofloxacin and the other known antimicrobial quinolone compounds. Compounds of the subject invention provide better antibacterial properties against certain quinolone resistant bacteria compared to ciprofloxacin and certain other prior art compounds. When tested against quinolone-resistant bacteria such as S. aureus, S. saprophyticus, E. faecalis, S. pyogenes, S. pneumoniae, S. viridans, E. coli, P. aeruginosa, P. mirabilis, K. pneumoniae, E. cloacae, certain compounds of the subject invention have been found to have MIC values (µg/mL) are lower than ciprofloxacin.

Clastogenicity profiles of the invention compounds can be compared to glatifloxacin. Certain compounds of the subject invention provide a better clastogenecity profile compared to glatifloxacin and other prior art compounds. A suitable clastogenicity assay is described in V. Cigvarino, M. J. Suto, J. C. Thiess, Mutation Research, Vol. 298, p. 227 (1993).

III. General Reaction Schemes for Compound Preparation:

In making the compounds of the invention, the order of synthetic steps may be varied to increase yield of desired product. In addition, the skilled artisan will also recognize the judicious choice of reactants, solvents, and temperatures is an important component in successful synthesis. While the determination of optimal conditions, etc. is routine, it will be understood that a variety of compounds can be generated in a similar fashion, using the guidance of the scheme below. Specific synthetic examples are set forth for a variety of compounds in Section VI.

The starting materials used in preparing the compounds of the invention are known, made by known methods, or are commercially available as a starting material.

It is recognized that the skilled artisan in the art of organic chemistry can readily carry out standard manipulations of organic compounds without further direction; that is, it is well within the scope and practice of the skilled artisan to carry out such manipulations. These include, but are not limited to, reduction of carbonyl compounds to their corresponding alcohols, oxidations, acylations, aromatic substitutions, both electrophilic and nucleophilic, etherifications, esterification and saponification and the like. Examples of these manipulations are discussed in standard texts such as March, Advanced Organic Chemistry (Wiley), Carey and Sundberg, Advanced Organic Chemistry (Vol. 2), Fieser & Feiser, Reagents for Organic Synthesis (16 volumes), L. Paquette, Encyclopedia of Reagents for Organic Synthesis (8 volumes), Frost & Fleming, Comprehensive Organic Synthesis (9 volumes) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene, Protecting Groups in Organic Synthesis. Of course, amino acids used as starting materials with reactive side chains are preferably blocked to prevent undesired side reactions.

General procedures for preparing quinolone moieties useful in making the compounds of the subject invention are described in the following references, all incorporated by reference herein (including articles listed within these references): Progress in Drug Research, Vol. 21, pp. 9–104 (1977); J. Med. Chem., Vol. 23, pp. 1358–1363 (1980); J. Med. Chem., Vol. 29, pp. 2363–2369 (1986); J. Med. Chem., Vol. 31, p. 503 (1988); J. Med. Chem., Vol. 31, pp. 503–506 (1988); J. Med. Chem., Vol. 31, pp. 983–991 (1988); J. Med. Chem., Vol. 31, pp. 991–1001 (1988); J. Med. Chem., Vol. 31, pp. 1586–1590 (1988); J. Med. Chem., Vol. 31, pp. 1598–1611 (1988); J. Med. Chem., Vol. 32, pp. 537–542 (1989); J. Med. Chem., Vol. 32, p. 1313 (1989); J. Med. Chem., Vol. 32, pp. 1313–1318 (1989); Drugs Exptl. Clin. Res., Vol. 14, pp. 379–383 (1988); J. Pharm. Sci., Vol. 78, pp. 585–588 (1989); J. Het. Chem., Vol. 24, pp. 181–185 (1987); J. Het. Chem., Vol. 25, pp. 479–485 (1988); Chem. Pharm. Bull., Vol. 35, pp. 2281–2285 (1987); Chem. Pharm.

*Bull.*, Vol. 36, pp. 1223–1228 (1988); U.S. Pat. No. 4,594, 347, Jun. 10, 1986; U.S. Pat. No. 4,599,334, Jul. 8, 1986; U.S. Pat. No. 4,687,770, Aug. 1, 1987; U.S. Pat. No. 4,689,325, Aug. 25, 1987; U.S. Pat. No. 4,767,762, Aug. 30, 1988; U.S. Pat. No. 4,771,055, Sep. 13, 1988; U.S. Pat. No. 4,795,751, Jan. 3, 1989; U.S. Pat. No. 4,822,801, Apr. 18, 1989; U.S. Pat. No. 4,839,355, Jun. 13, 1989; U.S. Pat. No. 4,851,418, Jul. 25, 1989; U.S. Pat. No. 4,886,810, Dec. 12, 1989; U.S. Pat. No. 4,920,120, Apr. 24, 1990; U.S. Pat. No. 4,923,879, May 8, 1990; U.S. Pat. No. 4,954,507, Sep. 4, 1990; U.S. Pat. No. 4,956,465, Sep. 11, 1990; U.S. Pat. No. 4,977,154, Dec. 11, 1990; U.S. Pat. No. 4,980,470, Dec. 25, 1990; U.S. Pat. No. 5,013,841, May 7, 1991; U.S. Pat. No. 5,045,549, Sep. 3, 1991; U.S. Pat. No. 5,290,934, Mar. 1, 1994; U.S. Pat. No. 5,328,908, Jul. 12, 1994; U.S. Pat. No. 5,430,152, Jul. 4, 1995; European Patent Publication 172, 651, Feb. 26, 1986; European Patent Publication 230,053, Jul. 29, 1987; European Patent Publication 230,946, Aug. 5, 1987; European Patent Publication 247,464, Dec. 2, 1987; European Patent Publication 284,935, Oct. 5, 1988; European Patent Publication 309,789, Apr. 5, 1989; European Patent Publication 332,033, Sep. 13, 1989; European Patent Publication 342,649, Nov. 23, 1989; and Japanese Patent Publication 09/67,304 (1997).

Suitable methods for making quinazolin-2-4-dione compounds of the present invention are described in International Patent Publication 01/53273 A1.

The quinolone compounds of the subject invention may be prepared in several ways. Versatile methodologies for providing the compounds of the invention are shown in Scheme I below:

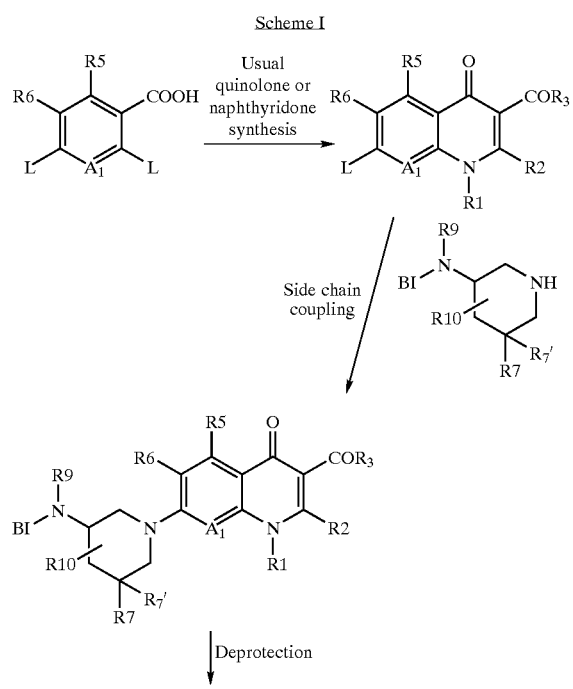

Methodologies for providing the compounds of the invention where X is —N— and Y is —C($R^1$)— are shown in Scheme II below:

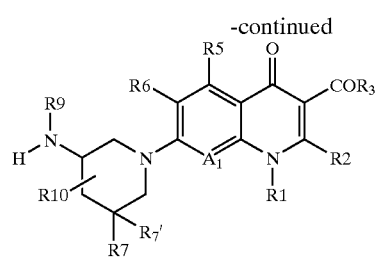

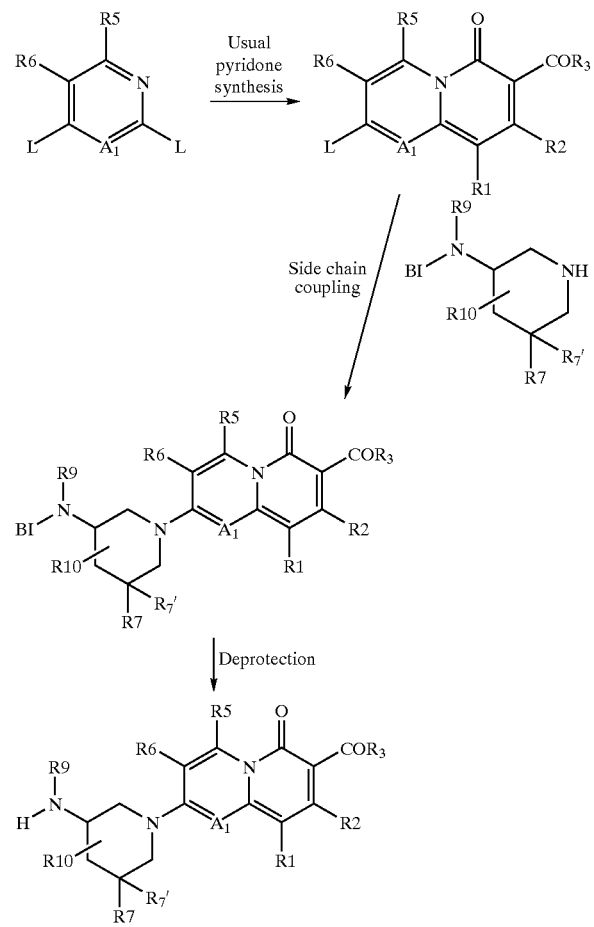

IV. Compositions:

The compositions of this invention comprise:
(a) a safe and effective amount of the compound of the invention
(b) a pharmaceutically-acceptable excipient.

The compositions may also optionally comprise other antimicrobials or other actives, which may or may not act synergystically with the invention.

A "safe and effective amount" of a quinolone is an amount that is effective, to inhibit microbial growth at the site of an infection to be treated in a host, without undue adverse side effects (such as toxicity, irritation, or allergic response), commensurate with a reasonable benefit/risk ratio when used in the manner of this invention. The specific "safe and effective amount" will vary with such factors as the particular condition being treated, the physical condition of the patient, the duration of treatment, the nature of concurrent therapy (if any), the specific dosage form to be used, the excipient employed, the solubility of the quinolone therein, and the dosage regimen desired for the composition.

The compositions of this invention are preferably provided in unit dosage form. As used herein, a "unit dosage form" is a composition of this invention containing an amount of a quinolone that is suitable for administration to a human or lower animal subject, in a single dose, according to good medical practice. These compositions preferably contain from about 30 mg, more preferably from about 50 mg, more preferably still from about 100 mg, preferably to about 20,000 mg, more preferably to about 7,000 mg, more preferably still to about 1,000 mg, most preferably to about 500 mg, of a quinolone.

The compositions of this invention may be in any of a variety of forms, suitable (for example) for oral, rectal, topical or parenteral administration. Depending upon the particular route of administration desired, a variety of pharmaceutically-acceptable excipients well-known in the art may be used. These include solid or liquid fillers, diluents, hydrotropes, surface-active agents, and encapsulating substances. Optional pharmaceutically-active materials may be included, which do not substantially interfere with the antimicrobial activity of the quinolone. The amount of excipient employed in conjunction with the quinolone is sufficient to provide a practical quantity of material for administration per unit dose of the quinolone. Techniques and compositions for making dosage forms useful in the methods of this invention are described in the following references, all incorporated by reference herein: *Modern Pharmaceutics*, Vol. 7, Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

In particular, pharmaceutically-acceptable excipients for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred excipients for parenteral administration include propylene glycol, ethyl oleate, pyrrolidone, ethanol, and sesame oil. Preferably, the pharmaceutically-acceptable excipient, in compositions for parenteral administration, comprises at least about 90% by weight by the total composition.

In addition, dosages for injection may be prepared in dried or lyophilized form. Such forms can be reconstituted with water or saline solution, depending on the preparation of the dosage form. Such forms may be packaged as individual dosages or multiple dosages for easier handling. Where lyophilized or dried dosages are used, the reconstituted dosage form is preferably isotonic, and at a physiologically compatible pH.

Various oral dosage forms can be used, including such solid forms as tablets, capsules, granules and bulk powders. These oral forms comprise a safe and effective amount, usually at least about 5%, and preferably from about 25% to about 50%, of the quinolone. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents, such are well known to the skilled artisan. Preferred excipients for oral administration include gelatin, propylene glycol, cottonseed oil and sesame oil.

The compositions of this invention can also be administered topically to a subject, i.e., by the direct laying on or spreading of the composition on the epidermal or epithelial tissue of the subject. Such compositions include, for example, lotions, creams, solutions, gels and solids. These topical compositions preferably comprise a safe and effective amount, usually at least about 0.1%, and preferably from about 1% to about 5%, of the quinolone. Suitable excipients for topical administration preferably remain in place on the skin as a continuous film, and resist being removed by perspiration or immersion in water. Generally, the excipient is organic in nature and capable of having dispersed or dissolved therein the quinolone. The excipient may include pharmaceutically-acceptable emolients, emulsifiers, thickening agents, and solvents and the like; these are well known to the skilled artisan.

V. Methods of Using the Compounds:

This invention also provides methods of treating an infectious disorder in a human or other animal subject, by administering a safe and effective amount of a quinolone to said subject. As used herein, an "infectious disorder" is any disorder characterized by the presence of a microbial infection. Preferred methods of this invention are for the treatment of bacterial infections. Such infectious disorders include (for example) central nervous system infections, external ear infections, infections of the middle ear (such as acute otitis media), infections of the cranial sinuses, eye infections, infections of the oral cavity (such as infections of the teeth, gums and mucosa), upper respiratory tract infections, lower respiratory tract infections, including pneumonia, genitourinary infections, gastrointestinal infections, gynecological infections, septicemia, sepsis, peritonitis, bone and joint infections, skin and skin structure infections, bacterial endocarditis, burns, antibacterial prophylaxis of surgery, and antibacterial prophylaxis in post-operative patients or in immunosuppressed patients (such as patients receiving cancer chemotherapy, or organ transplant patients).

The term "treatment" is used herein to mean that, at a minimum, administration of a compound of the present invention mitigates a disease associated an infectious disorder in a host, preferably in a mammalian subject, more preferably in humans. Thus, the term "treatment" includes: preventing an infectious disorder from occurring in a host, particularly when the host is predisposed to acquiring the disease, but has not yet been diagnosed with the disease; inhibiting the infectious disorder; and/or alleviating or reversing the infectious disorder. Insofar as the methods of the present invention are directed to preventing infectious disorders, it is understood that the term "prevent" does not require that the disease state be completely thwarted. (See Webster's Ninth Collegiate Dictionary.) Rather, as used herein, the term preventing refers to the ability of the skilled artisan to identify a population that is susceptible to infectious disorders, such that administration of the compounds of the present invention may occur prior to onset of infection. The term does not imply that the disease state be completely avoided.

The quinolone derivatives and compositions of this invention can be administered topically or systemically. Systemic application includes any method of introducing the quinolone into the tissues of the body, e.g., intrathecal, epidural, intramuscular, transdermal, intravenous, intraperitoneal, subcutaneous, sublingual, rectal, and oral administration. The specific dosage of antimicrobial to be administered, as well as the duration of treatment, are mutually dependent.

The dosage and treatment regimen will also depend upon such factors as the specific quinolone used, the resistance pattern of the infecting organism to the quinolone used, the ability of the quinolone to reach minimum inhibitory concentrations at the site of the infection, the nature and extent of other infections (if any), the personal attributes of the subject (such as weight), compliance with the treatment regimen, the age and health status of the patient, and the presence and severity of any side effects of the treatment.

Typically, for a human adult (weighing approximately 70 kilograms), from about 75 mg, more preferably from about 200 mg, most preferably from about 500 mg to about 30,000 mg, more preferably to about 10,000 mg, most preferably to about 3,500 mg, of quinolone is administered per day. Treatment regimens preferably extend from about 1, preferably from about 3 to about 56 days, preferably to about 20 days, in duration. Prophylactic regimens (such as avoidance of opportunistic infections in immunocompromised patients) may extend 6 months, or longer, according to good medical practice.

A preferred method of parenteral administration is through intravenous injection. As is known and practiced in the art, all formulations for parenteral administration must be sterile. For mammals, especially humans, (assuming an approximate body weight of 70 kilograms) individual doses of from about 100 mg, preferably from about 500 mg to about 7,000 mg, more preferably to about 3,500 mg, is acceptable.

In some cases, such as generalized, systemic infections or in immune-compromised patients, the invention may be dosed intravenously. The dosage form is generally isotonic and at physiological pH. The dosage amount will depend on the patient and severity of condition, as well as other commonly considered parameters. Determination of such doses is well within the scope of practice for the skilled practitioner using the guidance given in the specification.

A preferred method of systemic administration is oral administration. Individual doses of from about 20 mg, more preferably from about 100 mg to about 2,500 mg, more preferably to about 500 mg.

Topical administration can be used to deliver the quinolone systemically, or to treat a local infection. The amounts of quinolone to be topically administered depends upon such factors as skin sensitivity, type and location of the tissue to be treated, the composition and excipient (if any) to be administered, the particular quinolone to be administered, as well as the particular disorder to be treated and the extent to which systemic (as distinguished from local) effects are desired.

VI. EXAMPLES

Compound Preparation a. Precursor Preparation—Nuclei:

Precursor Example A

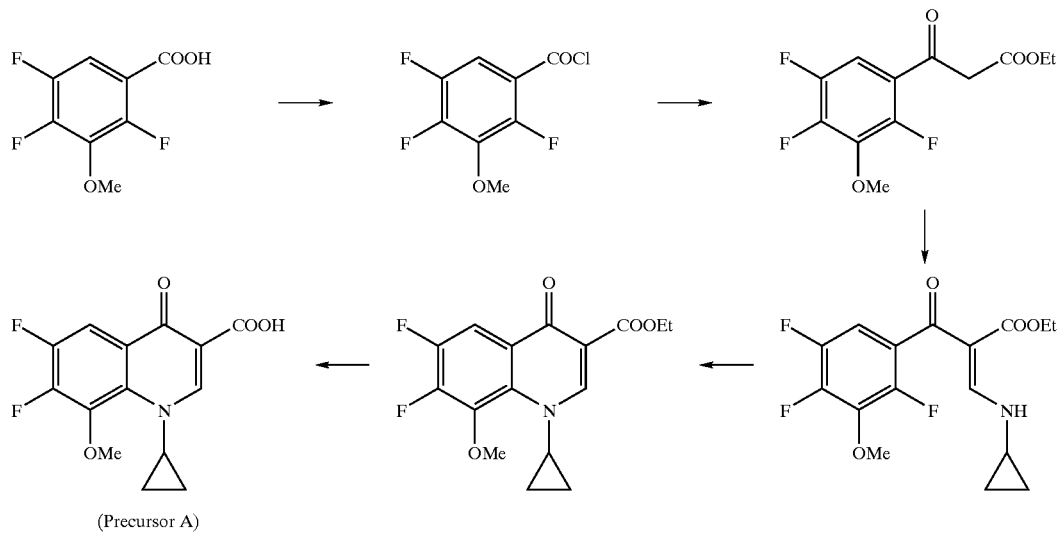

(Precursor A)

3-methoxy-2,4,5-trifluorobenzoyl chloride

3-Methoxy-2,4,5-difluorobenzoic acid (43.9 g, 213 mmol) is suspended in dichloromethane (30 mL) and oxalyl chloride (25 mL, 287 mmol) is added followed by 4 drops of dry DMF. The mixture is stirred at room temperature for 6 hours and the solvent is removed by evaporation to afford the desired product.

Ethyl 3-methoxy-2,4,5-trifluoro-benzoyl acetate

Monoethyl malonate (26.4 g, 200 mmol) is dissolved in THF (700 mL). The solution is cooled at −50° C. and n-butyllithium (160 mL 2.5 $\underline{M}$, 400 mmol) is added, keeping the temperature below −50° C. The temperature is initially raised to 0° C. and cooled back to −50° C. 3-methoxy-2,4, 5-trifluorobenzoyl chloride (20.6 g, 92 mmol) is added, keeping the temperature at −50° C., then the reaction mixture is warmed to room temperature. Hydrochloric acid is added until the pH becomes acidic. The organic phase is washed with sodium bicarbonate and dried; evaporation of the solvent affords the desired product.

Ethyl 3-cyclopropylamino-2-(3-methoxy-2,4,5-trifluoro-benzoyl)acrylate

To a mixture of acetic anhydride (50 mL, 530 mmol) and triethyl orthoformate (50 mL, 300 mmol) is added ethyl 3-methoxy-2,4,5-trifluoro-benzoyl acetate (52.94 g, 192 mmol). The mixture is refluxed for 2 hours, then is cooled to room temperature. The excess reagent is removed by evaporation to provide a thick oil which is dissolved in ethanol (150 mL). Cyclopropylamine (17.2 g, 301 mmol) is then added while keeping the temperature at about 20° C. The desired product is isolated by filtration and air dried.

Ethyl 1-cyclopropyl-6,7-difluoro-1,4-dihydro-8-methoxy-4-oxo-quinoline-3-carboxylate Ethyl 3-cyclopropylamino-2-(3-methoxy-2,4,5-trifluoro-benzoyl) acrylate (30.3 g, 88 mmol) is dissolved in THF. 60% sodium hydride in oil (4.1 g, 103 mmol) is added portion-wise keeping the temperature below 40° C. The solution is stirred at room temperature for 2 hours, then poured into water. The desired product is isolated by filtration and air dried.

1-Cyclopropyl-6,7-difluoro-1,4-dihydro-8-methoxy-4-oxo-quinoline-3-carboxylic acid (Precursor A)

Ethyl-1-cyclopropyl-1,4-dihydro-6,7-difluoro-8-methoxy-4-oxo-quinoline-3-carboxylate (28.6 g, 88 mmol) is suspended in a mixture of acetic acid, water, sulfuric acid (8/6/1, 300 mL) and is refluxed for 2 hours. The reaction mixture is cooled at 0° C. and the desired product is collected by filtration.

Precursor Example B

Ethyl 5-bromo-3-chloro-2,4-difluoro-benzoyl acetate

Magnesium (0.475 g, 19.5 mmol) is suspended in ethanol (1.5 mL, 26.5 mmol) and carbon tetrachloride (0.16 mL) is added. A solution of diethylmalonate (3 mL, 19.7 mmol) in ethanol (15 mL) is added dropwise and the mixture is stirred at 60° C. until the magnesium has completely dissolved. The mixture is cooled at −5° C. and 5-bromo-3-chloro-2,4-difluorobenzoyl chloride (5.5 g, 19.0 mmol) is added dropwise. The mixture is stirred at room temperature for 1 hour. Diethyl ether (50 mL) and water (20 mL) are added and the mixture is acidified with concentrated hydrochloric acid. After separation of the organic phase and removal of the solvent, the residue is suspended in water (40 mL) and PTSA (0.1 g) is added. The suspension is heated at reflux for 2 hours, cooled to room temperature, and extracted with diethyl ether. The desired product is obtained after evaporation of the solvent.

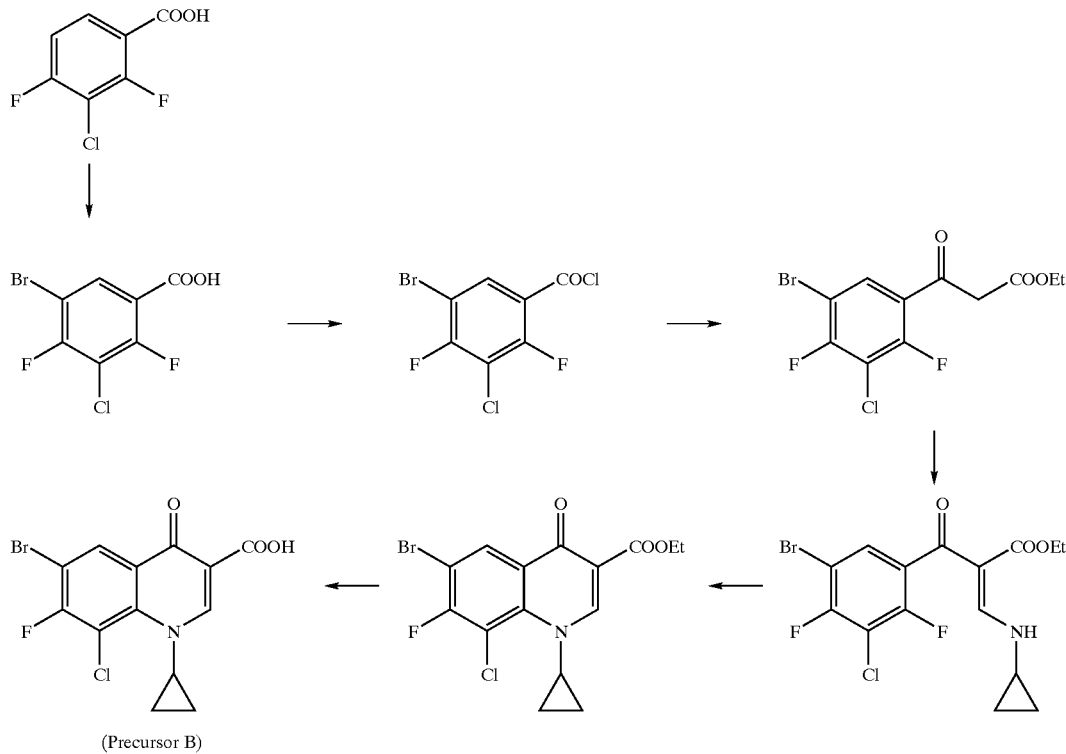

(Precursor B)

5-Bromo-3-chloro-2,4-difluorobenzoic acid

To a mixture of acetic acid (100 mL), water (20 mL), and nitric acid (26 mL) is added 3-chloro-2,4-difluorobenzoic acid (4 g, 21 mmol) and bromine (2.2 mL, 43 mmol). A solution of silver nitrate (7.0 g 41 mmol) in water (20 mL) is then added slowly. After 14 hours at 20° C., the precipitate is filtered and rinsed with ether. The organic phase is washed with sodium bisulfite, water, brine, and dried over MgSO$_4$. Removal of the spent dessicant and concentration of the solvent affords the desired product.

5-Bromo-3-chloro-2,4-difluorobenzoyl chloride 5-bromo-3-chloro-2,4-difluorobenzoic acid (5.2 g, 19 mmol) is suspended in dichloromethane (30 mL) and oxalyl chloride (2.92 g, 23 mmol) and dry DMF (3 drops) are added. The mixture is stirred at room temperature for 3 hours and the desired compound is isolated after evaporation of the solvent.

Ethyl 3-cyclopropylamino-2-(5-bromo-3-chloro-2,4-difluoro-benzoyl)acrylate

Ethyl 5-bromo-2,4-difluoro-3-chloro-benzoyl acetate (6.2 g, 18 mmol) is dissolved in a mixture of acetic anhydride (4.4 mL, 47 mmol) and triethyl orthoformate (4.5 mL, 27 mmol) and the mixture is heated at reflux for 2 hours. The volatiles are evaporated, the residue is dissolved in ethanol (20 mL), and the resulting solution is cooled at 0° C. Cyclopropylamine (2 mL, 29 mmol) is added and, after 30 minutes, the desired product is isolated by filtration and air dried.

Ethyl 6-bromo-8-chloro-1-cyclopropyl-1,4-dihydro-7-fluoro-4-oxo-quinoline-3-carboxylate Ethyl 3-cyclopropylamino-2-(5-bromo-2,4-difluoro-3-chloro-benzoyl) acrylate (2.95 g, 7 mmol) is dissolved in THF (15 mL) and 60% sodium hydride (0.29 g, 7 mmol) is added portionwise. After 1 hour at room temperature, the suspension is poured into water (100 mL) and the desired product isolated by filtration and air dried.

6-Bromo-8-chloro-1-cyclopropyl-1,4-dihydro-7-fluoro-4-oxoquinoline-3-carboxylic acid (Precursor B)

Ethyl 6-bromo-1-cyclopropyl-1,4-dihydro-7-fluoro-8-chloro-4-oxo-quinoline-3-carboxylate (1.9 g, 5 mmol) is suspended in a mixture of acetic acid, water, sulfuric acid (8/6/1, 30 mL) and is refluxed for 2 hours. The reaction mixture is cooled to room temperature and poured into cold water (50 mL). The precipitate is collected by filtration, washed with water, and air dried.

Precursor Example C

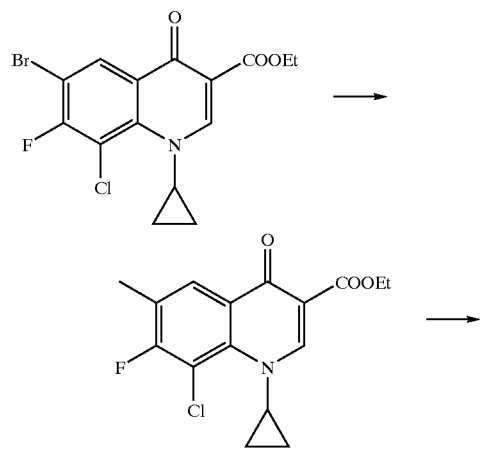

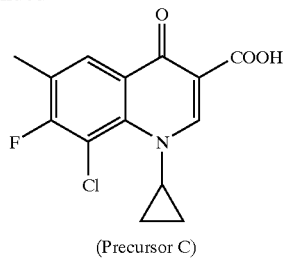

(Precursor C)

Ethyl 8-chloro-1-cyclopropyl-1,4-dihydro-7-fluoro-6-methyl-4-oxoquinoline-3-carboxylate Ethyl 6-Bromo-8-chloro-1-cyclopropyl-7-fluoro-1,4-dihydro-4-oxoquinoline-3-carboxyate (0.5 g, 1.3 mmol), lithium chloride (0.165 g, 3.9 mmol), tris(dibenzylideneacetone)dipalladium (0.120 g, 0.13 mmol), tetramethyltin (0.465 g, 2.6 mmol) and 2,6-di-tert-butyl-4-methyl-phenol (BHT, 25 mg) are combined in DMF (40 mL) and heated at 70–75° C. for 18 hours. The solvent is then removed in vacuo. The residue is triturated with hexanes and then purified by flash chromatography on silica gel using 1% methanol in chloroform to give the desired product.

8-chloro-1-cyclopropyl-1,4-dihydro-7-fluoro-6-methyl-4-oxoquinoline-3-carboxylic acid (Precursor C)

Ethyl 8-chloro-1-cyclopropyl-1,4-dihydro-7-fluoro-6-methyl-4-oxo-quinoline-3-carboxylate (0.290 g, 0.9 mmol) is suspended in a mixture of acetic acid, water, sulfuric acid (8/6/1, 3 mL) and is refluxed for 2 hours. The reaction mixture is cooled to room temperature and poured into cold water (5 mL). The precipitate is collected by filtration, washed with water, and air dried.

Precursor Example D

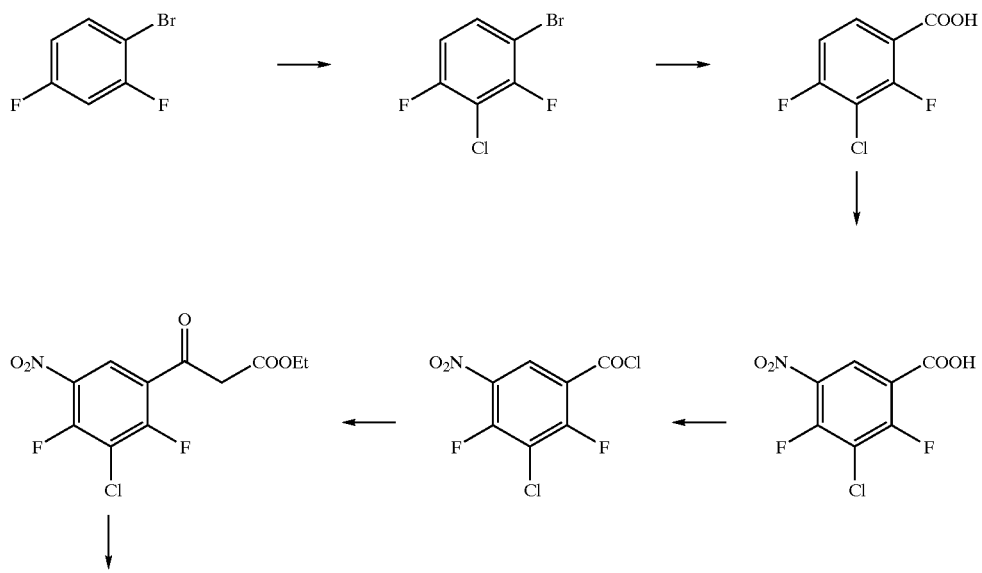

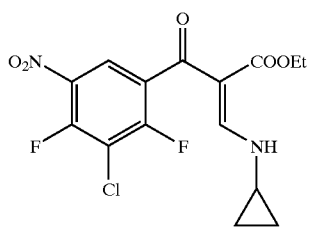 → 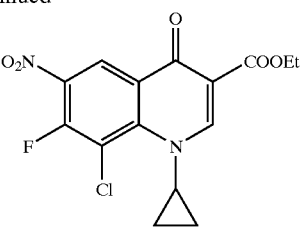

(Precursor D)

3-Chloro-2,4-difluoro-bromobenzene

To a solution of diisopropylamine (19 mL, 135 mmol) in THF (125 mL) cooled at −20° C. is added n-butyllithium (80 mL, 1.6 M in hexane, 128 mmol). The temperature is raised to 0° C. for 5 minutes and lowered to −78° C. Then 2,4-difluoro-bromobenzene (25 g, 130 mmol) is then added and the reaction mixture is stirred at −65° C. for 2 hours. Hexachloroacetone (25 mL, 164 mmol) is added and the solution is warmed to room temperature. After evaporation of the solvent, the residue is distilled under vacuum to give the desired product.

3-Chloro-2,4-difluorobenzoic acid

To a solution of 3-chloro-2.4-difluoro-bromobenzene (21.5 g, 94.5 mmol) in ether (220 mL) at −78° C. is added a mixture of n-butyllithium (59 mL, 1.6 M in hexane, 94.4 mmol) in $Et_2O$ (60 mL) keeping the temperature below −70° C. After 15 minutes, $CO_2$ is bubbled into the reaction mixture keeping the temperature below −70° C. After warming to room temperature, water and hydrochloric acid are added and the organic phase is separated, and dried. Removal of the solvent affords the desired product.

5-Nitro-3-chloro-2,4-difluorobenzoic acid

3-Chloro-2,4-difluorobenzoic acid (10 g, 52 mmol) is added to a mixture of fuming nitric acid (10 mL) and sulfuric acid (13 mL) at 0° C. The suspension is then stirred at room temperature for 30 minutes and poured onto ice. Filtration of the resulting solid affords the desired product.

5-Nitro-3-chloro-2,4-difluorobenzoyl chloride

5-Nitro-3-chloro-2,4-difluorobenzoic acid (6.94 g, 29 mmol) and oxalyl chloride (4.06 g, 32 mmol) are dissolved in dichloromethane (30 mL) then four drops of DMF are added. The reaction mixture is stirred for 14 hours at room temperature and the solvent is evaporated under reduced pressure to give the desired product.

Ethyl 5-nitro-3-chloro-2,4-difluoro-benzoyl acetate

Monoethyl malonate (3.26 g, 24.7 mmol) is dissolved in THF (10 mL) and the solution is cooled at −50° C. n-Butyllithium (30 mL, 1.6 M, 48 mmol) is added over a period of 30 minutes. A solution of 5-nitro-3-chloro-2,4-difluorobenzoyl chloride (3.35 g, 13 mmol) of in THF (2 mL) is added keeping the temperature below −50° C. The reaction mixture is then stirred at room temperature for 3 hours and 1N HCl (5 mL) is added. The organic layer is separated and the aqueous phase is extracted with ethyl acetate. The combined organic phases are dried and the crude product obtained after evaporation of the solvent. Pure product is obtained after flash chromatography using 5% EtOAc in $CH_2Cl_2$.

Ethyl 3-cyclopropylamino-2-(2,4-difluoro-3-chloro-5-nitro-benzoyl)acrylate

Ethyl 5-nitro-3-chloro-2,4-difluoro-benzoyl acetate (4.10 g, 13.3 mmol) is dissolved in a mixture of triethyl orthoformate (3.4 mL, 20 mmol) and acetic anhydride (6 mL, 64 mmol). The reaction mixture is warmed at 120° C. for 3 hours and the remaining volatiles are removed under vacuum. The residue is dissolved in ethanol (15 mL) and the solution is cooled at −5° C. Cyclopropylamine (0.88 mL, 12.7 mmol) is added and the desired product is isolated by filtration and air dried.

Ethyl 1-cyclopropyl-1,4-dihydro-7-fluoro-8-chloro-6-nitro-4-oxo-quinoline-3-carboxylate (Precursor D)

Ethyl 3-cyclopropylamino-2-(2,4-difluoro-3-chloro-5-nitro-benzoyl) acrylate (3.41 g, 9.1 mmol) is dissolved in EtOAc (40 mL) at 0° C. Potassium carbonate (3.9 g, 28 mmol) is added and the reaction mixture is stirred at 0° C. for 2 hours. The mixture is poured into ice water and the desired product is isolated by filtration, washed with water, and air dried.

Precursor Example E

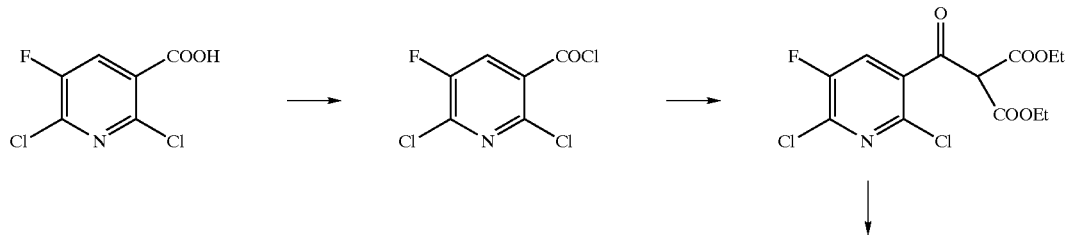

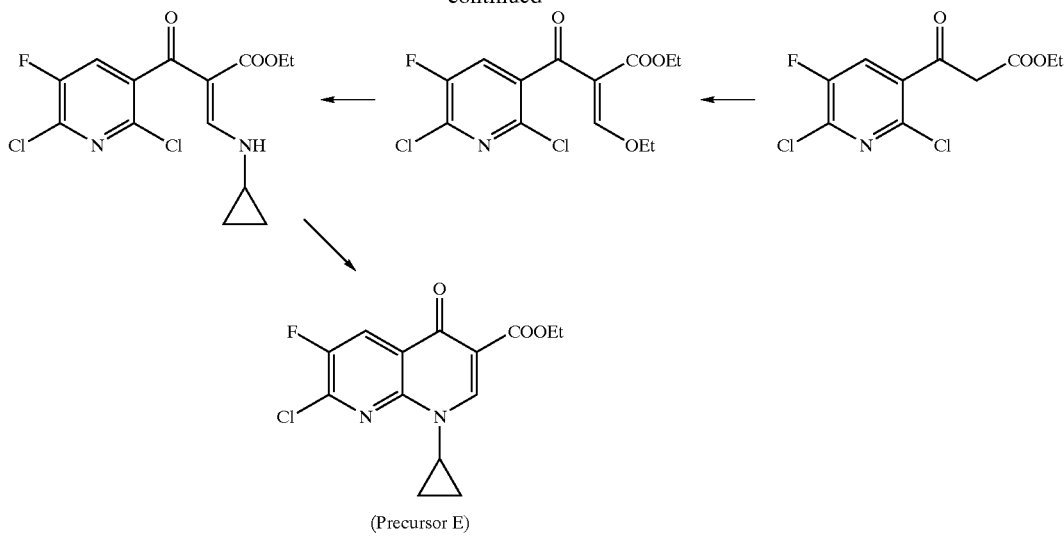

2,6-dichloro-5-fluoro-3-nicotinoyl chloride 2,6-dichloro-5-fluoro-3-nicotinic acid (4 g, 19 mmol) is suspended in $CH_2Cl_2$ and oxalyl chloride (2.72 g, 21 mmol) is added followed by 3 drops of DMF. The mixture is allowed to stir for 3 hours at room temperature and the solvent is evaporated to afford the desired product.

Ethyl-3-(2,6-dichloro-5-fluoropyridinyl)-3-oxo-2-carboxyethyl propanoate

Magnesium turnings (0.44 g, 18 mmol) are added to a mixture of ethanol (1.5 mL, 26 mmol) and carbon tetrachloride (0.15 mL) and diethyl malonate (2.76 mL, 18 mmol) is added over 15 minutes. The temperature is maintained at 50° C. for 2 hours and then cooled at 0° C. 2,6-dichloro-5-fluoro-3-nicotinoyl chloride (4.3 g, 19 mmol) is progressively added keeping the temperature below 5° C. After one hour at room temperature, the mixture is acidified, diluted with water, and extracted with toluene. Evaporation of the solvent affords the desired product.

Ethyl-3-(2,6-dichloro-5-fluoropyridinyl)-3-oxo-propanoate

Ethyl-3-(2,6-dichloro-5-fluoropyridinyl)-3-oxo-2-carboxyethyl propanoate (6 g, 17 mmol) is mixed with water (30 mL) and p-toluenesulfonic acid monohydrate (0.15 g, 0.8 mmol) and heated at 100° C. for one hour. After cooling to room temperature the aqueous solution is extracted with ethyl acetate and the combined organic layers are dried over $Na_2SO_4$. The spent dessicant is removed by filtration and the filtrate concentrated to give the desired product.

Ethyl-3-(2,6-dichloro-5-fluoropyridinyl)-3-oxo-2-ethoxymethylene-propanoate

Ethyl-3-(2,6-dichloro-5-fluoropyridinyl)-3-oxo-propanoate (5 g, 18 mmol) is mixed with triethyl orthofomate (4.3 mL, 26 mmol) and acetic anhydride (4.1 mL, 43 mmol) and the mixture is heated at reflux for 2 hours. The mixture is then concentrated under vacuum to afford the desired product.

Ethyl-3-(2,6-dichloro-5-fluoropyridinyl)-3-oxo-2-cyclopropylaminomethylene-propanoate Ethyl-3-(2,6-dichloro-5-fluoropyridinyl)-3-oxo-2-ethoxymethylene-propanoate (2.65 g, 8 mmol) is dissolved in ethanol (5 mL) and the solution is cooled at 0° C. Cyclopropylamine (0.8 mL, 12 mmol) is added progressively and the mixture is allowed to stir at room temperature for one hour. The desired product is obtained after evaporation of the volatiles.

Ethyl-7-chloro-1-cyclopropyl-6-fluoro-4-oxo-1,4-dihydro-naphthyridine-3-carboxylate (Precursor E)
Ethyl-3-(2,6-dichloro-5-fluoropyridinyl)-3-oxo-2-cyclopropylaminomethylene-propanoate (1.09 g, 3 mmol) is dissolved in acetonitrile (15 mL) and potassium carbonate (840 mg, 6 mmol) is added. The mixture is heated at reflux for 18 hours and poured into water. The precipitate is filtered and purified by flash chromatography using 2% methanol in $CH_2CL_2$.

Precursor Example F

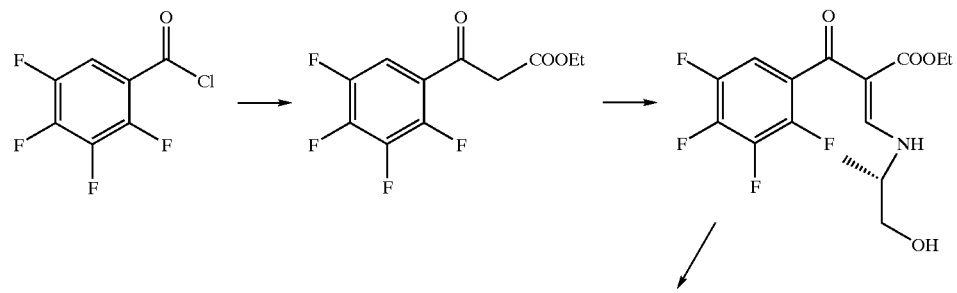

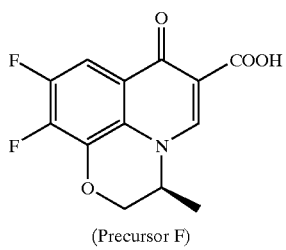
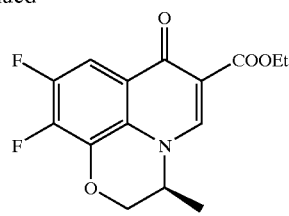

(Precursor F)

Ethyl-3-(2,3,4,5-tetrafluorophenyl)-3-oxo-propanoate

Ethyl hydrogen malonate (26.4 g, 200 mmol) is dissolved in THF (700 mL) and the solution is cooled at −35° C. n-BuLi (160 mL, 2.5 M in hexane, 400 mmol) is added dropwise and the solution is cooled at −58° C. A solution of 2,3,4,5-tetrafluorobenzoyl chloride (21.1 g, 100 mmol) in THF (10 mL) is added and then the reaction is allowed to warm to room temperature. The solution is poured in 1N HCl and extracted with ether. The extracts are washed with a bicarbonate solution, brine and dried over $Na_2SO_4$. The desired product is purified by flash chromatography on silica gel using 15% EtOAc in hexanes.

Ethyl-3-(2,3,4,5-tetrafluorophenyl)-3-oxo-2-[3-amino-2S-methyl-propanol-3-yl]-methylene-propanoate Ethyl-3-(2,3,4,5-tetrafluorophenyl)-3-oxo-propanoate (10 g. 38 mmol) is dissolved in a mixture of triethyl orthoformate (10 mL, 60 mmol) and acetic anhydride (10 mL, 106 mmol) and the solution is heated at reflux for 3 hours. After concentration under vacuum, the residue is dissolved in $CH_2Cl_2$ and cooled at 0° C. 2S-aminopropanol (4.26 g, 55 mmol) is added dropwise and the solution is allowed to warm to room temperature. The product is purified by flash chromatography on silica gel using 25% EtOAc in hexanes.

Ethyl-9,10-difluoro-2,3-dihydro-3S-methyl-7-oxo-7H-pyrido[1,2,3-de]-1,4-benzoxazine-6-carboxylate Ethyl-3-(2,3,4,5-tetrafluorophenyl)-3-oxo-2-[3-amino-2S-methyl-propanol-3-yl]-methylene-propanoate (9.78 g, 28 mmol) is dissolved in DMF (25 mL) and 60% sodium hydride in oil (1.17 g, 29 mmol) is added. After 20 minutes at room temperature, the solution is heated overnight. The solvent is removed under vacuum and the residue is triturated with hexanes and treated with water. The desired product is obtained by filtration.

9,10-difluoro-2,3-dihydro-3S-methyl-7-oxo-7H-pyrido[1,2,3-de]-1,4-benzoxazine-6-carboxylic acid (Precursor F)

Ethyl-9,10-difluoro-2,3-dihydro-3S-methyl-7-oxo-7H-pyrido[1,2,3-de]-1,4-benzoxazine-6-carboxylate (8.2 g, 27 mmol) is dissolved in THF and 10% aqueous KOH (25 mL) is added. The solution is heated at 65° C. for 2 hours. The THF is evaporated and the pH is adjusted to 3 by addition of acetic acid. The desired product is obtained by filtration.

Precursor Example G

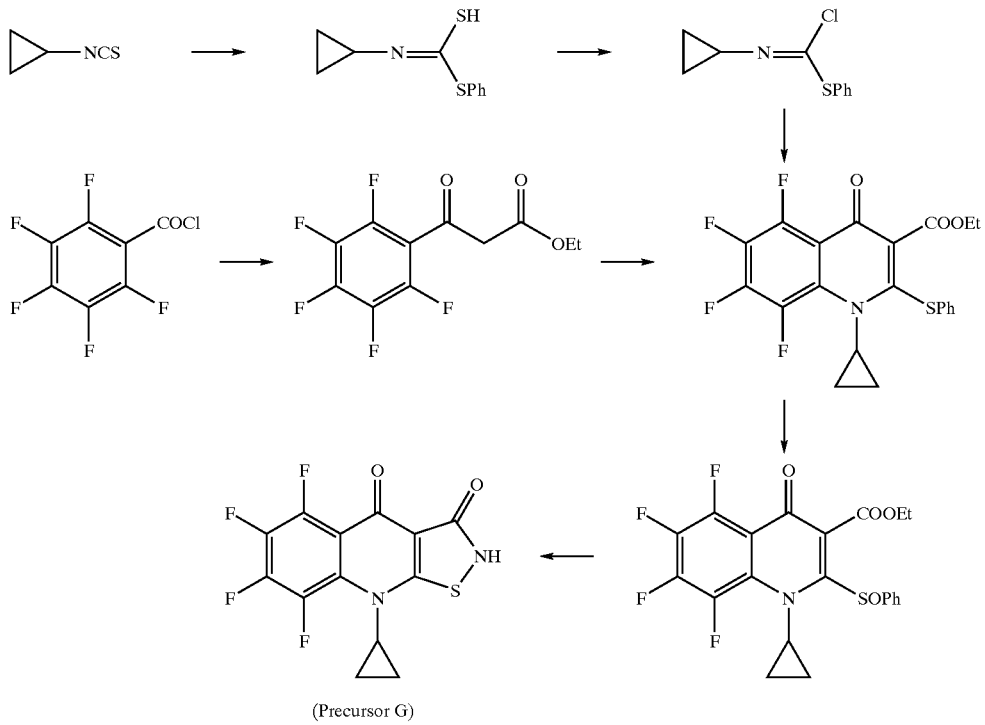

(Precursor G)

Phenyl N-cyclopropyliminomercaptothioformate

N-Cyclopropyl isothiocyanate (5 g, 50 mmol) and thiophenol (5.2 mL, 51 mmol) are mixed together at 0° C. After stirring 30 minutes at 0° C., two drops of triethylamine are added to initiate the reaction. The mixture immediately becomes yellow and slowly solidifies. The white solid is broken apart, collected on a filter, and washed with hexanes to give the desired product.

Phenyl N-cyclopropyliminochlorothioformate

Phosphorus pentachloride (10.5 g, 50 mmol) is added to phenyl N-cyclopropyliminomercaptothioformate, the flask is equipped with a reflux condenser, and the solid mixture is heated at 65° C. under argon. The solids slowly melt to become a yellow solution. The mixture is allowed to stir 6 hr at 65° C., then is cooled to room temperature. The flask is equipped with a distillation apparatus and the desired product is distilled.

2,3,4,5,6-Pentafluorobenzoylacetate

Ethyl hydrogen malonate (33.69 g, 255 mmol) is dissolved in dry THF (640 mL). The mixture is cooled to −78° C. and n-butyllithium (319 mL, 1.6 M in hexanes, 510 mmol) is added at a rapid drop rate such that the internal temperature remains below −30° C. The cooling bath is then removed and the mixture is allowed to warm to −20° C. The reaction is re-cooled to −78° C. and 2,3,4,5,6-pentafluorobenzoyl chloride (25 g, 108 mmol) is added in dry THF (40 mL) via cannula. The yellow solution is allowed to warm to room temperature and stir overnight. The reaction mixture is poured into a vigorously stirring solution of dilute HCl (125 mL) and allowed to stir 1 hour, before the layers are separated and the aqueous layer is extracted with ether. The organic phase is washed with saturated aqueous sodium bicarbonate solution and brine and dried over $MgSO_4$. After concentrating, the desired product is distilled under reduced pressure (5 mm Hg).

Ethyl 1-cyclopropyl-2-phenylthio-5,6,7,8-tetrafluoro-1,4-dihydro-4-oxoquinoline-3-carboxylate 2,3,4,5,6-Pentafluorobenzoylacetate (6.02 g, 21 mmol) is dissolved in dry toluene (100 mL). Dry sodium hydride (0.562 g, 23 mmol) is added under argon and the mixture is allowed to stir 30 minutes. Phenyl N-cyclopropyliminochlorothioformate (6.78 g, 32 mmol) is then added in dry toluene (15 mL). The resulting mixture is heated at 50° C. for 4 hours, then at reflux for 20 hours before being cooled to room temperature and diluted with $CH_2Cl_2$. The organic layer is washed once with water, dried over $MgSO_4$, and concentrated to give a dark oil which is purified by flash chromatography on silica gel using 15% acetone in hexanes.

Ethyl 1-cyclopropyl-2-phenylsulfinyl-5,6,7,8-tetrafluoro-1,4-dihydro-4-oxoquinoline-3-carboxylate Ethyl 1-cyclopropyl-2-phenylthio-5,6,7,8-tetrafluoro-1,4-dihydro-4-oxoquinoline-3-carboxylate (3.38 g, 7.7 mmol) is dissolved in $CH_2Cl_2$ (100 mL). m-Chloroperbenzoic acid (1.9 g, 11 mmol) is added and the solution is allowed to stir at room temperature overnight. The reaction mixture is extracted with sodium bicarbonate, dried over $MgSO_4$ and concentrated under vacuum. The desired product is obtained after purification by flash chromatography on silica gel using 15% acetone in hexanes.

5,6,7,8-tetrafluoro-9-cyclopropyl-1,3,4,9-tetrahydroisothiazolo[5,4-b]quinoline-3,4-dione (Precursor G)

Ethyl 1-cyclopropyl-2-phenylsulfinyl-5,6,7,8-tetrafluoro-1,4-dihydro-4-oxoquinoline-3-carboxylate (0.225 g, 0.496 mmol) is dissolved in THF (15 mL) and the solution is cooled at 0° C. Sodium hydrosulfite (60 mg) dissolved in water (2 mL) is then added followed by a solution of sodium bicarbonate (0.5 g in 10 mL). The solution is stirred at 0° C. for one hour and hydroxylamine-O-sulfonic acid (0.264 g, 2.3 mmol) is added. The solution is allowed to warm at room temperature and after 3 hours is treated with dilute hydrochloric acid. The crude desired product is collected by filtration and purified by crystallization from ethanol.

Precursor Example H

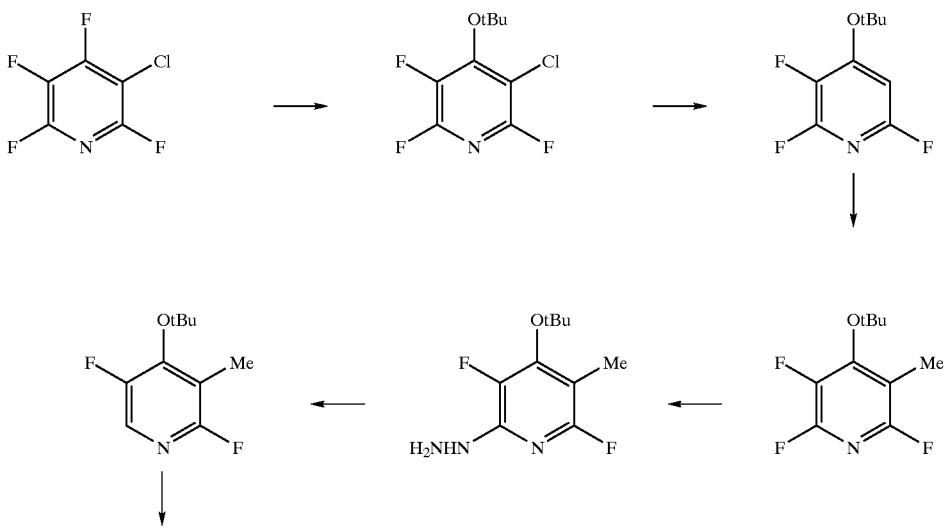

-continued

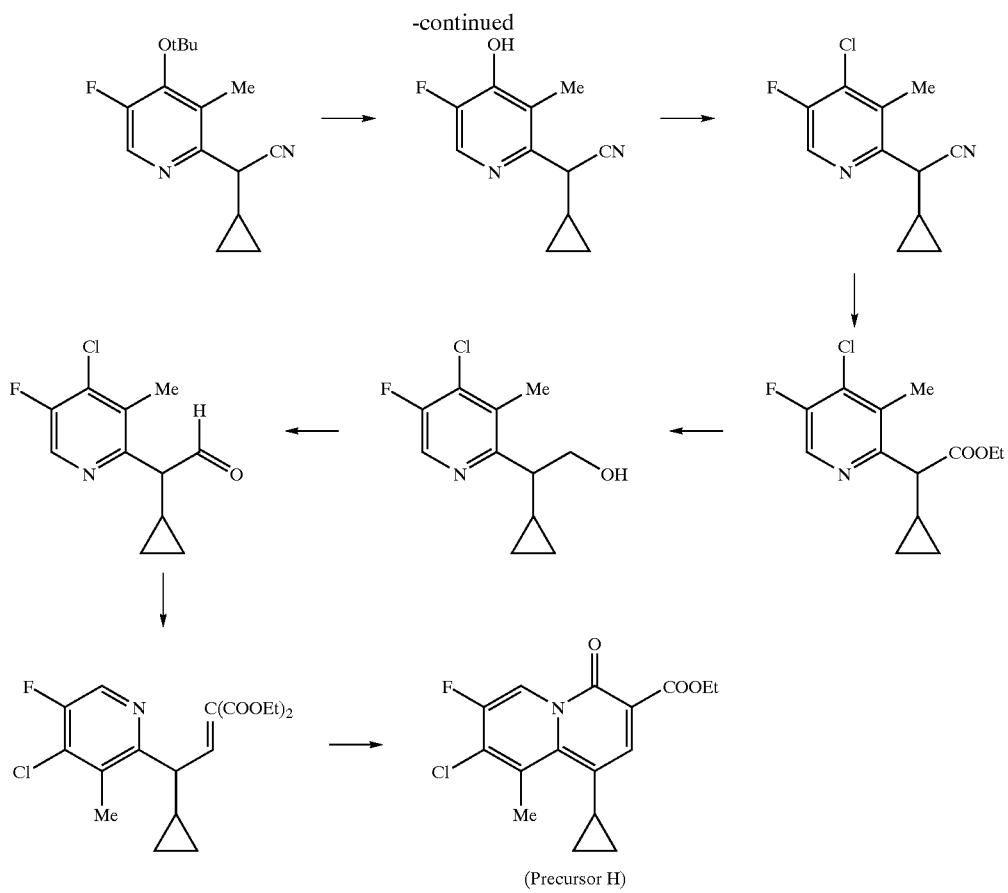

(Precursor H)

4-tert-Butoxy-3-chloro-2,5,6-trifluoropyridine

3-Chloro-2,4,5,6-tetrafluoropyridine (50.0 g, 270 mmol) is dissolved in dry THF (500 mL) and cooled to 0° C. A solution of lithium tert-butoxide (270 mL, 1.0 M in THF, 270 mmol) is added dropwise over 50 minutes and the solution is then allowed to stir an additional 90 min. at 0° C. before warming to room temperature. The reaction mixture is poured into hexanes (1000 mL) and filtered through a pad of Celite®. After concentration via rotary evaporation, the liquid purified by flash chromatography on silica gel using hexanes to isolate the desired compound.

4-tert-Butoxy-2,5,6-trifluoropyridine

Sodium acetate (12.75 g) and 10% Pd/C (18.66 g) are added to a solution of 4-tert-butoxy-3-chloro-2,5,6-trifluoropyridine (31.03 g, 129 mmol) in THF (800 mL) and the mixture is placed under hydrogen (1 atm). The mixture is allowed to stir at room temperature for 48 h. The catalyst is removed by filtration through a pad of Celite®, which is washed with hexanes. After concentration, the residue is purified by flash chromatography on silica gel using 5% Et$_2$O in petroleum ether to isolate the desired compound.

4-tert-Butoxy-2,3,6-trifluoro-5-methylpyridine n-Butyllithium (45.6 mL, 2.5 M in hexanes, 114 mmol) is added via syringe to a solution of dry diisopropylamine (14.93 mL, 107 mmol) in anhydrous THF (300 mL) under argon at −78° C. and the mixture is allowed to stir 20 minutes. A solution of 4-tert-butoxy-2,5,6-trifluoropyridine (15.58 g, 76 mmol) in dry THF (30 mL) is added. Methyl iodide (9.45 mL, 152 mmol) is added via syringe and the cooling bath is removed. After stirring 90 minutes, the slurry is poured into a saturated aqueous ammonium chloride solution (250 mL) and is extracted twice with hexanes. The combined organic layers are washed with water and brine and dried over MgSO$_4$. Evaporation of the solvent provides the desired compound.

4-tert-Butoxy-2,5-difluoro-6-hydrazino-3-methylpyridine

Hydrazine monohydrate (16.6 mL, 342 mmol) is added to a solution of 4-tert-butoxy-2,3,6-trifluoro-5-methylpyridine (13.19 g, 60 mmol) in n-propanol (200 mL) and the resulting solution is heated at reflux under argon for 16 hours. The mixture is cooled to room temperature and the solvent evaporated. The residue is redissolved in CH$_2$Cl$_2$, washed with water, and dried over MgSO$_4$. The desired product is obtained by evaporation of the solvent.

4-tert-Butoxy-2,5-difluoro-3-methylpyridine

Crude 4-tert-butoxy-2,5-difluoro-6-hydrazino-3-methylpyridine is dissolved in methanol (150 mL) and a 20% aqueous sodium hydroxide solution (32 mL) is added. Air is bubbled through the reaction mixture as it is stirred for 48 h. The solvent is removed and the residue is redissolved CH$_2$Cl$_2$. This organic layer is washed once with water and is dried over MgSO$_4$ and the solvent evaporated. The desired product is purified by flash chromatography on silica gel using 5% Et$_2$O in hexanes.

2-(4-tert-Butoxy-5-fluoro-3-methyl-2-pyridinyl)cyclopropaneacetonitrile

Dry diisopropylamine (12.0 mL, 86 mmol) is dissolved in anhydrous THF (80 mL). The solution is cooled at −78° C.

and n-butyllithium (36.6 mL, 2.5 M in hexanes, 92 mmol) is added. After 30 minutes, cyclopropylacetonitrile (3.6 g, 44 mmol) is added in dry THF (20 mL). 4-tert-butoxy-2,5-difluoro-3-methyl-2-pyridine (8.45 g, 42 mmol) in THF (20 mL) is then added. The mixture is allowed to stir 1 hour at −78° C. and 1 hour at room temperature before it is poured into a saturated aqueous ammonium chloride solution (150 mL) and extracted twice with ether. The combined organic layers are washed with brine, dried over $MgSO_4$, and concentrated to give a yellow oil. The oil is purified by flash chromatography on silica gel using 20% EtOAc in hexanes to give the desired product.

2-(4-Hydroxy-5-fluoro-3-methyl-2-pyridinyl) cyclopropaneacetonitrile 2-(4-tert-Butoxy-5-fluoro-3-methyl-2-pyridinyl) cyclopropaneacetonitrile (10.5 g, 40 mmol) is dissolved in neat trifluoroacetic acid (100 mL) and stirred 1 hour at room temperature. The trifluoroacetic acid is then removed under reduced pressure to give the desired product.

2-(4-Chloro-5-fluoro-3-methyl-2-pyridinyl) cyclopropaneacetonitrile

Crude 2-(4-Hydroxy-5-fluoro-3-methyl-2-pyridinyl) cyclopropaneacetonitrile is dissolved in $CH_2Cl_2$ (150 mL) and anhydrous DMF (30.9 mL, 399 mmol) is added followed by phosphorous oxychloride (3.7 mL, 40 mmol). This mixture is stirred for 48 hours at room temperature, then poured into cold water (150 mL) and extracted with $CH_2Cl_2$. The pH of the aqueous layer is raised to 7 with 1 N NaOH. The aqueous layer is extracted twice more with $CH_2Cl_2$ and the combined organic layers are washed once with water, dried over $MgSO_4$, and concentrated. The desired product is purified by flash chromatography on silica gel using 20% EtOAc in hexanes.

Ethyl 2-(4-chloro-5-fluoro-3-methyl-2-pyridinyl) cyclopropaneacetate

Hydrogen chloride gas is bubbled through a solution of 2-(4-chloro-5-fluoro-3-methyl-2-pyridinyl) cyclopropaneacetonitrile (2.91 g, 13 mmol) in ethanol (9 mL) until the weight increases by 3.56 g and then the mixture is heated to boiling. Water (0.32 mL) is added and the mixture is allowed to heat at reflux for 2 hours before cooling it to room temperature and adding more water. The pH is adjusted to 7 with solid sodium bicarbonate and it is extracted with $CH_2Cl_2$. The combined organic layers are washed with water, dried over $MgSO_4$, and concentrated to give a yellow liquid which is purified by flash chromatography on silica gel using 20% EtOAc in hexanes to give the desired product.

2-(4-Chloro-5-fluoro-3-methyl-2-pyridinyl) cyclopropaneethanol

Ethyl 2-(4-chloro-5-fluoro-3-methyl-2-pyridinyl) cyclopropaneacetate (1.31 g, 4.8 mmol) is dissolved in dry THF (10 mL). Lithium aluminum hydride (91.8 mg, 24 mmol) is added to this solution and it is stirred for 1 hour at room temperature. The reaction mixture is quenched with a saturated aqueous solution of sodium potassium tartrate (25 mL) and extracted with ether. The combined organic layers are dried with $MgSO_4$ and concentrated to give the desired product.

2-(4-Chloro-5-fluoro-3-methyl-2-pyridinyl) cyclopropaneacetaldehyde 2-(4-Chloro-5-fluoro-3-methyl-2-pyridinyl) cyclopropaneethanol is dissolved in $CH_2Cl_2$ (5 mL and added to a solution of oxalyl chloride (0.51 mL, 5.8 mmol) and dry DMSO (0.82 mL, 11.6 mmol) in $CH_2Cl_2$ (12 mL) at −78° C. After stirring 15 minutes, triethylamine (3.31 mL, 23.7 mmol) is added and the mixture stirred another 5 minutes at −78° C. and 10 minutes at 0° C. The reaction mixture is then quenched with water and extracted with $CH_2Cl_2$. The combined organic layers are washed with water, dried over $MgSO_4$, and concentrated to give the desired product.

Diethyl[(4-Chloro-5-fluoro-3-methyl-2-pyridinyl) cyclopropanemethylmethylene]-malonate Piperidine (1.14 mL), acetic acid (1.14 mL) and diethyl malonate (3.80 mL, 25 mmol) are added to a solution of 2-(4-Chloro-5-fluoro-3-methyl-2-pyridinyl) cyclopropaneacetaldehyde in ethanol (40 mL) and the reaction mixture is heated at reflux under argon for 4 h. The solvents are removed and the residue is dissolved in ether. The ether layer is washed with water and brine, dried over $MgSO_4$ and concentrated. The desired product is purified by flash chromatography on silica gel using EtOAc/hexanes.

Ethyl 8-chloro-1-cyclopropyl-7-fluoro-9-methyl-4-oxo-4H-quinolizine-3-carboxylate (Precursor H)

A solution of diethyl [(4-Chloro-5-fluoro-3-methyl-2-pyridinyl)cyclopropanemethyl-methylene]malonate (539.1 mg, 1.5 mmol) in diphenyl ether (25 mL) is heated at 220° C. for 45 minutes, then cooled to room temperature. The desired product is purified by flash chromatography on silica gel, using hexane then ethyl acetate as solvents.

Precursor Example I

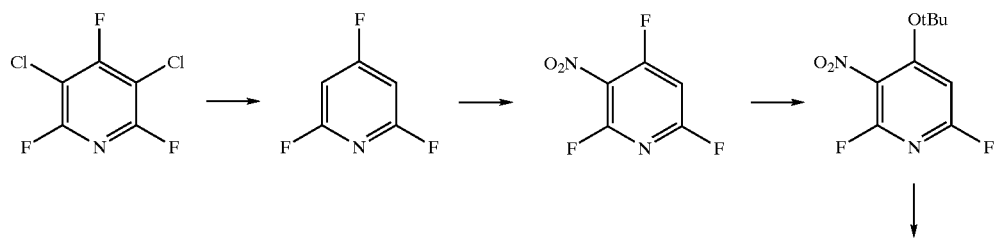

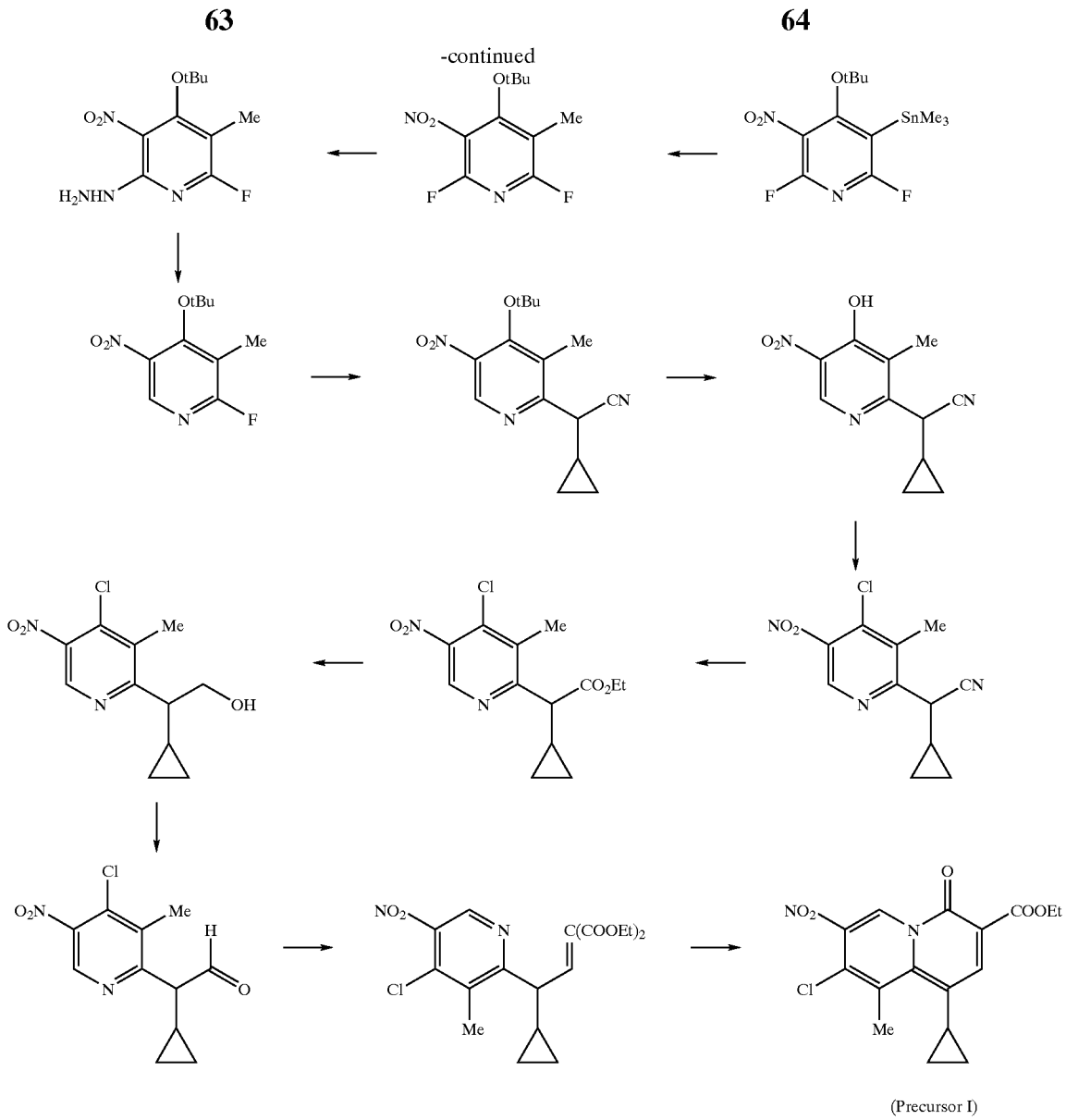

-continued (Precursor I)

2,4,6-Trifluoropyridine
Sodium acetate (12.75 g) and 10% Pd/C (18.66 g) are added to a solution of 3,5-dichloro-2,4,6-trifluoropyridine (26 g, 129 mmol) in THF (800 mL) and the mixture is placed under hydrogen (1 atm). The mixture is stirred at room temperature for 48 hours. The catalyst is removed by filtration through a pad of Celite®, which is washed with hexanes. After concentration, the liquid purified by flash chromatography on silica gel using 5% ether in hexanes to isolate the desired compound.

3-Nitro-2,4,6-Trifluoropyridine
2,4,6-Trifluoropyridine (16.6 g, 125 mmol) is added to a mixture of 35 ml of fuming nitric acid and 45 ml of sulfuric acid at 0° C. The suspension is then stirred at room temperature for 30 minutes and poured onto ice. Filtration affords the desired product.

4-tert-Butoxy-2,6-difluoro-3-nitro-pyridine
3-Nitro-2,4,6-trifluoropyridine (19.6 g, 110 mmol) is dissolved in dry THF (250 mL) and cooled at 0° C. A solution of lithium tert-butoxide (135 mL, 1.0 M in THF, 110 mmol) is added dropwise over 50 minutes and the solution is then stirred an additional 90 min. at 0° C. before warming to room temperature. The reaction mixture is poured into hexanes (500 mL) and filtered through a pad of Celite®. After concentration via rotary evaporation, the liquid is purified by flash chromatography on silica gel using 5% ether in hexanes to isolate the desired compound.

4-tert-Butoxy-2,6-difluoro-3-(trimethylstannyl)-5-nitro-pyridine
To a solution of (tert-butyldimethylsislyl)-tert-butylamine (23 mL, 95.9 mmol) in THF (120 mL) at −78° C. under argon is added n-butyllithium (61.3 mL, 1.5 M in hexane, 91.9 mmol), and the solution is allowed to warm to 0° C. to provide a solution of LiBSBA. In a separate flask, a solution of 4-tert-butoxy-2,4-difluoro-3-nitro-pyridine (17.63 g, 75.9 mmol) in THF (275 mL) is cooled to −78° C. under argon and Me$_3$SnCl (45.7 mL, 2.5 M in THF, 114.3 mmol) is added. The LiBSBA solution is then added dropwise while maintaining an internal temperature below −74° C. The resulting mixture is stirred for 30 min at −78° C. and then is poured into a saturated aqueous ammonium chloride solution (300 mL). The aqueous solution is extracted with hexanes (3×) and the combined organic layers are washed with water and brine, dried over MgSO$_4$, and concentrated. Purification by flash chromatography using EtOAc/hexanes gives the desired product.

4-tert-Butoxy-2,6-difluoro-3-methyl-5-nitro-pyridine

Tris(dibenzylideneacetone)dipalladium (21.1 g, 23.1 mmol), tri-o-tolylphosphine (28.1 g, 91.7 mmol), cuprous chloride (4.55 g, 45.5 mmol), and potassium carbonate (6.35 g, 45.5 mmol) are placed under argon. After addition of DMF (1600 mL), the mixture is stirred for 5 min at room temperature followed by successive additions of solutions of 4-tert-butoxy-2,6-difluoro-3-(trimethylstannyl)-5-nitro-pyridine (17.99 g, 45.5 mmol) in DMF (1200 mL) and methyl iodide in DMF (228 mL, 0.2 M, 45.5 mmol). The resulting mixture is stirred under argon at 50° C. for 90 minutes. After cooling to room temperature, the reaction mixture is filtered and concentrated under reduced pressure by azeotropic removal of DMF with toluene. The residue is purified by flash chromatography on silica gel using 2:1, 1:1, and 2:3 mixtures of hexane and EtOAc as eluents to give the desired product.

4-tert-Butoxy-2-fluoro-6-hydrazino-3-methyl-5-nitro-pyridine

Hydrazine monohydrate (8 mL, 165 mmol) is added to a solution of 4-tert-butoxy-2,6-difluoro-3-methyl-5-nitro-pyridine (8.1 g, 32.8 mmol) in n-propanol (115 mL) and the resulting solution is heated at reflux under argon for 16 h. The mixture is cooled to room temperature and the solvent evaporated. The residue is redissolved in CH$_2$Cl$_2$, washed with water, and dried over MgSO$_4$. The desired product is obtained by evaporation of the solvent.

4-tert-Butoxy-2-fluoro-3-methyl-5-nitro-pyridine

Crude 4-tert-butoxy-2-fluoro-6-hydrazino-3-methyl-5-nitro-pyridine is dissolved in methanol (85 mL) and a 20% aqueous sodium hydroxide solution (18 mL) is added. The reaction mixture is stirred for 48 h while air is bubbled through the mixture. The solvent is removed, the residue is redissolved in CH$_2$Cl$_2$ and the solution is washed once with water and is dried over MgSO$_4$. The spent dessicant is removed by filtration, the solvent removed, and the residue purified by chromatography on silica gel using 5% ether in hexanes.

2-(4-tert-Butoxy-5-nitro-3-methyl-2-pyridinyl) cyclopropaneacetonitrile

Dry diisopropylamine (7.0 mL, 50 mmol) is dissolved in anhydrous THF (45 mL). The solution is cooled to −78° C. and n-butyllithium (20.8 mL, 2.5 M in hexanes, 52 mmol) is added. After 30 minutes, cyclopropylacetonitrile (2.05 g, 25.2 mmol) is added in dry THF (10 mL). 4-tert-Butoxy-2-fluoro-3-methyl-5-nitro-pyridine (5.75 g, 25.2 mmol) in THF (10 mL) is then added. The mixture is stirred 1 hour at −78° C. and 1 hour at room temperature and then is poured into a saturated aqueous ammonium chloride solution (85 mL) and extracted twice with ether. The combined organic layers are washed with brine, dried over MgSO$_4$, and concentrated to give a yellow oil. The oil is purified by flash chromatography on silica gel using 20% ethyl acetate in hexanes to give the desired product.

2-(4-Hydroxy-5-nitro-3-methyl-2-pyridinyl) cyclopropaneacetonitrile 2-(4-tert-butoxy-5-nitro-3-methyl-2-pyridinyl) cyclopropaneacetonitrile (6.0 g, 20.7 mmol) is dissolved in neat trifluoroacetic acid (60 mL) and the mixture is stirred 1 hour at room temperature. The trifluoroacetic acid is then removed by rotary evaporation to give the desired product.

2-(4-Chloro-5-nitro-3-methyl-2-pyridinyl) cyclopropaneacetonitrile

Crude 2-(4-hydroxy-5-nitro-3-methyl-2-pyridinyl) cyclopropaneacetonitrile is dissolved in CH$_2$Cl$_2$ (85 mL) and anhydrous DMF (17.6 mL, 227 mmol) is added followed by phosphorous oxychloride (2.1 mL, 22.5 mmol). This mixture is stirred for 48 hours at room temperature, then poured into cold water (85 mL) and extracted with CH$_2$Cl$_2$. The pH of the aqueous layer is raised to 7 with 1 N NaOH. The aqueous layer is extracted twice more with CH$_2$Cl$_2$ and the combined organic layers are washed once with water, dried over MgSO$_4$, and concentrated. The desired product is purified by flash chromatography using 20% ethyl acetate in hexanes.

Ethyl 2-(4-chloro-5-nitro-3-methyl-2-pyridinyl) cyclopropaneacetate

Hydrogen chloride gas (2.02 g, 55 mmol) is bubbled through a solution of 2-(4-chloro-5-nitro-3-methyl-2-pyridinyl) cyclopropaneacetonitrile (1.85 g, 7.4 mmol) in ethanol (5 mL) and the resulting mixture is heated to boiling. Water (0.18 mL) is added and heating is continued at reflux for 2 h before cooling the mixture to room temperature and adding water. The pH is adjusted to 7 with solid sodium bicarbonate and the aqueous solution is extracted with CH$_2$Cl$_2$. The combined organic layers are washed with water, dried over MgSO$_4$, and concentrated to give a yellow liquid which is purified by flash chromatography on silica gel using 20% ethyl acetate in hexanes to give the desired product.

2-(4-Chloro-5-nitro-3-methyl-2-pyridinyl) cyclopropaneethanol

Ethyl 2-(4-chloro-5-nitro-3-methyl-2-pyridinyl) cyclopropaneacetate (0.82 g, 2.7 mmol) is dissolved in dry THF (6 mL). Lithium aluminum hydride (52.2 mg, 1.4 mmol) is added to this solution and the mixture is stirred 1 hour at room temperature. The reaction mixture is quenched with a saturated aqueous solution of sodium potassium tartrate (15 mL) and the aqueous solution is extracted with ether. The combined organic layers are dried with MgSO$_4$ and concentrated to give the desired product as an oil.

2-(4-Chloro-5-nitro-3-methyl-2-pyridinyl) cyclopropaneacetaldehyde 2-(4-Chloro-5-nitro-3-methyl-2-pyridinyl) cyclopropaneethanol (0.66 g, 2.6 mmol) is dissolved in CH$_2$Cl$_2$ (3 mL) and added to a solution of oxalyl chloride (0.29 mL, 3.3 mmol) and dry DMSO (0.47 mL, 6.6 mmol) in CH$_2$Cl$_2$ (7 mL) at −78° C. After stirring 15 minutes, triethylamine (1.88 mL, 13.5 mmol) is added and the mixture stirred another 5 minutes at −78° C. and 10 minutes at 0° C. The reaction is then quenched with water and extracted with CH$_2$Cl$_2$. The combined organic layers are washed with water, dried over MgSO$_4$, and concentrated to give the desired product.

Diethyl [(4-Chloro-5-nitro-3-methyl-2-pyridinyl) cyclopropanemethylmethylene]-malonate Piperidine (0.65 mL), acetic acid (0.65 mL) and diethyl malonate (2.16 mL, 14.2 mmol) are added to a solution of 2-(4-Chloro-5-nitro-3-methyl-2-pyridinyl) cyclopropaneacetaldehyde (0.65 g, 2.5 mmol) in ethanol (25 mL) and the reaction mixture is heated at reflux under argon for 4 hours. The solvents are removed and the residue is dissolved in ether. The ether layer is washed with water and brine, dried over MgSO₄ and concentrated. The desired product is purified by flash chromatography on silica gel using 20% ethyl acetate in hexanes.

Ethyl 8-chloro-1-cyclopropyl-7-nitro-9-methyl-4-oxo-4H-quinolizine-3-carboxylate (Precursor I)

A solution of diethyl [(4-chloro-5-nitro-3-methyl-2-pyridinyl)cyclopropanemethyl-methylene]malonate (0.33 g, 0.832 mmol) in diphenyl ether (15 mL) is heated at 220° C. for 45 minutes, then is cooled to room temperature. The desired product is purified by flash chromatography on silica gel using a hexane/ethyl acetate gradient.

Precursor Example J

3-Chloro-cyclopropylamino-4,5-difluorobenzoic acid

In a sealed tube, a mixture of 2-bromo-3-chloro-4,5difluorobenzoic acid (7.96 g, 29.3 mmol), cyclopropyl amine (4.20 mL, 58.7 mmol), potassium acetate (5.77 g, 58.6 mmol), cupric acetate monohydrate (0.50 g, 2.5 mmol), and triethylamine (4.9 mL, 35.19 mmol) in isopropyl alcohol is stirred at 80° C. After 16 hours, the reaction mixture is concentrated under vacuum, and the resulting residue is dissolved in EtOAc. The organic layer is washed with 1.0 M hydrochloric acid, water, and brine. The organic layer is dried over MgSO₄ and filtered. The filtrate is concentrated under vacuum and purified by flash chromatography using 5% isopropyl alcohol-1% formic acid-94% CH₂Cl₂ to give the desired product.

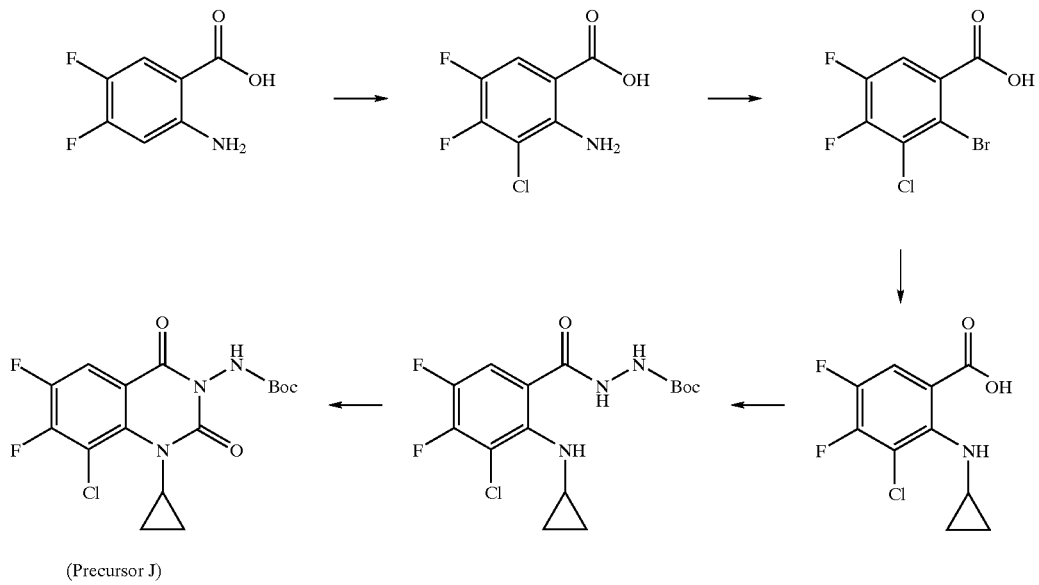

(Precursor J)

3-Chloro-4,5-difluoroanthranilic acid

To a solution of 4,5-difluroroanthranilic acid (12.25 g, 71 mmol) in CH₂CL₂ (125 mL) is added acetic acid (50 mL) and hypochlorous acid tert-butyl ester (8.75 mL, 78 mmol). After 2 hours, the reaction mixture is diluted with EtOAc and washed with water and brine. The organic layer is dried over MgSO₄, filtered, and concentrated. The resulting residue is purified by flash chromatography using 5% isopropyl alcohol-1% formic acid-94% CH₂Cl₂ to give the desired product.

2-Bromo-3-chloro-4,5-difluorobenzoic acid

A solution of cuprous bromide (19.12 g, 85.9 mmol) in acetonitrile (175 mL) is cooled at 0° C. and then tert-butyl nitrite (12.8 mL, 107.3 mmol) and 3-chloro-4,5-difluoranthranilic acid (14.75 g, 71 mmol) are added. The mixture is slowly warmed to room temperature, and after 20 hours, the solvent is removed under vacuum. The resulting residue is dissolved in ethyl acetate and washed with 1.0 M hydrochloric acid, water, and brine. The organic layer is dried over MgSO₄ and filtered. The filtrate is concentrated under vacuum and purified by flash chromatography using 5% isopropyl alcohol-1% formic acid-94% CH₂Cl₂ to give the desired product.

(3-Chloro-2-cyclopropylamino-4,5-difluorobenzoyl)-hydrazinecarboxylic acid tert-butyl ester To a solution of 3-chloro-2-cyclopropylamino-4,5-difluorobenzoic acid (4.18 g, 16.9 mmol) in CH₂Cl₂ (60 mL) is added tert-butyl carbazate (3.34 g, 25.4 mmol) and 1-ethyl-3-(3-dimethylaminopropyl)-carbodiimide (2.43 g, 25.4 mmol). After 16 hours, the reaction mixture is diluted with CH₂Cl₂ and washed with saturated NaHCO₃, water, and brine. The organic layer is dried over MgSO₄ and filtered. The filtrate is concentrated under vacuum and purified by flash chromatography using 33% EtOAc in hexanes to give the desired product.

8-Chloro-1-cyclopropyl-6,7-difluoro-2,4-dioxo-1,4-dihydro-2H-quinazolin-3-yl)carbamic acid tert-butyl ester (Precursor J)

To a solution of (3-chloro-2-cyclopropylamino-4,5-difluorobenzoyl)hydrazinecarboxylic acid tert-butyl ester (3.86 g, 10.7 mmol) in THF (100 mL) is added potassium carbonate (7.38 g, 53.4 mmol) and triphosgene (4.12 g, 13.9 mmol). The reaction mixture is heated at reflux for 90 minutes, cooled to room temperature, and diluted with EtOAc. The organic layer is washed with water and brine, then dried over MgSO₄ and filtered. The filtrate is concentrated under vacuum and purified by flash chromatography using 33% EtOAc in hexanes to give the desired product.

Precursor Example K

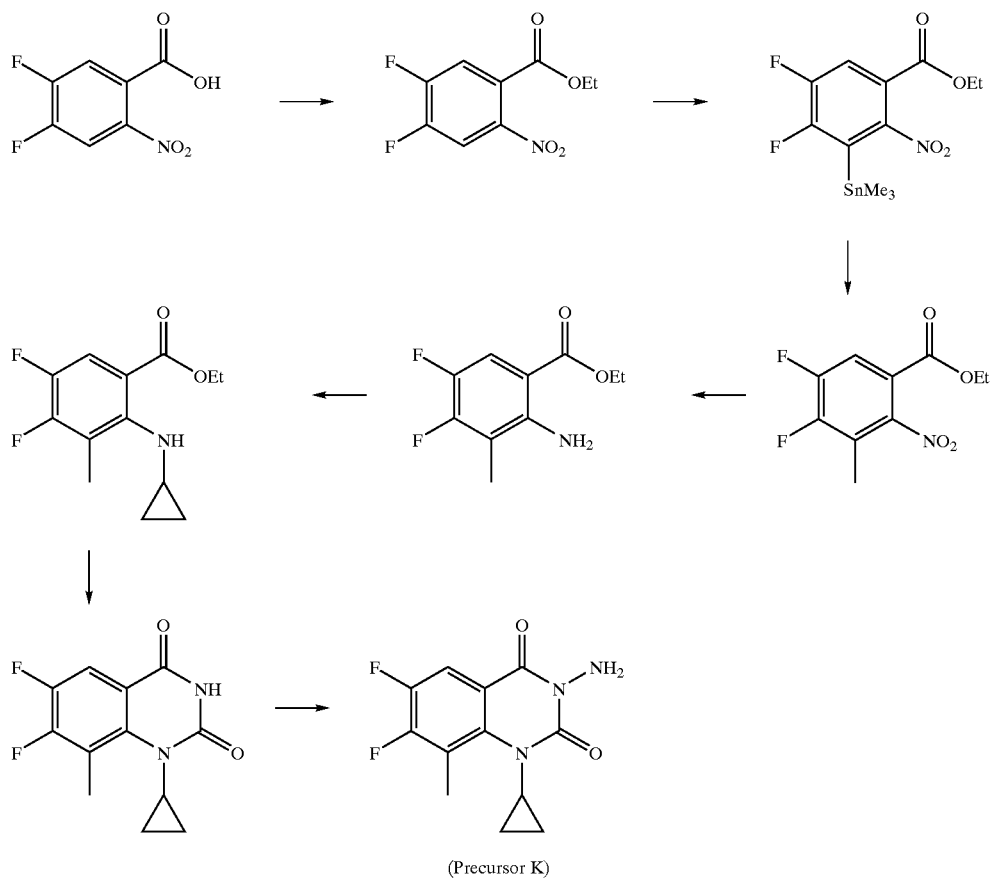

(Precursor K)

4,5-Difluoro-2-nitrobenzoic acid ethyl ester 4,5-Difluoro-2-nitrobenzoic acid (1.93 g, 9.5 mmol) in $CH_2Cl_2$ (30 mL) is cooled to 0° C. under an argon atmosphere and treated with oxalyl chloride (1.0 mL, 11.5 mmol) followed by anhydrous DMF (2 drops). The mixture is warmed to room temperature and stirred for 2 hours. The solution is co-evaporated with toluene to yield an oil that is taken up in $CH_2Cl_2$ (30 ml), cooled to 0° C. under argon, and treated with anhydrous ethanol (6 mL). After 5 hours at room temperature, the solution is poured into saturated $NaHCO_3$ and extracted with chloroform. The organic phase is washed with brine, dried over $Na_2SO_4$, filtered, and concentrated under vacuum to give the desired product.

4,5-Difluoro-3-(trimethylstannyl)-2-nitrobenzoic acid ethyl ester

To a solution of (tert-butyldimethylsilyl)-tert-butylamine (2.88 mL, 12 mmol) in THF (15 mL) at –78° C. under argon is added n-butyllithium (7.67 mL, 1.5 $\underline{M}$ in hexane, 11.5 mmol), and the solution is allowed to warm to 0° C. to provide a solution of LiBSBA. In a separate flask, a solution of 4,5-difluoro-2-nitrobenzoic acid ethyl ester (2.20 g, 9.5 mmol) in THF (35 mL) is cooled to –78° C. under argon and $Me_3SnCl$ (5.7 mL, 2.5 $\underline{M}$ in THF, 14.3 mmol) is added. The LiBSBA solution is then added dropwise while maintaining an internal temperature below –74° C. The resulting mixture is stirred for 30 min at –78° C. and then is partitioned between 1 $\underline{M}$ HCl and $Et_2O$. The aqueous phase is separated and extracted with ether. The combined organic phases are washed with 1 $\underline{M}$ HCl (3x) and brine, dried over $MgSO_4$, and concentrated. Purification by flash chromatography on silica gel using 10% acetone in hexane gives the desired product.

4,5-Difluoro-3-methyl-2-nitrobenzoic acid ethyl ester

Tris(dibenzylideneacetone)dipalladium (3.29 g, 3.6 mmol), tri-o-tolylphosphine (4.38 g, 14.3 mmol), cuprous chloride (0.71 g, 7.1 mmol), and potassium carbonate (0.99 g, 7.1 mmol) are placed under argon. After addition of DMF (250 mL), the mixture is stirred for 5 min at room temperature followed by successive additions of solutions of 4,5-difluoro-3-(trimethylstannyl)-2-nitrobenzoic acid ethyl ester (2.81 g, 7.1 mmol) in DMF (200 mL) and methyl iodide in DMF (35.6 mL, 0.2 $\underline{M}$, 7.1 mmol). The resulting mixture is stirred under argon at 50° C. for 90 minutes. After cooling to room temperature, the reaction mixture is filtered and concentrated under reduced pressure by azeotropic removal of DMF with toluene. The residue is purified by flash chromatography on silica gel using 2:1, 1:1, and 2:3 mixtures of hexane and EtOAc as eluents to give the desired product.

2-Amino-4,5-difluoro-3-methyl-benzoic acid ethyl ester 4,5-Difluoro-3-methyl-2-nitrobenzoic acid ethyl ester (1.26 g, 5.1 mmol) is combined with ethanol (20 mL) and 10% Pd/C catalyst (0.13 g) and the mixture is shaken under hydrogen (40 psi) for 6 hours at room temperature. The catalyst is removed by filtration through Celite and the solvent is evaporated to give the desired product.

2-Cyclopropylamino-4,5-difluoro-3-methylbenzoic acid ethyl ester

To a solution of 2-amino-4,5-difluoro-3-methyl-benzoic acid ethyl ester (1.1 g, 5.1 mmol) in anhydrous ethanol is added molecular sieves (3 Å), acetic acid (3 mL), and [(1-ethoxycyclopropyl)oxy]trimethylsilane (4.1 mL, 20.4 mmol). After 30 minutes, sodium cyanoborohydride (1.63 g, 25.9 mmol) is added, and the reaction mixture is heated at reflux. After 16 hours, the reaction mixture is cooled to room temperature and filtered, the filter cake is washed with ethanol, and the combined filtrate is concentrated under vacuum to afford a viscous oil. The oil is dissolved in ethyl acetate and the solution is washed with 1 $\underline{M}$ HCl, water, and brine. The organic layer is dried over $MgSO_4$, filtered, and the filtrate is concentrated under vacuum to give the desired product as a beige solid.

1-Cyclopropyl-6,7-difluoro-8-methyl-1H-quinazoline-2,4-dione

To a solution of 2-cyclopropylamino-4,5-difluoro-3-methylbenzoic acid ethyl ester (1.24 g, 4.9 mmol) in dry $CH_2Cl_2$ (25 mL) under argon is added chlorosulfonylisocyanate (0.69 g, 4.9 mmol). The solution is left at room temperature for 4 hours and then the solvent is removed under reduced pressure. The residue is cooled at −20° C. and a cold brine solution (25 mL) buffered with $NaHCO_3$ is added. The solution is warmed to room temperature for 1 hour. The volume is reduced by half with a stream of nitrogen, and the solid is collected by filtration. The dry solid is added to a solution of triethylamine (1.13 mL, 8.1 mmol) in THF (50 mL) and the mixture is heated at reflux overnight. The reaction mixture is cooled, the solvent is removed under reduced pressure, and the residue is dissolved in water (22.5 mL) which is then acidified to pH 1–2 with 1 $\underline{M}$ HCl. The resulting precipitate is collected by filtration.

3-Amino-1-cyclopropyl-6,7-difluoro-8-methyl-1H-quinazoline-2,4-dione (Precursor K)

To a solution of 1-cyclopropyl-6,7-difluoro-8-methyl-1H-quinazoline-2,4-dione (0.467 g, 1.85 mmol) in dioxane (1.5 mL) and DMF (1.5 mL) is added NaH (60% dispersion in oil, 89 mg, 2.2 mmol). The solution is heated at 60° C. for 10 minutes and cooled to room temperature. To the cooled solution is added O-(2,4-dinitrophenyl)hydroxylamine (0.368 g, 1.85 mmol), and the solution is heated at 80° C. for 30 minutes. The resulting red solution is cooled to room temperature, poured over crushed ice, and the mixture is extracted with EtOAc. The combined organic layers are dried over $MgSO_4$, filtered, and the solvent removed under reduced pressure. The resulting solid is triturated with $Et_2O$ and air dried to give the desired product.

b. Precursor Preparation—7-Position Moiety:

Precursor Example L

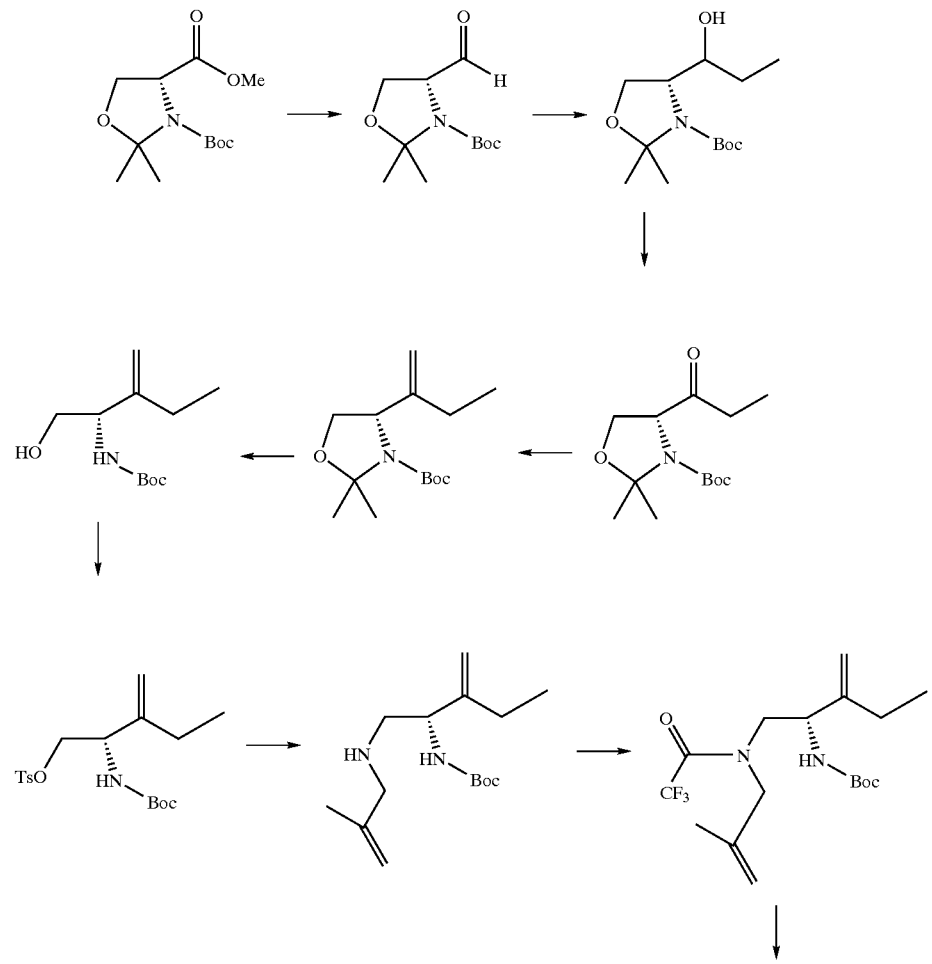

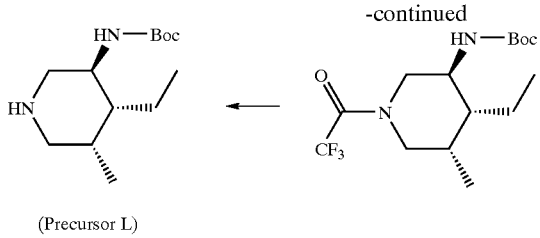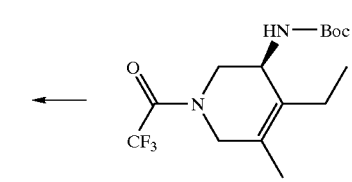

(Precursor L)

3(R)-(tert-butoxycarbonyl)2,2-dimethyl-4-oxazolidinecarboxaldehyde

A solution of methyl 3(R)-(tert-butoxycarbonyl)-2,2-dimethyl-4-oxazolidinecarboxylate (6.5 g, 25.0 mmol) is dissolved in toluene (40 mL) and cooled to −78° C. To it a solution of diisobutylaluminum hydride ("DIBAL") (33.2 mL, 1 M, 33.2 mmol) is added dropwise to maintain the internal temperature under −60° C. After the addition, the resulting solution is stirred at −78° C. for 30 min., and then slowly warmed to 0° C. in 2 hrs. The mixture is quenched by addition of water. The organic layer is separated and the aqueous layer is extracted once with ethyl acetate. The combined extracts are dried over anhydrous MgSO$_4$ and evaporated. The residue is purified by flash chromatography using ethyl acetate-hexanes.

3(R)-(tert-butoxycarbonyl)2,2-dimethyl-4-(1-hydroxy-propyl)-oxazolidine

To a solution of 3(R)-(tert-butoxycarbonyl)2,2-dimethyl-4-oxazolidinecarboxaldehyde (5.04 g, 22.0 mmol) in THF (26 mL) is added a solution of EtMgBr (26.4 mL, 1 M in THF) dropwise at −78° C. After the addition, the resulting solution is allowed to warm to 0° C. in 1.5 hr and water is added to quench the reaction. The mixture is partitioned between brine and EtOAc and the aqueous layer is extracted further with EtOAc (2×). The combined extracts are dried over MgSO$_4$ and evaporated under reduced pressure. The crude product is purified by flash chromatography with EtOAc-Hexanes to give the desired product.

3(R)-(tert-butoxycarbonyl)2,2-dimethyl-4-(1-oxo-propyl)-oxazolidine

A solution of oxalyl chloride (2.08 mL, 23.8 mmol) in CH$_2$Cl$_2$ (70 mL) is cooled in a dry ice/acetone bath and dimethyl sulfoxide (3.53 mL, 49.7 mmol) is added to it dropwise. After stirring at that temperature for 5 min, a solution of 3(R)-(tert-butoxycarbonyl)2,2-dimethyl-4-(1-hydroxy-propyl)-oxazolidine (5.15 g 19.9 mmol) in CH$_2$Cl$_2$ is added at such a rate that the internal temperature stays under −65° C. The resulting mixture is stirred at −78° C. for 30 min, and triethylamine (13.8 mL, 99 mmol) is added in one portion. Stirring is continued for additional 5 min. The cold bath is removed and the reaction temperature is allowed to rise to room temperature over 30 min. Water is added to quench the reaction. The organic layer is separated and the aqueous layer is extracted with CH$_2$Cl$_2$ (2×). The combined extracts are washed with brine and dried over MgSO$_4$ and evaporated under reduced pressure. The residue is purified by flash chromatography on silica using EtOAc-Hexanes.

3(S)-(tert-butoxycarbonyl)2,2-dimethyl-4-(1-buten-2yl)-oxazolidine

To a suspension of (CH$_3$)PPh$_3$Br (8.59 g, 24 mmol) in anhydrous THF (40 mL) is added t-BuOK (2.7 g, 24 mmol) in one portion at room temperature. After stirring for 10 min, the yellow mixture is treated with a solution of 3(R)-(tert-butoxycarbonyl)2,2-dimethyl-4-(1-oxo-propyl)-oxazolidine (4.12 g, 16.0 mmol) in THF. The mixture is stirred for an additional 10 min. and is then partitioned between brine and EtOAc. The organic layer is separated and the aqueous layer is extracted with EtOAc (2×). The combined extracts are dried over MgSO$_4$ and evaporated under reduced pressure. The residue is treated with ether and the white solid which forms is removed by filtration. The filtrate is evaporated and the residue is purified by flash chromatography on silica gel using EtOAc-Hexanes.

2(S)-tert-butoxycarbonylamino-3-methylene-pentanol

A solution of 3(S)-(tert-butoxycarbonyl)2,2-dimethyl-4-(1-buten-2yl)-oxazolidine (3.25 g, 12.7 mmol) and p-TsOH.H$_2$O (0.484 g, 2.5 mmol) in MeOH (100 mL) is heated at 50–60° C. for 18 hr. After cooling, the solvent is evaporated to ⅓ of its volume and diluted with EtOAc. The mixture is washed with saturated NaHCO$_3$ solution. The organic layer is separated and the aqueous layer is extracted with EtOAc (2×). The combined extracts are dried over anhydrous MgSO$_4$ and evaporated. The residue is purified by flash chromatography on silica gel with EtOAc-Hexanes.

2(S)-tert-butoxycarbonylamino-3-methylene-1-(4-toluenesulfonylyloxy)-pentane A solution of 2(S)-tert-butoxycarbonylamino-3-methylene-pentanol (1.38 g. 6.4 mmol), p-toluenesulfonyl chloride (1.46 g, 7.7 mmol) and triethylamine (1.07 mL, 7.7 mmol) in CH$_2$Cl$_2$ (20 mL) is heated at reflux for 3 hours. After cooling, the solution is washed with a saturated solution of sodium bicarbonate, 1% aqueous HCl, and water and the organic phase dried over anhydrous MgSO$_4$ and evaporated. The residue is purified by flash chromatography on silica gel using EtOAc-hexanes.

2(S)-tert-butoxycarbonylamino-3-methylene-N-(2-methyl-2-propenyl)-pentylamine A solution of 2-tert-butoxycarbonylamino-3-methylene-1-(4-toluenesulfonylyloxy)-pentane (1.95 g, 5.3 mmol) and methallylamine (2.34 mL, 26.4 mmol) was heated at 45° C. for 4 hrs. The excess reagent was distilled in vacuum. The residue was purified by flash chromatography on silica gel using CH$_2$Cl$_2$-MeOH.

2(S)-tert-butoxycarbonylamino-3-methylene-N-(2-methyl-2-propenyl)-N-trifluoroacteyl-pentylamine A solution of 2(S)-tert-butoxycarbonylamino-3-methylene-N-(2-methyl-2-propenyl)-pentylamine (1.27 g, 4.7 mmol), trifluoroacetic anhydride (0.74 mL, 5.2 mmol) and Et$_3$N (0.79 mL, 5.7 mmol) is stirred at <10° C. for 30 min. under argon. The mixture is washed with saturated NaHCO$_3$, dried over anhydrous MgSO$_4$ and evaporated. The residue is purified by flash chromatography on silica gel using EtOAc-hexanes.

1,2,3,6-tetrahydro-3(S)-tert-butoxycarbonylamino-4-ethyl-5-methyl-1-trifluoroacetyl-pyridine 2(S)-tert-butoxycarbonylamino-3-methylene-N-(2-methyl-2-propenyl)-N-trifluoroacteyl-pentylamine (1.46 g, 4.0 mmol) and Grubb's catalyst (benzylidene-bis(tricyclohexylphosphine)dichlororuthenium, 0.329 g, 0.4 mmol) are dissolved in $CH_2Cl_2$ (150 mL) and the solution is heated at reflux under argon for 20 hrs. The solvent is evaporated and the residue is purified by flash chromatography on silica gel using EtOAc-hexanes.

3(S)-tert-butoxycarbonylamino-4(R)-ethyl-5(S)-methyl-1-trifluoroacetyl-piperidine A mixture of 1,2,3,6-tetrahydro-3-tert-butoxycarbonylamino-4-ethyl-5-methyl-1-trifluoroacetyl-pyridine (1.08 g, 3.2 mmol) and $PtO_2$ (0.062 g) in EtOH (60 mL) is treated with $H_2$ (1 atm) for 48 hr. The catalyst is removed by filtration and the filtrate is evaporated. The crude product is purified by flash chromatography using 10–20% EtOAc-hexanes.

3(S)-tert-butoxycarbonylamino-4(R)-ethyl-5(S)-methyl-piperidine (Precursor L)

A mixture of 3(S)-tert-butoxycarbonylamino-4(R)-ethyl-5(S)-methyl-1-trifluoroacetyl-piperidine (1.05 g, 3.1 mmol) and $K_2CO_3$ (1.8 g, 13 mmol) in MeOH (40 mL) and $H_2O$ (10 mL) is heated at reflux for 30 min. The solid is removed by filtration and the filtrate is concentrated. The residue is partitioned between $H_2O$ and $CH_2Cl_2$. The organic layer is separated and the aqueous layer is extracted with $CH_2Cl_2$. The combined extracts are dried over anhydrous $MgSO_4$ and evaporated.

Precursor Example M to the residue, and the volatiles are removed by evaporation. This process is repeated twice more to give the desired product.

2(S)-tert-Butoxycarbonylamino-pentanedioic acid dimethyl ester

A solution of 2(S)-amino-pentanedioic acid dimethyl ester hydrochloride (24.3 g, 115 mmol) in methanol (150 mL) is treated with triethylamine (31.5 mL, 226 mmol). Solid di-tert-butyl dicarbonate (33 g, 151 mmol) is added. After 18 hours the solvent is removed and the residue is dissolved in $CH_2Cl_2$. The solution is washed twice with 1N HCl, once with brine and dried over $Na_2SO_4$. The spent dessicant is removed and the solvent is evaporated to give the desired product.

2(S)-tert-Butoxycarbonylamino-4(S)-methyl-pentanedioic acid dimethyl ester

A solution of lithium hexamethyldisilylazide (152.6 mL, 1M in THF, 152.6 mmol) is cooled under argon in a dry ice/acetone bath. A solution of 2(S)-tert-butoxycarbonylamino-pentanedioic acid dimethyl ester (20 g, 72.6 mol) in THF (200 mL) is added via cannula, maintaining the temperature below −60° C. After 30 minutes at −78° C. methyl iodide (9 mL, 145 mmol) is added as rapidly as possible via cannula. The reaction mixture is stirred −78° C. for 4.5 hour and then quenched with 1 N HCl (190 mL). The aqueous layer is extracted with EtOAc (3×350 mL). The combined extracts are washed with saturated $NaHCO_3$ and brine, dried over $Na_2SO_4$, and concen-

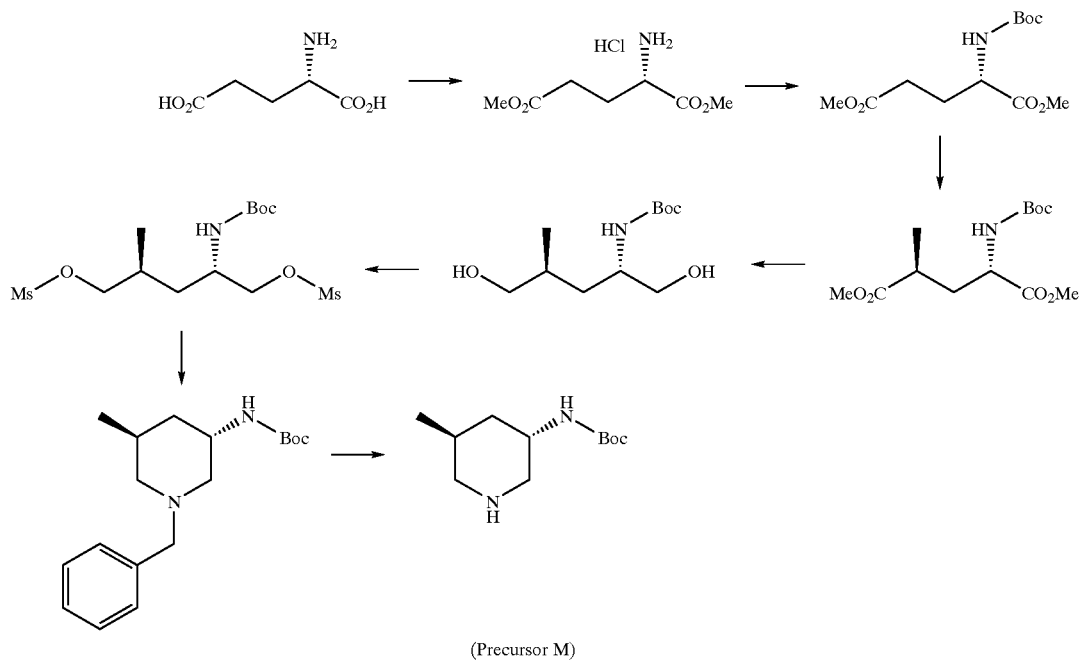

(Precursor M)

2(S)-Amino-pentanedioic acid dimethyl ester hydrochloride

A suspension of L-glutamic acid (18.0 g, 122 mmol) in methanol (120 mL) is cooled in a ice bath. The mixture is treated dropwise with thionyl cholride (12.45 mL, 171 mmol) and the mixture is allowed to stir at room temperature for 18 hours. The reaction is concentrated, toluene is added trated to give a yellow oil which is purified by flash chromatography using 20% EtOAc/hexanes.

(4-Hydroxy-1(S)-hydroxymethyl-3(S)-methyl-butyl)-carbamic acid tert-butyl ester A solution of 2(S)-tert-butoxycarbonylamino-4(S)-methyl-pentanedioic acid dimethyl ester (10.85 g, 37.5 mmol) in 1:1 EtOH/THF (250 mL) is treated with $CaCl_2$ (16.65 g, 150 mmol) and the resulting slurry is cooled under argon in an ice bath. To this mixture is added NaBH$_4$ (11.35 g, 300 mmol) portionwise. After 1 hour the ice bath is removed and the reaction mixture is allowed to stir at room temperature for 16 hours. The mixture is quenched with 10% Na$_2$CO$_3$ and water and the resulting thick, white slurry is extracted with EtOAc (3×). The combined organic layers are washed with brine, dried over Na$_2$SO$_4$, and concentrated to give the desired product.

Methanesulfonic acid 2(S)-tert-butoxycarbonylamino-5-methanesulfonyloxy-4(S)-methyl-pentyl ester A solution of (4-hydroxy-1(S)-hydroxymethyl-3(S)-methyl-butyl)-carbamic acid tert-butyl ester (8.75 g 37.5 mmol) in CH$_2$Cl$_2$ (130 mL) is cooled under argon in an ice bath and (5(S)-Methyl-piperidin-3(S)-yl)-carbamic acid tert-butyl ester (Precursor M)

To a solution of (1-benzyl-5(S)-methyl-piperidin-3(S)-yl)-carbamic acid tert-butyl ester (9.8 g, 32.2 mmol) in EtOH (300 mL) is added 10% Pd/C (1 g). The mixture is treated with hydrogen (30 psi) on a Parr apparatus for 16 hours. The reaction mixture is filtered through Celite, the filtrate concentrated, and the residue purified by flash chromatography on silica gel using 10% MeOH/CHCl$_3$ containing 1% NH$_4$OH to give the desired product.

Precursor Example N

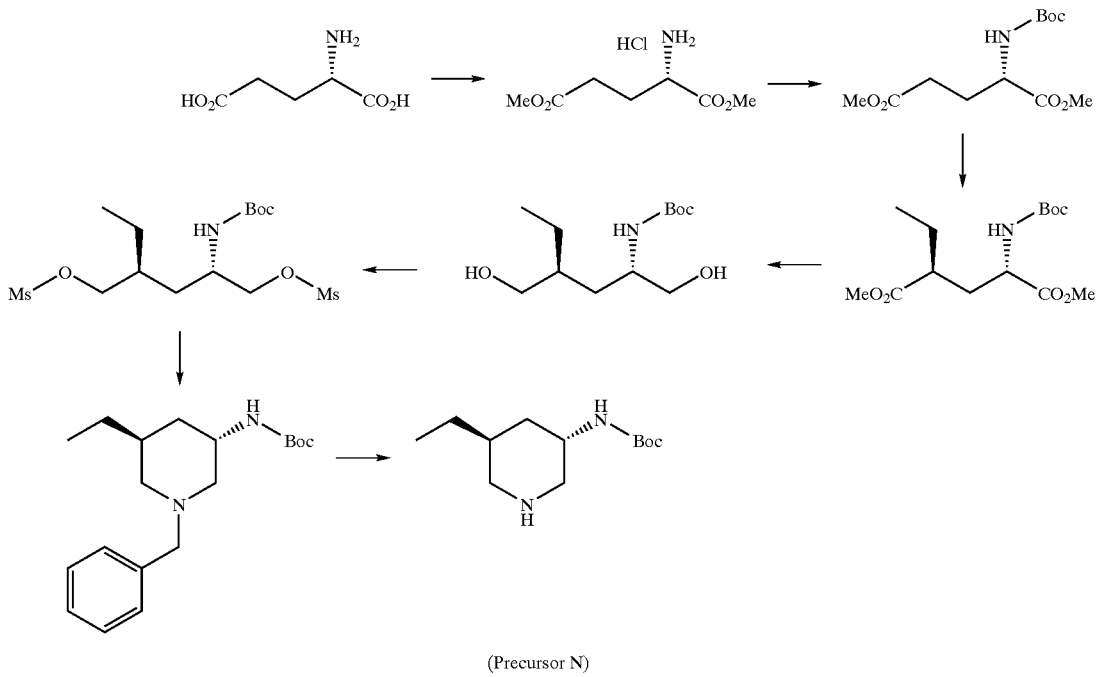

(Precursor N)

triethylamine (20.9 mL, 150 mmol) is added via syringe. Methanesulfonyl chloride (8.7 mL, 112 mmol) is added dropwise and the mixture is stirred for 1 hour at 0° C. The reaction is diluted with CH$_2$Cl$_2$, washed with saturated NaHCO$_3$ and brine, dried over Na$_2$SO$_4$, and concentrated to the desired product.

(1-Benzyl-5(S)-methyl-piperidin-3(S)-yl)-carbamic acid tert-butyl ester

A solution of methanesulfonic acid 2(S)-tert-butoxycarbonylamino-5-methanesulfonyloxy-4(S)-methyl-pentyl ester (14.6 g, 37.5 mmol) in benzylamine (81.9 mL, 750 mmol) is heated 70° C. for 24 hours. The mixture is then cooled to room temperature and poured into 1 N NaOH (500 ml). The resulting oily, aqueous mixture is extracted with hexanes (3×300 ml). The combined hexanes extracts are dried over MgSO4, and the volatiles are removed in vacuo to give an oil which is purified by flash chromatography using a 1–10% gradient of EtOAc/hexanes.

2(S)-Amino-pentanedioic acid dimethyl ester hydrochloride

A suspension of L-glutamic acid (6.00 g, 40.7 mmol) in methanol (40 mL) is cooled in a ice bath. The mixture is treated dropwise with thionyl chloride (4.15 mL, 56.9 mmol) and the reaction mixture is stirred at room temperature for 18 hours. The volatiles are then removed by evaporation in vacuo, toluene is added to the residue and is evaporated. This process is repeated twice to give the desired product.

2(S)-tert-Butoxycarbonylamino-pentanedioic acid dimethyl ester

A solution of 2(S)-amino-pentanedioic acid dimethyl ester hydrochloride (8.12 g, 38.4 mmol) in methanol (50 mL) is treated with triethylamine (10.5 mL, 75.3 mmol) and solid di-tert-butyl dicarbonate (10.91 g, 50.0 mmol). After 18 hours the solvent is removed, the residue is dissolved in CH$_2$Cl$_2$, and the solution is washed with 1N HCl (2×10 mL) and brine (1×5 mL). After drying the solution over Na$_2$SO$_4$ and removing the spent dessicant by filtration, the solvent is evaporated to leave the desired product.

2(S)-tert-Butoxycarbonylamino-4(S)-ethyl-pentanedioic acid dimethyl ester

A solution of lithium bis(trimethylsilyl)amide (10.5 mL, 1 M in THF, 10.5 mmol) is cooled in a dry ice/acetone bath. A solution of 2(S)-tert-butoxycarbonylamino-pentanedioic acid dimethyl ester (1.38 g, 5.0 mmol) in THF (15 mL) is added dropwise, maintaining the temperature below −70° C. After 30 minutes ethyl iodide (1.2 mL, 15.0 mmol) is added dropwise. The reaction mixture is stirred for 1 hour and is then quenched with 1 N HCl (10 mL). The aqueous layer is extracted EtOAc (3×5 mL) and the combined extracts are washed with brine and dried over $Na_2SO_4$. The spent dessicant is removed by filtration and the volatiles evaporated under reduced pressure to leave an oil which is purified by chromatography using 15 to 25% EtOAc/hexanes.

(4-Hydroxy-1(S)-hydroxymethyl-3(S)-ethyl-butyl)-carbamic acid tert-butyl ester A solution of 2(S)-tert-butoxycarbonylamino-4(S)-ethyl-pentanedioic acid dimethyl ester (0.69 g, 2.3 mmol) in 1:1 EtOH/THF (16 mL) is treated with $CaCl_2$ (1.01 g, 9.1 mmol) and cooled in an ice bath. To this mixture is added $NaBH_4$ (0.69 g, 18.2 mmol) all at once. After 1 hour the ice bath is removed and the reaction is stirred at room temperature for 16 hours. The reaction mixture is quenched with saturated $Na_2CO_3$ and water and the aqueous layer is extracted with EtOAc (3×). The combined extracts are washed with brine and dried over $Na_2SO_4$ to give the desired product upon solvent removal.

Methanesulfonic acid 2(S)-tert-butoxycarbonylamino-5-methanesulfonyloxy-4(S)-methyl-pentyl ester A solution of (4-hydroxy-1(S)-hydroxymethyl-3(S)-ethyl-butyl)-carbamic acid tert-butyl ester (0.53 g, 2.1 mmol) in $CH_2Cl_2$ (8 mL) is treated with triethylamine (1.1 mL. 7.9 mmol) and is cooled in an ice bath. Methanesulfonyl chloride (0.48 mL, 6.2 mmol) is added dropwise. After 1 hour the reaction mixture is diluted with $CH_2Cl_2$, the organic layer is washed with saturated $NaHCO_3$ and brine, and is dried over $Na_2SO_4$. The spent dessicant is removed by filtration and the solvent is removed by evaporation under reduced pressure to give the desired product.

(1-Benzyl-5(S)-ethyl-piperidin-3(S)-yl)-carbamic acid tert-butyl ester

A solution of methanesulfonic acid 2(S)-tert-butoxycarbonylamino-5-methanesulfonyloxy-4(S)-methyl-pentyl ester (0.72 g, 1.8 mmol) in $CH_2Cl_2$ (8 mL) is treated with benzylamine (1.1 mL, 10.0 mmol) and the mixture is heated at reflux for 24 hours. The reaction mixture is then cooled to room temperature and diluted with chloroform. The organic solution is washed with 5% citric acid and brine and is dried over $Na_2SO_4$. The spent dessicant is removed by filtration and the solvent is removed by evaporation under reduced pressure to give the desired product.

(5(S)-Ethyl-piperidin-3(S)-yl)-carbamic acid tert-butyl ester (Precursor N)

To a solution of (1-benzyl-5(S)-ethyl-piperidin-3(S)-yl)-carbamic acid tert-butyl ester (0.125 g, 0.393 mmol) in EtOH (4 mL) is added 10% $Pd(OH)_2/C$ (0.075 g). The mixture is placed under a hydrogen atmosphere (balloon) and is stirred for 18 hours. The reaction mixture is filtered through Celite and the filtrate concentrated to give the desired product.

Precursor Example O

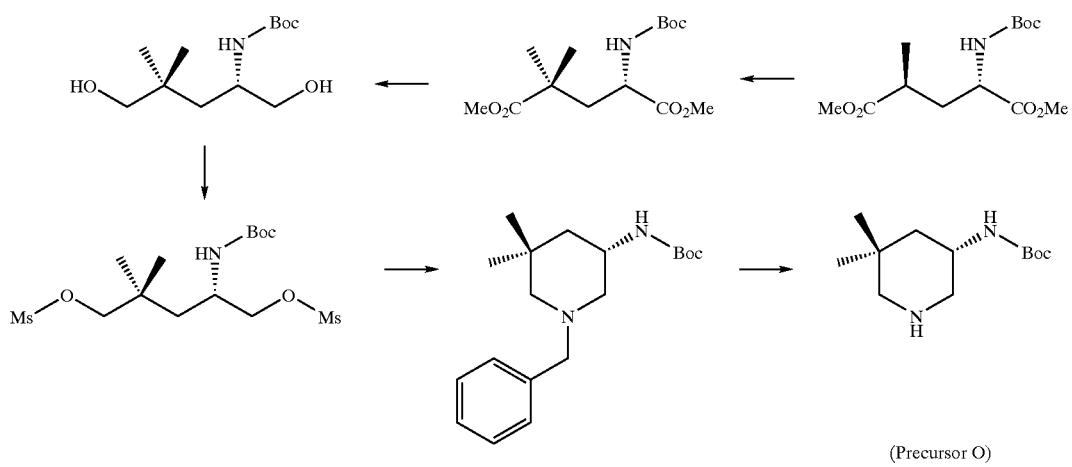

(Precursor O)

4(S)-tert-Butoxycarbonylamino-2,2-dimethyl-pentanedioic acid dimethyl ester

To a stirred solution of potassium bis(trimethylsilylamide) (44.4 mL, 0.5 M in toluene, 22.2 mmol) in dry THF (22 mL) at −78° C. is added a solution of 2(S)-tert-butoxycarbonylamino-4(S)-methyl-pentanedioic acid dimethyl ester (2.14 g, 7.4 mmol) in dry THF (26 mL) over a 5 min. period under an argon atmosphere. The resulting pale yellow solution is stirred at −78° C. for 1 hour and then methyl iodide (1.38 mL, 22.2 mmol) is added. Stirring is continued at −78° C. for 0.5 h, then the white slurry is poured into a saturated solution of $NH_4Cl$ (200 mL), and the resulting mixture is extracted with $Et_2O$ (3×150 mL). The ether extracts are combined, dried over $Na_2SO_4$, concentrated in vacuo, and purified by flash chromatography using 15% EtOAc/Hexanes to give the desired product.

(4-Hydroxy-1(S)-hydroxymethyl-3,3-dimethyl-butyl)-carbamic acid tert-butyl ester A solution of 4(S)-tert-butoxycarbonylamino-2,2-dimethyl-pentanedioic acid dimethyl ester (1.97 g, 6.5 mmol) in 1:1 EtOH/THF (45 mL) is treated with $CaCl_2$ (2.89 g, 26.0 mmol) and the resulting slurry is cooled under argon in an ice bath. To this mixture is added $NaBH_4$ (1.97 g, 52.1 mmol) portionwise. After 1 hour the ice bath is removed and the reaction mixture is allowed to stir at room temperature for 16 hours. The mixture is quenched with 10% Na₂CO₃ and water and the resulting thick, white slurry is extracted with EtOAc (3×). The combined organic layers are washed Precursor Example P

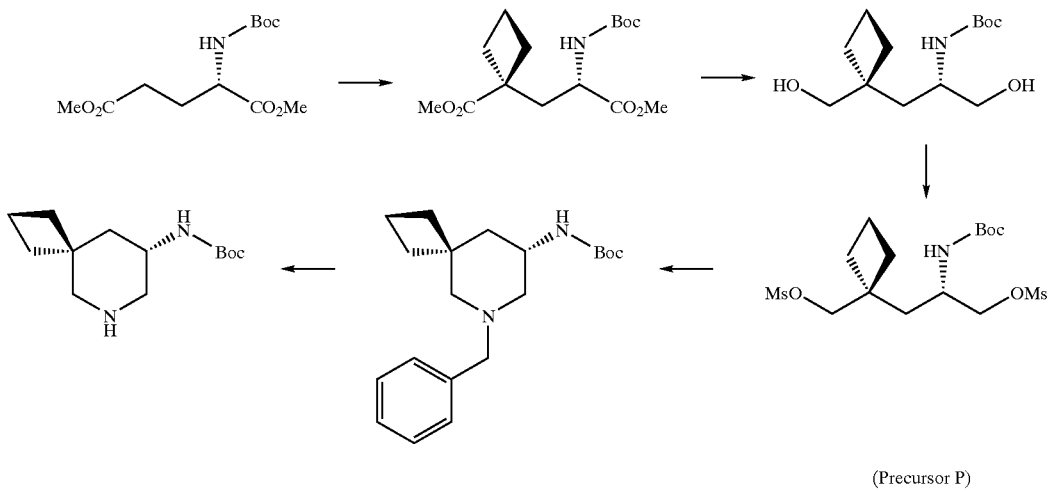

(Precursor P)

with brine, dried over Na₂SO₄, and concentrated to give the desired product.

Methanesulfonic acid 2(S)-tert-butoxycarbonylamino-5-methanesulfonyloxy-4,4-dimethyl-pentyl ester A solution of (4-hydroxy-1(S)-hydroxymethyl-3-dimethyl-butyl)-carbamic acid tert-butyl ester (1.56 g, 6.3 mmol) in CH₂Cl₂ (25 mL) is cooled under argon in an ice bath and triethylamine (3.5 mL, 25.1 mmol) is added via syringe. Methanesulfonyl chloride (1.5 mL, 19.4 mmol) is added dropwise and the mixture is stirred for 1 hour at 0° C. The reaction mixture is diluted with CH₂Cl₂, washed with saturated NaHCO₃ and brine, dried over Na₂SO₄, and concentrated to give the desired product.

(1-Benzyl-5,5-dimethyl-piperidin-3(S)-yl)-carbamic acid tert-butyl ester

A solution of methanesulfonic acid 2(S)-tert-butoxycarbonylamino-5-methanesulfonyloxy-4-di-methyl-pentyl ester (2.55 g, 6.3 mmol) in benzylamine (15 mL, 137 mmol) is heated 70° C. for 24 hours. The mixture is then cooled to room temperature and poured into 1 N NaOH (45 ml). The resulting oily, aqueous mixture is extracted with hexanes (3×25 ml). The combined hexanes extracts are dried over MgSO₄, and the volatiles are removed in vacuo to give an oil which is purified by flash chromatography using a 1–10% gradient of EtOAc/hexanes.

(5,5-Dimethyl-piperidin-3(S)-yl)-carbamic acid tert-butyl ester (Precursor O)

To a solution of (1-benzyl-5-dimethyl-piperidin-3(S)-yl)-carbamic acid tert-butyl ester (0.66 g, 2.1 mmol) in EtOH (20 mL) is added 10% Pd/C (0.19 g). The mixture is treated with hydrogen (30 psi) on a Parr apparatus for 16 hours. The reaction mixture is filtered through Celite, the filtrate concentrated, and the residue purified by flash chromatography on silica gel using 10% MeOH/CHCl₃ containing 1% NH₄OH to give the desired product.

1-(2-tert-Butoxycarbonylamino-2-methoxycarbonyl-ethyl)-cyclobutanecarboxylic acid methyl ester Sodium hydride (60% in mineral oil, 0.48 g, 12.0 mol) is added to a stirred solution of 2(S)-tert-butoxycarbonylamino-pentanedioic acid dimethyl ester (1.10 g, 4.0 mmol) in anhydrous DMF (20 mL) at room temperature under argon, and, after 0.5 hour, 1,3-dibromopropane (1.21 g, 6.0 mmol) is added to the mixture. The reaction mixture is stirred at 30–35° C. for 4 hours and then is allowed to stand at room temperature overnight. The mixture is poured into a mixture of ice-water (60 mL) and EtOAc (60 mL), then is acidified to pH 2 by slow addition of 6 N HCl. The layers are separated and the organic layer is washed successively with water and brine, dried over Na₂SO₄, and concentrated. The residue is purified by flash chromatography on silica gel using 20% EtOAc/Hexanes to give the desired product.

[1-Hydroxymethyl-2-(1-hydroxymethyl-cyclobutyl)-ethyl]-carbamic acid tert-butyl ester A solution of 1-(2-tert-butoxycarbonylamino-2-methoxycarbonyl-ethyl)-cyclobutanecarboxylic acid methyl ester (0.82 g, 2.6 mmol) in 1:1 EtOH/THF (18 mL) is treated with CaCl₂ (1.16 g, 10.5 mmol) and the resulting slurry is cooled under argon in an ice bath. To this mixture is added NaBH₄ (0.79 g, 20.9 mmol) portionwise. After 1 hour the ice bath is removed and the reaction mixture is allowed to stir at room temperature for 16 hours. The mixture is quenched with 10% Na₂CO₃ and water and the resulting thick, white slurry is extracted with EtOAc (3×). The combined organic layers are washed with brine, dried over Na₂SO₄, and concentrated to give the desired product.

Methanesulfonic acid 1-(2-tert-butoxycarbonylamino-3-methanesulfonyloxy-propyl)-cyclobutylmethyl ester A solution of [1-hydroxymethyl-2-(1-hydroxymethyl-cyclobutyl)-ethyl]-carbamic acid tert-butyl ester (0.64 g, 2.5 mmol) in CH₂Cl₂ (10 mL) is cooled under argon in an ice bath and triethylamine (1.4 mL, 10.0 mmol) is added via syringe. Methanesulfonyl chloride (0.6 mL, 7.8 mmol) is added dropwise and the mixture is stirred for 1 hour at 0° C. The reaction is diluted with CH$_2$Cl$_2$, washed with saturated NaHCO$_3$ and brine, dried over Na$_2$SO$_4$, and concentrated to give the desired product.

(6-Benzyl-6-aza-spiro[3.5]non-8-yl)-carbamic acid tert-butyl ester

A solution of methanesulfonic acid 1-(2-tert-butoxycarbonylamino-3-methanesulfonyloxy-propyl)-cyclobutylmethyl ester (0.94 g, 2.3 mmol) in benzylamine (8 mL, 73.2 mmol) is heated 70° C. for 24 hours. The mixture is then cooled to room temperature and poured into 1 N NaOH (20 ml). The resulting oily, aqueous mixture is extracted with hexanes (3×10 ml). The combined hexanes extracts are dried over MgSO$_4$, and the volatiles are removed in vacuo to give an oil which is purified by flash chromatography using a 1–10% gradient of EtOAc/hexanes.

(6-Aza-spiro[3.5]non-8-yl)-carbamic acid tert-butyl ester (Precursor P)

To a solution of (6-benzyl-6-aza-spiro[3.5]non-8-yl)-carbamic acid tert-butyl ester (0.13 g) in EtOH (5 mL) is added 10% Pd/C (0.05 g). The mixture is treated with hydrogen (30 psi) on a Parr apparatus for 8 hours. The reaction mixture is filtered through Celite, the filtrate concentrated, and the residue purified by flash chromatography on silica gel using 10% MeOH/CHCl$_3$ containing 1% NH$_4$OH to give the desired product.

Precursor Example Q

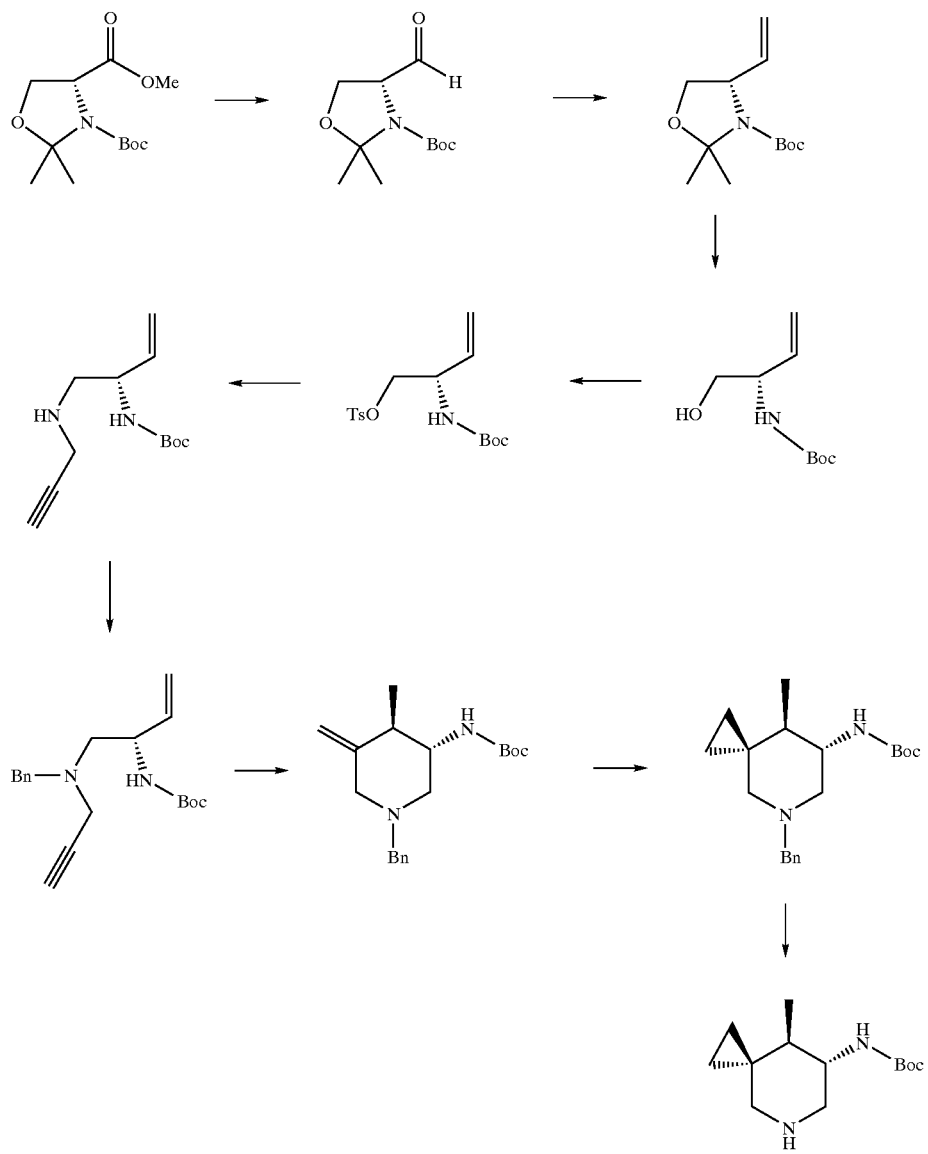

(Precursor Q)

3(R)-(tert-butoxycarbonyl)2,2-dimethyl-4-oxazolidine carboxaldehyde

A solution of methyl 3-(tert-butoxycarbonyl)2,2-dimethyl-4-oxazolidinecarboxylate (15.00 g, 57.8 mmol) is dissolved in toluene (100 mL) and cooled to −78° C. To it a solution of diisobutylaluminum hydride (1.0 M, 98.3 mL, 98.3 mmol) is added dropwise to maintain the internal temperature under −60° C. After the addition, the resulting solution is stirred at −78° C. for 30 min, and then slowly warmed to 0° C. in 2 hrs. The mixture is quenched by addition of water. The organic layer is separated and the aqueous layer is extracted once with ethyl acetate. The combined extracts are dried over anhydrous $MgSO_4$ and evaporated. The residue is purified by flash chromatography using ethyl acetate-hexanes.

3(S)-(tert-Butoxycarbonyl)-2,2-dimethyl-4-vinyl-oxazolidine

To a suspension of $Ph_3PCH_3Br$ (24.60 g, 68.8 mmol) in anhydrous THF (40 mL) is added t-BuOK (7.72 g, 68.8 mmol) in one portion at room temperature. After stirring for 10 min, the yellow mixture is treated with a solution of 3(R)-(tert-butoxycarbonyl)2,2-dimethyl-4-oxazolidine carboxaldehyde (10.50 g, 45.8 mmol) in THF. The mixture is stirred for additional 10 min and then partitioned between brine and EtOAc. The organic layer is separated and the aqueous layer is extracted with EtOAc (2×). The combined extracts are dried over $MgSO_4$ and evaporated under reduced pressure. The residue is treated with ether and the white solid which forms is removed by filtration. The filtrate is evaporated and the residue is purified by flash chromatography on silica gel using EtOAc-hexanes.

2(S)-tert-Butoxycarbonylamino-3-buten-1-ol

A solution of 3(S)-(tert-butoxycarbonyl)-2,2-dimethyl-4vinyl-oxazolidine (10.50 g, 46.3 mmol) and p-TsOH, $H_2O$ (0.88 g, 4.6 mmol) in MeOH (100 mL) is heated at reflux for 2 days. After cooling, the solvent is evaporated and the residue is purified by flash chromatography on silica gel using EtOAc-hexanes.

2(S)-tert-Butoxycarbonylamino-3-butenyl-1-(4-toluenesulfonate)

A solution of 2(S)-tert-butoxycarbonylamino-3-buten-1-ol (6.88 g, 36.8 mmol), p-toluenesulfonyl chloride (8.42 g, 44.1 mmol) and $Et_3N$ (6.2 mL, 44.5 mmol) in $CH_2Cl_2$ (120 mL) is heated at reflux for 3 hours. After cooling, the solution is washed with saturated $NaHCO_3$, dried over anhydrous $MgSO_4$ and evaporated. The residue is purified by flash chromatography on silica gel using EtOAc-hexanes.

2(S)-tert-butoxycarbonylamino-N-(1-prop-2-ynyl)-but-3-enylamine

A solution of 2(S)-tert-butoxycarbonylamino-3-butenyl-1-toluenesolfonate (10.34 g, 30.3 mmol) and 2-propynylamine (10.4 mL, 151.6 mmol) is heated at 45° C. for 4 hrs. The excess reagent is distilled under vacuum. The residue is purified by flash chromatography on silica gel using $CH_2Cl_2$-MeOH.

2(S)-tert-butoxycarbonylamino-N-(1-prop-2ynyl)-N-benzyl-but-3-enylamine

Benzyl bromide (0.83 mL, 7.0 mmol) is added dropwise to a stirred solution of 2(S)-tert-butoxycarbonylamino-N-(1-prop-2-ynyl)-but-3-enylamine (3.12 g, 13.9 mmol) in anhydrous $Et_2O$ (8 mL) at room temperature. The mixture is heated at reflux for 1 hour and then cooled to 0° C. The white crystals are filtered off and extracted with anhydrous $Et_2O$ (50 mL). The filtrate is concentrated in vacuo to yield a cloudy oil. The crude product is purified by flash chromatography on silica gel using 0–5% ether in hexanes to give the desired product. The excess 2(S)-tert-butoxycarbonylamino-N-(1-prop-2-ynyl)-but-3-enylamine is recovered by basifying an aqueous solution of the filtered salt with NaOH (2 M) followed by $Et_2O$ extraction and concentration.

3(S)-tert-butoxycarbonylamino-4(R)-methyl-5-methylene-1-benzyl-piperidine

To a solution of $Cp_2ZrCl_2$ (2.03 g, 6.9 mmol) in THF (25 mL) at −78° C. under argon was slowly added n-butyllithium (5.5 mL, 2.5 M in hexanes, 13.8 mmol). After stirring for 1 hour at −78° C., 2(S)-tert-butoxycarbonylamino-N-(1-prop-2ynyl)-N-benzyl-but-3-enylamine (1.97 g, 6.3 mmol) in THF (5 mL) is added. The yellow solution is warmed to room temperature over 2 hours and stirred for another 2 hours. Methanol (1.6 mL) is added to the resultant dark-brown solution; the color immediately changes to yellow. The mixture is diluted with saturated $NaHCO_3$ solution (20 mL) and $Et_2O$ (40 mL), the layers separated, and the aqueous layer extracted with $Et_2O$ (3×100 mL). The combined organic extracts are dried ($K_2CO_3$) and concentrated in vacuo to yield a cloudy yellow oil. HPLC analysis indicates that two diastereomers are present in about an 80:20 ratio. The crude product is purified by flash chromatography on silica gel using 3% triethylamine in hexanes to give the major diastereomer as the desired product.

(5-Benzyl-8(R)-methyl-5-azaspiro[2.5]oct-7-yl)-carbamic acid tert-butyl ester Zinc dust (7.46 g), cuprous chloride (1.5 g), and $Et_2O$ (25 mL) are refluxed 1 hour. 3(S)-tert-butoxycarbonylamino-4(R)-methyl-5-methylene-1-benzyl-piperidine (1.39 g, 4.4 mmol) and diiodomethane (5 mL, 62 mmol) are added. The mixture is heated at reflux for 10 hours, more diiodomethane (5 mL, 62 mmol) is added, and the mixture is heated at reflux for 15 hours more. The reaction mixture is quenched with water and the ether layer is separated, washed with 10% HCl, water, and $NaHCO_3$, and dried over $K_2CO_3$. Removal of the spent dessicant and concentration gives an oil which is purified by flash chromatography on silica gel using 10% EtOAc in hexanes.

(8(R)-Methyl-5-aza-spiro[2.5]oct-7-yl)-carbamic acid tert-butyl ester (Precursor Q)

(5-Benzyl-8(R)-methyl-5-azaspiro[2.5]oct-7-yl)-carbamic acid tert-butyl ester (0.54 g, 1.6 mmol) is dissolved in 1,2-dichloroethane (2 mL) and the mixture is cooled at 0° C. A solution of α-chloroethyl chloroformate (0.25 g, 1.8 mmol) in 1,2-dichlorethane (1 mL) is then added dropwise over 15 min and the stirring is continued at 0° C. for 15 min. The mixture is heated at reflux for 1 hour, cooled to room temperature, and the solvents are removed under reduced pressure. The crude oily residue is dissolved in MeOH (1 mL) and the mixture is heated at reflux for 1 hour. The solvent is again evaporated under reduced pressure and the crude product is dissolved in water (3 mL) and the aqueous layer is extracted with $Et_2O$ (2×1 mL) and $CH_2CL_2$ (2×1 mL). Solid $NaHCO_3$ (0.33 g, 3.9 mmol) is added to the aqueous layer (pH=9.0) which is extracted with $CH_2CL_2$ (2×1 mL). The combined organic layers are dried with $Na_2SO_4$ and the volatiles evaporated to give the desired product as an oil.

Precursor Example R

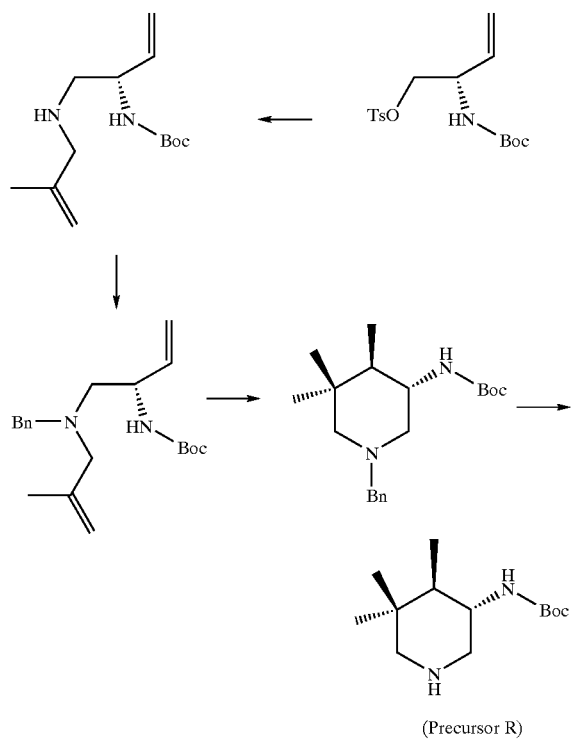

(Precursor R)

2(S)-tert-butoxycarbonylamino-N-(2-methyl-2-propenyl)-but-3-enylamine

A solution of 2(S)-tert-butoxycarbonylamino-3-butenyl-1-toluenesulfonate (5.17 g, 15.1 mmol) and methallylamine (5.4 mL, 75.8 mmol) is heated at 45° C. for 4 hrs. The excess reagent is distilled under vacuum. The residue is purified by flash chromatography on silica gel using $CH_2Cl_2$-MeOH.

2(S)-tert-butoxycarbonylamino-N-(1-methyl-2-propenyl)-N-benzyl-but-3-enylamine Benzyl bromide (0.42 mL, 3.5 mmol) is added dropwise to a stirred solution of 2(S)-tert-butoxycarbonylamino-N-(2-methyl-2-propenyl)-but-3-enylamine (1.68 g, 7.0 mmol) in anhydrous $Et_2O$ (4 mL) at room temperature. The mixture is heated at reflux for 1 hour and then cooled to 0° C. The white crystals are filtered off and extracted with anhydrous $Et_2O$ (25 mL). The filtrate is concentrated in vacuo to yield a cloudy oil. The crude product is purified by flash chromatography on silica gel using 0–5% ether in hexanes to give the desired product. The excess 2(S)-tert-butoxycarbonylamino-N-(1-methyl-2-propenyl)-but-3-enylamine is recovered by basifying an aqueous solution of the filtered salt with NaOH (2 M) followed by $Et_2O$ extraction and concentration.

3(S)-tert-butoxycarbonylamino-4(R)-methyl-5,5-dimethyl-1-benzyl-piperidine

To a solution of $Cp_2ZrCl_2$ (1.01 g, 3.5 mmol) in THF (15 mL) at −78° C. under argon was slowly added n-butyllithium (2.8 mL, 2.5 M in hexanes, 7.0 mmol). After stirring for 1 hour at −78° C., 2(S)-tert-butoxycarbonylamino-N-(1-methyl-2-propenyl)-N-benzyl-but-3-enylamine (1.06 g, 3.2 mmol) in THF (5 mL) is added. The yellow solution is warmed to room temperature over 2 hours and stirred for another 2 hours. Methanol (0.8 mL) is added to the resultant dark-brown solution; the color immediately changes to yellow. The mixture is diluted with saturated $NaHCO_3$ solution (10 mL) and $Et_2O$ (20 mL), the layers separated, and the aqueous layer extracted with $Et_2O$ (3×50 mL). The combined organic extracts are dried ($K_2CO_3$) and concentrated in vacuo to yield a cloudy yellow oil. The crude product is purified by flash chromatography on silica gel using 3% triethylamine in hexanes to give the major diastereomer as the desired product.

3(S)-tert-butoxycarbonylamino-4(R)-methyl-5,5-dimethyl-piperidine (Precursor R)

3(S)-tert-butoxycarbonylamino-4(R)-methyl-5,5-dimethyl-1-benzyl-piperidine (0.69 g, 2.1 mmol) is combined with 10% Pd/C (0.07 g) in methanol (25 mL) and is shaken under a hydrogen atmosphere (40 psi) at room temperature for 15 h. The spent catalyst is removed by filtration through Celite and the solvent is removed in vacuo to give the desired product.

Precursor Example S

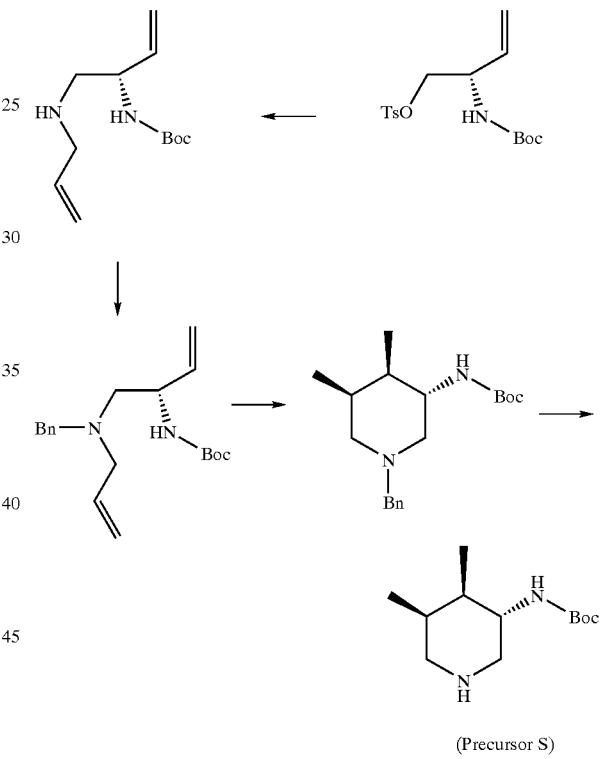

(Precursor S)

2(S)-tert-butoxycarbonylamino-N-(2-propenyl)-but-3-enylamine

A solution of 2(S)-tert-butoxycarbonylamino-3-butenyl-1-toluenesulfonate (3.47 g, 10 mmol) and allylamine (3.8 mL, 50.3 mmol) is heated at 45° C. for 4 hrs. The excess reagent is distilled under vacuum. The residue is purified by flash chromatography on silica gel using $CH_2Cl_2$-MeOH.

2(S)-tert-butoxycarbonylamino-N-(1-methyl-2-propenyl)-N-benzyl-but-3-enylamine Benzyl bromide (0.28 mL, 2.3 mmol) is added dropwise to a stirred solution of 2(S)-tert-butoxycarbonylamino-N-(2-propenyl)-but-3-enylamine (1.06 g, 4.7 mmol) in anhydrous $Et_2O$ (3 mL) at room temperature. The mixture is heated at reflux for 1 hour and then cooled to 0° C. The white crystals are filtered off and extracted with anhydrous $Et_2O$ (18 mL).

The filtrate is concentrated in vacuo to yield a cloudy oil. The crude product is purified by flash chromatography on silica gel using 0–5% ether in hexanes to give the desired product. The excess 2(S)-tert-butoxycarbonylamino-N-(1-methyl-2-propenyl)-but-3-enylamine is recovered by basifying an aqueous solution of the filtered salt with NaOH (2 M) followed by Et$_2$O extraction and concentration.

3(S)-tert-butoxycarbonylamino-4(R)-methyl-5(S)-methyl-1-benzyl-piperidine

To a solution of Cp$_2$ZrCl$_2$ (0.67 g, 2.3 mmol) in THF (10 mL) at −78° C. under argon was slowly added butyllithium (1.85 mL, 2.5 M in hexanes, 4.6 mmol). After stirring for 1 hour at −78° C., 2(S)-tert-butoxycarbonylamino-N-(2-propenyl)-N-benzyl-but-3-enylamine (0.71 g, 2.1 mmol) in THF (3 mL) is added. The yellow solution is warmed to room temperature over 2 hours and stirred for another 2 hours. Methanol (0.5 mL) is added to the resultant dark-brown solution; the color immediately changes to yellow. The mixture is diluted with saturated NaHCO$_3$ solution (7 mL) and Et$_2$O (15 mL), the layers separated, and the aqueous layer extracted with Et$_2$O (3×35 mL). The combined organic extracts are dried (K$_2$CO$_3$) and concentrated in vacuo to yield a cloudy yellow oil. The crude product is purified by flash chromatography on silica gel using 3% triethylamine in hexanes to give the major diastereomer as the desired product.

3(S)-tert-butoxycarbonylamino-4(R)-methyl-5(S)-methyl-piperidine (Precursor S)

3(S)-tert-butoxycarbonylamino-4(R)-methyl-5(S)-methyl-1-benzyl-piperidine (0.32 g, 1.0 mmol) is combined with 10% Pd/C (0.04 g) in methanol (20 mL) and is shaken under a hydrogen atmosphere (40 psi) at room temperature for 15 h. The spent catalyst is removed by filtration through Celite and the solvent is removed in vacuo to give the desired product.

b. Final Product Preparation

Example 1

7-[3S-amino-5S-methyl-piperidinyl]-1-cyclopropyl-1,4-dihydro-6-fluoro-8-methoxy-4-oxo-3-quinolinecarboxylic acid hydrochloride

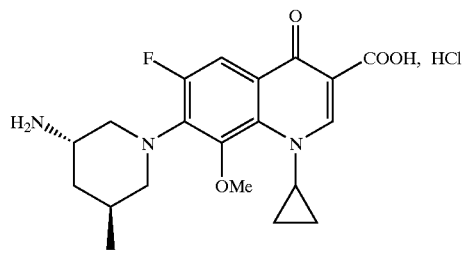

1-cyclopropyl-1,4-dihydro-6,7-difluoro-8-methoxy-4-oxo-quinoline-3-carboxylic acid (Precursor A) (0.059 g, 0.200 mmol), (5(S)-methyl-piperidin-3(S)-yl)-carbamic acid tert-butyl ester (Precursor M) (0.048 g, 0.210 mmol) and triethylamine (0.075 mL) are dissolved in N-methylpyrrolidone (2 mL). The reaction mixture is stirred at 80° C. for 5 hours, then is poured on an ice/water mixture. The pH is lowered to 2 with diluted HCl and the resulting precipitate is filtered. The solid is then suspended in ethanol and 6N HCl is added. After 18 hours at room temperature, the desired final product is collected by filtration.

Example 2

7-[3S-amino-5S-ethyl-piperidinyl]-1-cyclopropyl-1,4-dihydro-6-fluoro-8-methoxy-4-oxo-3-quinolinecarboxylic acid hydrochloride

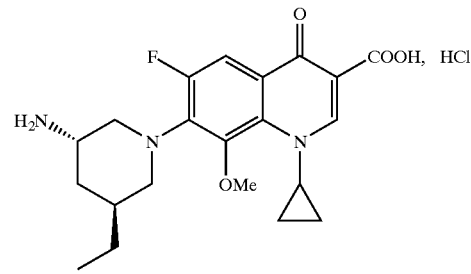

A procedure similar to Example 1 above is used, using 1-cyclopropyl-1,4-dihydro-6,7-difluoro-8-methoxy-4-oxo-quinoline-3-carboxylic acid (Precursor A) and (5(S)-ethyl-piperidin-3(S)-yl)-carbamic acid tert-butyl ester (Precursor N) as the starting materials. The procedure utilizes the same reaction conditions and molar ratio of reactants as Example 1.

Example 3

7-[3S-amino-5,5dimethyl-piperidinyl]-1-cyclopropyl-1,4-dihydro-6-fluoro-8-methyl-4-oxo-3-quinolinecarboxylic acid hydrochloride

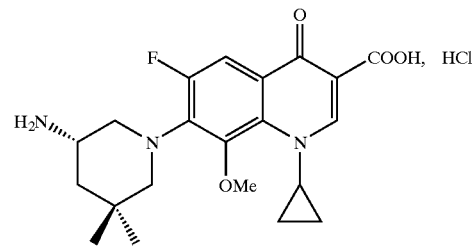

A procedure similar to Example 1 above is used, but using 1-cyclopropyl-1,4-dihydro-6,7-difluoro-8-methoxy-4-oxo-quinoline-3-carboxylic acid (Precursor A) and (5,5-dimethyl-piperidin-3(S)-yl)-carbamic acid tert-butyl ester (Precursor O) as the starting materials. The procedure utilizes the same reaction conditions and molar ratio of reactants as Example 1.

Example 4

7-[3S-amino-4S-ethyl-5R-methyl-piperidinyl]-1-cyclopropyl-1,4-dihydro-6-fluoro-8-methoxy-4-oxo-3-quinolinecarboxylic acid hydrochloride

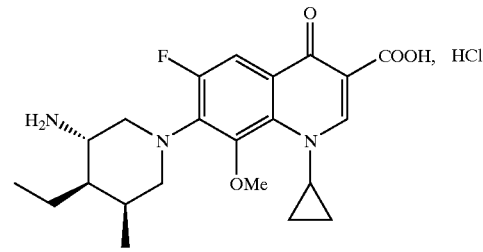

A procedure similar to Example 1 above is used, but using 1-cyclopropyl-1,4-dihydro-6,7-difluoro-8-methoxy-4-oxoquinoline-3-carboxylic acid (Precursor A) and 3(S)-tert-butoxycarbonylamino-4(R)-ethyl-5(S)-methyl-piperidine (Precursor L) as the starting materials. The procedure utilizes the same reaction conditions and molar ratio of reactants as Example 1.

Example 5

7-[7-amino-8R-methyl-5-azaspiro[2.5]-octanyl]-1-cyclopropyl-1,4-dihydro-6-fluoro-8-methoxy-4-oxo-3-quinolinecarboxylic acid hydrochloride

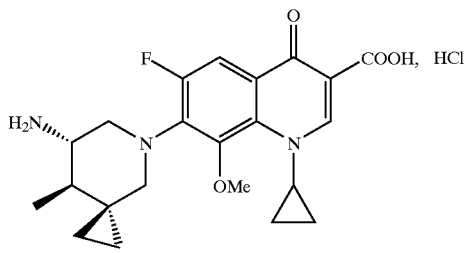

A procedure similar to Example 1 above is used, but using 1-cyclopropyl-1,4-dihydro-6,7-difluoro-8-methoxy-4-oxo-quinoline-3-carboxylic acid (Precursor A) and (8(R)-methyl-5-aza-spiro[2.5]oct-7-yl)-carbamic acid tert-butyl ester (Precursor Q) as the starting materials. The procedure utilizes the same reaction conditions and molar ratio of reactants as Example 1.

Example 6

7-[8-amino-6-azaspiro[3.5]-nonanyl]-1-cyclopropyl-1,4-dihydro-6-fluoro-8-methyl-4-oxo-3-quinolinecarboxylic acid hydrochloride

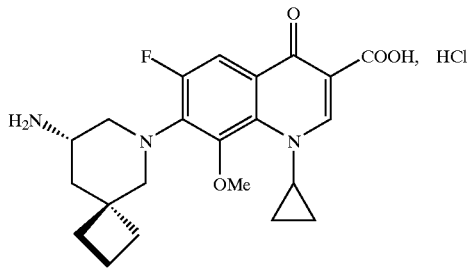

A procedure similar to Example 1 above is used, but using 1-cyclopropyl-1,4-dihydro-6,7-difluoro-8-methoxy-4-oxo-quinoline-3-carboxylic acid (Precursor A) and (6-aza-spiro[3.5]non-8-yl)-carbamic acid tert-butyl ester (Precursor P) as the starting materials. The procedure utilizes the same reaction conditions and molar ratio of reactants as Example 1.

Example 7

7-[3S-amino-5S-methyl-piperidinyl]-6-bromo-8-chloro-1-cyclopropyl-1,4-dihydro-4-oxo-3-quinolinecarboxylic acid dihydrochloride

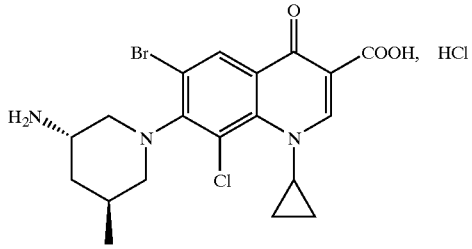

A procedure similar to Example 1 above is used, but using 6-bromo-8-chloro-1-cyclopropyl-1,4-dihydro-7-fluoro-4-oxoquinoline-3-carboxylic acid (Precursor B) and (5(S)-methyl-piperidin-3(S)-yl)-carbamic acid tert-butyl ester (Precursor M) as the starting materials. The procedure utilizes the same reaction conditions and molar ratio of reactants as Example 1.

Example 8

7-[3S-amino-4R-ethyl-5S-methyl-piperidinyl]-6-bromo-8-chloro-1-cyclopropyl-1,4-dihydro-4-oxo-3-quinolinecarboxylic acid hydrochloride

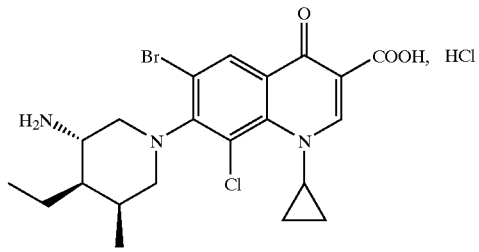

A procedure similar to Example 1 above is used, but using 6-bromo-8-chloro-1-cyclopropyl-1,4-dihydro-7-fluoro-4-oxoquinoline-3-carboxylic acid (Precursor B) and 3(S)-tert-butoxycarbonylamino-4(R)-ethyl-5(S)-methyl-piperidine (Precursor L) as the starting materials. The procedure utilizes the same reaction conditions and molar ratio of reactants as Example 1.

Example 9

Preparation of 7-[3S-amino-5,5dimethyl-4R-methyl-piperidinyl]-8-chloro-1-cyclopropyl-1,4-dihydro-6-methyl-4-oxo-3-quinolinecarboxylic acid dihydrochloride

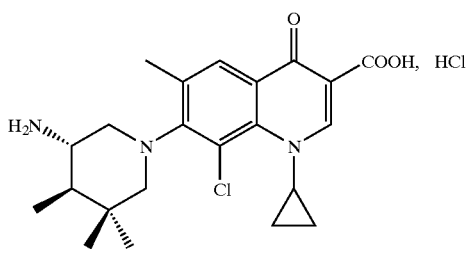

8-Chloro-1-cyclopropyl-1,4-dihydro-7-fluoro-6-methyl-4-oxo-quinoline-3-carboxylic acid boron difluoride complex
8-chloro-1-cyclopropyl-1,4-dihydro-7-fluoro-6-methyl-4-oxoquinoline-3-carboxylic acid (Precursor C) (1 g, 3.4 mmol) is dissolved in THF (10 mL) and boron trifluoride etherate (1.76 mL, 13.9 mmol) is added. The mixture is stirred at 60° C. for 2 hours then cooled to room temperature. The desired product is collected by filtration, washed, and air dried.

7-[3S-tert-butoxycarbonylamino-5,5dimethyl-4R-methyl-piperidinyl]-8-chloro-1-cyclopropyl-1,4-dihydro-6-methyl-4-oxo-3-quinolinecarboxylic acid 8-Chloro-1-cyclopropyl-1,4-dihydro-7-fluoro-6-methyl-4-oxo-quinoline-3-carboxylic acid boron difluoride complex (0.10 g, 0.291 mmol) is dissolved in 2 mL of acetonitrile; then diisopropylethylamine (0.16 mL, 0.923 mmol) and 3(S)-tert-butoxycarbonylamino-4(R)-methyl-5,5-dimethyl-piperidine (Precursor R) (0.086 g, 0.353 g) are added. The mixture is stirred at 60° C. for 24 hours, and then the solvent is removed by evaporation. The residue is dissolved in 5 mL of ethanol and 2 mL of triethylamine. The solution is stirred at 80° C. for 4 hours, then evaporated to dryness. The desired compound is isolated by flash chromatography on silica gel using EtOAc/hexanes.

7-[3S-amino-5,5dimethyl-4R-methyl-piperidinyl]-8-chloro-1-cyclopropyl-1,4-dihydro-6-methyl-4-oxo-3-quinolinecarboxylic acid hydrochloride 7-[3S-tert-butoxycarbonylamino-5,5dimethyl-4R-methyl-piperidinyl]-8-chloro-1-cyclopropyl-1,4-dihydro-6-methyl-4-oxo-quinoline-3-carboxylic acid (0.54 g, 0.104 mmol) is dissolved in ethanol (2 mL) and concentrated hydrochloric acid (0.5 mL). After half an hour at room temperature the desired compound is collected by filtration after cooling the mixture in an ice bath.

Example 10

Preparation of: 7-[3S-amino-4R-methyl-5S-methyl-piperidinyl]-8-chloro-1-cyclopropyl-6-hydroxy-1,4-dihydro-4-oxo-3-quinolinecarboxylic acid dihydrogen sulfate

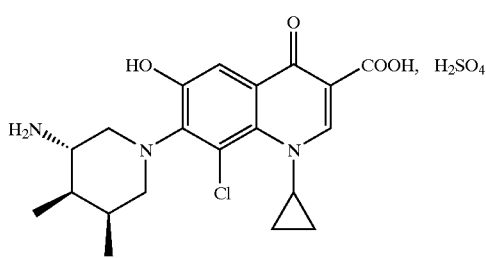

Ethyl 7-[3S-t-butoxycarbonylamino-4R-methyl-5S-methyl-piperidinyl]-8-chloro-1-cyclopropyl-1,4-dihydro-6-nitro-4-oxo-3-quinolinecarboxylate Ethyl 8-chloro-1-cyclopropyl-1,4-dihydro-7-fluoro-6-nitro-4-oxo-quinoline-3-carboxylate (Precursor D) (0.064 g, 0.180 mmol) and 3(S)-tert-butoxycarbonylamino-4(R)-methyl-5(S)-methyl-piperidine (Precursor S) (0.08 g, 0.351 mmol) are dissolved in DMSO (1 mL) and stirred at room temperature for 15 minutes. Water (5 mL) is then added and the desired product collected by filtration.

Ethyl 7-[3S-t-butoxycarbonylamino-4R-methyl-5S-methyl-piperidinyl]-6-amino-8-chloro-1-cyclopropyl-1,4-dihydro-4-oxo-3-quinolinecarboxylate Ethyl 7-[3S-t-butoxycarbonylamino-4R-methyl-5S-methyl-piperidinyl]-8-chloro-1-cyclopropyl-1,4-dihydro-6-nitro-4-oxo-3-quinolinecarboxylate (0.072 g, 0.128 mmol) is dissolved in ethanol (1 mL) and Raney Nickel (0.035 g) is added. The reaction mixture is stirred under hydrogen (1 atm) at room temperature for 18 hours. The catalyst is removed by filtration on Celite and the filtrate evaporated to give the desired product.

Ethyl 7-[3S-t-butoxycarbonylamino-4R-methyl-5S-methyl-piperidinyl]-8-chloro-1-cyclopropyl-6-hydroxy-1,4-dihydro-4-oxo-3-quinolinecarboxylate Ethyl 7-[3S-t-butoxycarbonylamino-4R-methyl-5S-methyl-piperidinyl]-6-amino-8-chloro-1-cyclopropyl-1,4-dihydro-4-oxo-3-quinolinecarboxylate (0.068 g, 0.127 mmol) is dissolved in 2N HCl (2 mL) at 0° C. A solution of sodium nitrite (0.01 g, 0.145 mmol) in water (0.2 mL) is then added and the solution stirred at 0° C. for 1 hour. A solution of NaBF$_4$ (0.02 g, 0.182 mmol) in water (0.2 mL) is added and the resulting precipitate filtered. The solid is re-suspended in trifluoroacetic acid (0.2 mL) and K$_2$CO$_3$ (0.5 g) is added portionwise at 40° C. Water (10 mL) is added and the reaction mixture allowed to stir at room temperature for 2 hours. The aqueous phase is extracted with dichloromethane and the desired product purified by chromatography on silica gel using 5% methanol in CH$_2$Cl$_2$ as eluent.

7-[3S-amino-4R-methyl-5S-methyl-piperidinyl]-8-chloro-1-cyclopropyl-6-hydroxy-1,4-dihydro-4-oxo-3-quinolinecarboxylic acid dihydrogen sulfate Ethyl 7-[3S-t-butoxycarbonylamino-4R-methyl-5S-methyl-piperidinyl]-8-chloro-1-cyclopropyl-6-hydroxy-1,4-dihydro-4-oxo-3-quinolinecarboxylate (0.042 g, 0.079 mmol) is suspended in a mixture of acetic acid/sulfuric acid/water (6:4:1, 1 mL) and the reaction mixture is heated at reflux for 4 hours. After cooling the desired product is isolated by filtration.

Example 11

7-[3S-Amino-5S-methyl-piperidinyl]-1-cyclopropyl-1,4-dihydro-6-fluoro-4-oxo-1,8-naphthyridine-3-carboxylic acid hydrochloride

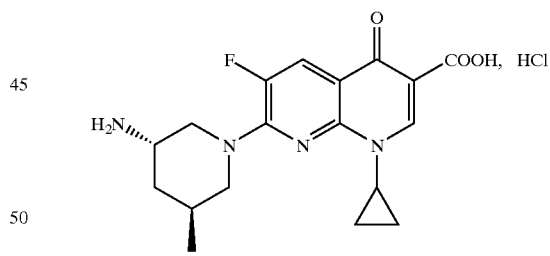

Ethyl-7-chloro-1-cyclopropyl-6-fluoro-4-oxo-1,4-dihydro-naphthyridine-3-carboxylate (Precursor E) (0.062 g, 0.200 mmol), (5(S)-methyl-piperidin-3(S)-yl)-carbamic acid tert-butyl ester (Precursor M) (0.048 g, 0.214 mmol) and triethylamine (0.05 mL, 0.359 mmol) are dissolved in acetonitrile (1 mL) and stirred at room temperature for 18 hr. The solvent is evaporated under vacuum and the residue crystallized in water. The resulting solid is collected by filtration and suspended in a 1/1 mixture of 2N NaOH and ethanol (1 mL) and stirred at room temperature for 24 hours. The pH is then adjusted to 7.4 using 1N HCl and the precipitate is collected by filtration. The solid is resuspended in ethanol and treated with 6N hydrochloric acid for 18 hr at room temperature. The desired final product is collected by filtration.

Example 12

7-[3S-amino-4S-ethyl-5R-methyl-piperidinyl]-1-Cyclopropyl-1,4-dihydro-6-fluoro-4-oxo-1,8-naphthyridine-3-carboxylic acid hydrochloride

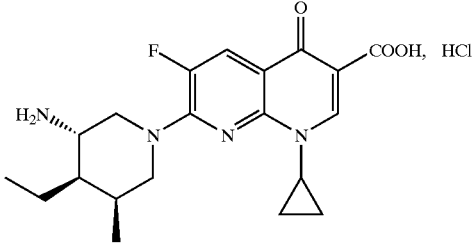

A procedure similar to Example 11 above is used using ethyl-7-chloro-1-cyclopropyl-6-fluoro-4-oxo-1,4-dihydro-naphthyridine-3-carboxylate (Precursor E) and 3(S)-tert-butoxycarbonylamino-4(R)-ethyl-5(S)-methyl-piperidine (Precursor L) as the starting materials. The procedure utilizes the same reaction conditions and molar ratio of reactants as Example 11.

Example 13

7-[3S-amino-5S-methyl-piperidinyl]-9-fluoro-2,3-dihydro-3S-methyl-7-oxo-7H-pyrido[1,2,3-de]-1,4-benzoxazine-6-carboxylic acid hydrochloride

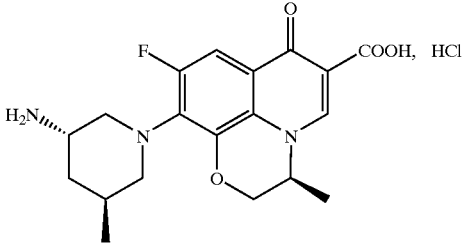

9,10-difluoro-2,3-dihydro-3S-methyl-7-oxo-7H-pyrido[1,2,3-de]-1,4-benzoxazine-6-carboxyl acid (Precursor F) (0.056 g, 0.199 mmol), (5(S)-methyl-piperidin-3(S)-yl)-carbamic acid tert-butyl ester (Precursor M) (0.045 g, 0.201 mmol) and triethylamine (0.075 mL, 0.538 mmol) are dissolved in N-methyl-pyrrolidone (1 mL). The solution is stirred at 80° C. for 18 hours and is poured into an ice/water mixture. The pH is lowered to 2 using dilute HCl and the resulting precipitate is collected by filtration. The solid is suspended in ethanol and 6$\underline{N}$ HCl is added. After 18 hr at room temperature, the desired product is collected by filtration and air dried.

Example 14

7-[3S-amino-5,5-dimethyl-piperidinyl]-9-fluoro-2,3-dihydro-3S-methyl-7-oxo-7H-pyrido[1,2,3-de]-1,4-benzoxazine-6-carboxylic acid hydrochloride

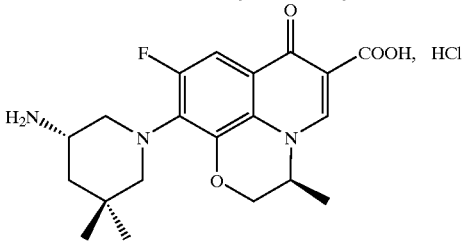

A procedure similar to Example 13 above is used using 9,10-difluoro-2,3-dihydro-3S-methyl-7-oxo-7H-pyrido[1,2, 3-de]-1,4-benzoxazine-6-carboxylic acid (Precursor F) and (5,5-dimethyl-piperidin-3(S)-yl)-carbamic acid tert-butyl ester (Precursor O) as the starting materials. The procedure utilizes the same reaction conditions and molar ratio of reactants as Example 13.

Example 15

7-[7-amino-8R-methyl-5-azaspiro[2.5]-octanyl]-5,6,8-trifluoro-9-cyclopropyl-1,3,4,9-tetrahydroisothiazolo[5,4-b]quinoline-3,4-dione hydrochloride

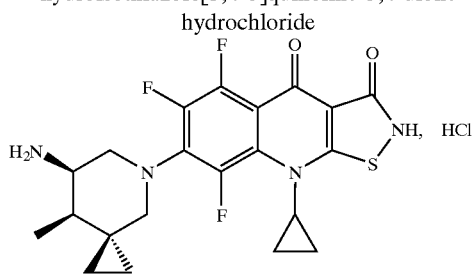

5,6,7,8-tetrafluoro-9-cyclopropyl-1,3,4,9-tetrahydroisothiazolo[5,4-b]quinoline-3,4-dione (Precursor G) (0.067 g, 0.203 mmol) is suspended in DMF (1 mL) and (8(R)-methyl-5-aza-spiro[2.5]oct-7-yl)-carbamic acid tert-butyl ester (Precursor Q) (0.051 g, 0.212 mmol) and triethylamine (0.05, 0.359 mmol mL) is added. The reaction mixture is stirred at 50° C. for 6 hr. The mixture is concentrated under vacuum, and the residue is triturated with water. The precipitate is collected, rinsed with ethanol, and suspended in ethanol. Drops of 12$\underline{N}$ HCl are added and the suspension is stirred for 12 hr at 20° C. The desired product is collected by filtration and air dried.

Example 16

7-[3S-amino-5S-ethyl-piperidinyl]-5,6,8-trifluoro-9-cyclopropyl-1,3,4,9-tetrahydroiso-thiazolo[5,4-b]quinoline-3,4-dione hydrochloride

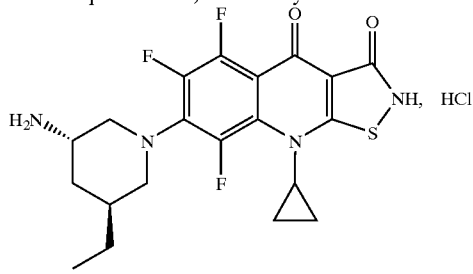

A procedure similar to Example 15 above is used using 5,6,7,8-tetrafluoro-9-cyclopropyl-1,3,4,9-tetrahydroisothiazolo[5,4-b]quinoline-3,4-dione (Precursor G) and (5(S)-ethyl-piperidin-3(S)-yl)-carbamic acid tert-butyl ester (Precursor N) as the starting materials. The procedure utilizes the same reaction conditions and molar ratio of reactants as Example 15.

Example 17

Preparation of: 8-[3S-amino-5S-methyl-piperidinyl]-1-cyclopropyl-7-fluoro-9-methyl-4-oxo-4H-quinolizine-3-carboxylic acid hydrochloride

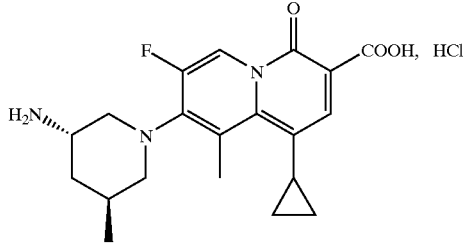

Ethyl 8-[3S-t-butoxycarbonylamino-5S-methyl-piperidinyl]-1-cyclopropyl-7-fluoro-9-methyl-4-oxo-4H-quinolizine-3-carboxylate A solution of ethyl 8-chloro-1-cyclopropyl-7-fluoro-9-methyl-4-oxo-4H-quinolizine-3-carboxylate (precursor H) (0.040 g, 0.124 mmol), (5(S)-methyl-piperidin-3(S)-yl)-carbamic acid tert-butyl ester (Precursor M) (0.033 g, 0.149 mmol) and $Et_3N$ (0.034 mL, 0.244 mmol) in DMF (2 mL) is stirred at room temperature for 3 days. The solvent is evaporated under reduced pressure. The residue is dissolved in $CH_2Cl_2$ and the solution is washed with 0.1 M HCl, dried over anhydrous $MgSO_4$, and concentrated to give the desired product.

8-[3S-t-butoxycarbonylamino-5S-methyl-piperidinyl]-1-cyclopropyl-7-fluoro-9-methyl-4-oxo-4H-quinolizine-3-carboxylic acid trifluoroacetate A solution of ethyl 8-[3S-t-butoxycarbonylamino-5S-methyl-piperidinyl]-1-cyclopropyl-7-fluoro-9-methyl-4-oxo-4H-quinolizine-3-carboxylate (0.060 g, 0.120 mmol) and 16% NaOH (0.15 mL) in EtOH (2 mL) is stirred at room temperature for 6 hr. The mixture is partitioned between $CH_2Cl_2$ and 0.1 N HCl solution. The organic layer is separated and the aqueous layer is extracted with $CH_2Cl_2$ (2×). The combined extracts are dried over anhydrous $MgSO_4$ and evaporated to give a yellow solid which is purified by preparative reverse phase HPLC using a $CH_3CN/H_2O$-0.1% TFA gradient as the eluent. Concentration of the product-containing fractions gives the desired product.

8-[3S-amino-5S-methyl-piperidinyl]-1-cyclopropyl-7-fluoro-9-methyl-4-oxo-4H-quinolizine-3-carboxylic acid hydrochloride 8-[3S-t-butoxycarbonylamino-5S-methyl-piperidine-1-yl]-1-cyclopropyl-7-fluoro-9-methyl-4-oxo-4H-quinolizine-3-carboxylic acid trifluoroacetate (0.032 g, 0.055 mmol) is treated with concentrated HCl (0.5 mL) for 10 min. at room temperature. The volatiles are evaporated under reduced pressure to give the desired product.

Example 18

8-[3S-amino-5S-ethyl-piperidinyl]-1-cyclopropyl-7-fluoro-9-methyl-4-oxo-4H-quinolizine-3-carboxylic acid dihydrochloride

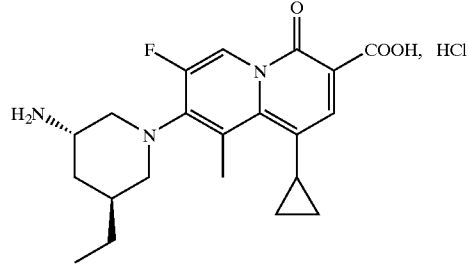

A procedure similar to Example 17 above is used, using ethyl 8-chloro-1-cyclopropyl-7-fluoro-9-methyl-4-oxo-4H-quinolizine-3-carboxylate (Precursor H) and (5(S)-ethyl-piperidin-3(S)-yl)-carbamic acid tert-butyl ester (Precursor N) as the starting materials. The procedure utilizes the same reaction conditions and molar ratio of reactants as Example 17.

Example 19

Preparation of: 8-[3S-Amino-5S-ethyl-piperidinyl]-1-cyclopropyl-7-hydroxy-9-methyl-4-oxo-4H-quinolizine-3-carboxylic acid dihydrochloride

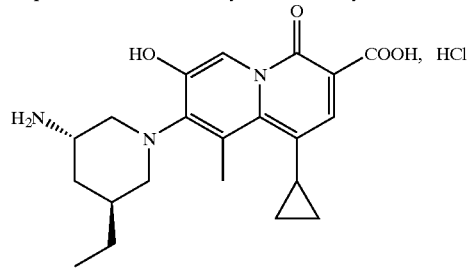

Ethyl 8-[3S-t-butoxycarbonylamino-5S-ethyl-piperidinyl]-1-cyclopropyl-9-methyl-7-nitro-4-oxo-4H-quinolizine-3-carboxylate A solution of ethyl 8-chloro-1-cyclopropyl-9-methyl-7-nitro-4-oxo-4H-quinolizine-3-carboxylate (Precursor I) (0.053 g, 0.151 mmol), (5(S)-ethyl-piperidin-3(S)-yl)-carbamic acid tert-butyl ester (Precursor N) (0.035 g, 0.153 mmol) and $Et_3N$ (0.041 mL, 0.294 mmol) in DMF (2 mL) is stirred at room temperature for 3 days. The solvent is evaporated under reduced pressure. The residue is dissolved in $CH_2Cl_2$ and the solution is washed with 0.1 M HCl, dried over anhydrous $MgSO_4$, and concentrated to give the desired product.

Ethyl 8-[3S-t-butoxycarbonylamino-S8-ethyl-piperidinyl]-7-amino-1-cyclopropyl-9-methyl-4-oxo-4H-quinolizine-3-carboxylate Ethyl 8-[3S-t-butoxycarbonylamino-5S-ethyl-piperidinyl]-1-cyclopropyl-9-methyl-7-nitro-4-oxo-4H-quinolizine-3-carboxylate (0.065 g, 0.120 mmol) is dissolved in ethanol (1 mL) and Raney Nickel (0.035 g) is added. The reaction mixture is stirred under hydrogen (1 atm) at room temperature for 18 hours. The catalyst is removed by filtration on Celite and the filtrate evaporated to give the desired product.

Ethyl 8-[3S-t-butoxycarbonylamino-5S-ethyl-piperidinyl]-1-cyclopropyl-7-hydroxy-9-methyl-4-oxo-4H-quinolizine-3-carboxylate Ethyl 8-[3S-t-butoxycarbonylamino-5S-ethyl-piperidinyl]-7-amino-1-cyclopropyl-9-methyl-4-oxo-4H-quinolizine-3- carboxylate (0.062 g, 0.120 mmol) is dissolved in 2N HCl (2 mL) at 0° C. A solution of sodium nitrite (0.009 g, 0.130 mmol) in water (0.2 mL) is then added and the solution stirred at 0° C. for 1 hour. A solution of NaBF$_4$ (0.02 g, 0.182 mmol) in water (0.2 mL) is added and the resulting precipitate filtered. The solid is re-suspended in trifluoroacetic acid (0.2 mL) and K$_2$CO$_3$ (0.5 g) is added portionwise at 40° C. Water (10 mL) is added and the reaction mixture allowed to stir at room temperature for 2 hours. The aqueous phase is extracted with CH$_2$Cl$_2$ and the desired product purified by flash chromatography on silica gel using 5% methanol in CH$_2$Cl$_2$ as eluent.

8-[3S-t-butoxycarbonylamino-5S-ethyl-piperidinyl]-1-cyclopropyl-7-hydroxy-9-methyl-4-oxo-4H-quinolizine-3-carboxylic acid A solution of ethyl 8-[3S-t-butoxycarbonylamino-5S-methyl-piperidinyl]-1-cyclopropyl-7-hydroxy-9-methyl-4-oxo-4H-quinolizine-3-carboxylate (0.036 g, 0.070 mmol) and 16% NaOH (0.15 mL) in EtOH (2 mL) is stirred at room temperature for 6 hr. The mixture is partitioned between CH$_2$Cl$_2$ and 0.1 N HCl solution. The organic layer is separated and the aqueous layer is extracted with CH$_2$Cl$_2$ (2x). The combined extracts are dried over anhydrous MgSO$_4$ and evaporated to give the desired product.

8-[3S-amino-5S-ethyl-piperidinyl]-1-cyclopropyl-7-hydroxy-9-methyl-4-oxo-4H-quinolizine-3-carboxylic acid dihydrochloride 8-[3S-t-butoxycarbonylamino-5S-methyl-piperidine-1-yl]-1-cyclopropyl-7-hydroxy-9-methyl-4-oxo-4H-quinolizine-3-carboxylic acid (0.031 g, 0.063 mmol) is treated with concentrated HCl (0.5 mL) for 10 min. at room temperature. The volatiles are evaporated under reduced pressure to give the desired product.

Example 20

Preparation of: 7-[3S-amino-5S-methyl-piperidinyl]-3-amino-8-chloro-1-cyclopropyl-6-fluoro-1H-quinazoline-2,4-dione hydrochloride

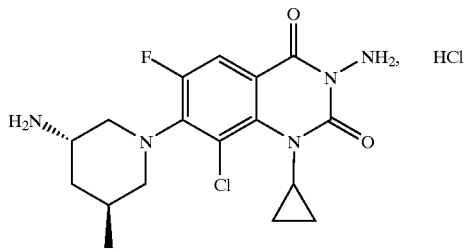

{7-[3S-t-butoxycarbonylamino-5S-methyl-piperidin-1-yl)-8-chloro-1-cyclopropyl-6-fluoro-2,4-dioxo-1,4-dihydro-2H-quinazolin-3-yl}carbamic acid tert-butyl ester A solution of 8-chloro-1-cyclopropyl-6,7-difluoro-2,4-dioxo-1,4-dihydro-2H-quinazolin-3-yl)carbamic acid tert-butyl ester (Precursor J) (0.06 g, 0.155 mmol), (5(S)-methyl-piperidin-3(S)-yl)-carbamic acid tert-butyl ester (Precursor M) (0.66 g, 0.310 mmol), and triethylamine (0.065 mL, 0.465) are stirred and heated in acetonitrile (3 mL) at reflux for 48 hours. After cooling to room temperature, the reaction mixture is diluted with ethyl acetate and washed with saturated NaHCO$_3$, water, and brine. The organic layer is dried over MgSO$_4$, filtered, and concentrated. The resulting residue is purified by flash chromatography on silica gel using EtOAc/hexanes to give the desired product.

7-[3S-amino-5S-methyl-piperidinyl]-3-amino-8-chloro-1-cyclopropyl-6-fluoro-1H-quinazoline-2,4-dione hydrochloride Hydrogen chloride gas is bubbled into CH$_2$Cl$_2$ for 15 minutes. The resulting solution is then cooled to 0° C. and added to a solution of {7-[3S-amino-5S-methyl-piperidin-1-yl)-8-chloro-1-cyclopropyl-6-fluoro-2,4-dioxo-1,4-dihydro-2H-quinazolin-3-yl}carbamic acid tert-butyl ester (0.067 g, 0.115 mmol). The resulting mixture is slowly warmed to room temperature. After 30 hours, the precipitate is filtered, washed with CH$_2$Cl$_2$ and hexanes, and dried under vacuum to give the desired product.

Example 21

7-[3S-amino-4R-ethyl-5S-methyl-piperidinyl]-3-amino-8-chloro-1-cyclopropyl-6-fluoro-1H-quinazoline-2,4-dione hydrochloride

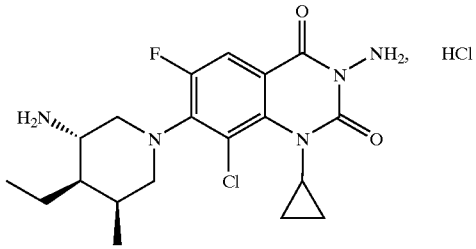

A procedure similar to Example 20 above is used, using 8-chloro-1-cyclopropyl-6,7-difluoro-2,4-dioxo-1,4-dihydro-2H-quinazolin-3-yl)carbamic acid tert-butyl ester (Precursor J) and 3(S)-tert-butoxycarbonylamino-4(R)-ethyl-5(S)-methyl-piperidine (Precursor L) as the starting materials. The procedure utilizes the same reaction conditions and molar ratio of reactants as Example 20.

Example 22

Preparation of: 7-[3S-amino-5S-methyl-piperidinyl]-3-amino-1-cyclopropyl-6-fluoro-8-methyl-1H-quinazoline-2,4-dione hydrochloride

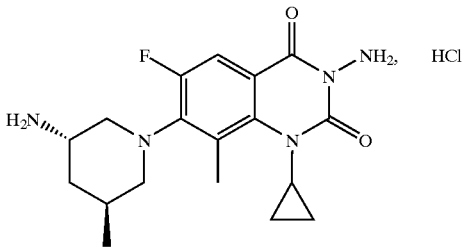

7-[3S-t-butoxycarbonylamino-5S-methyl-piperidinyl)-3-amino-1-cyclopropyl-6-fluoro-8-methyl-1H-quinazoline-2,4-dione To a solution of 3-amino-1-cyclopropyl-6,7-difluoro-8-methyl-1H-quinazoline-2,4-dione (Precursor K) (0.055 g, 0.206 mmol) and triethylamine (0.084 mL, 0.600 mmol) in acetonitrile (3 mL) is added (5(S)-methyl-piperidin-3(S)-yl)-carbamic acid tert-butyl ester (Precursor M) (0.088 g, 0.412 mmol). The solution is heated at reflux for 18 hours, the solvent is removed under reduced pressure, and the residue is triturated with water. The solid is collected by filtration and air dried to give the desired product.

7-[3S-amino-5S-methyl-piperidinyl)-3-amino-1-cyclopropyl-6-fluoro-8-methyl-1H-quinazolin-2,4-dione hydrochloride Hydrogen chloride gas is bubbled into CH$_2$Cl$_2$ for 15 minutes. The resulting solution is then cooled to 0° C. and added to a solution of 7-[3S-t-butoxycarbonylamino-5S-methyl-piperidinyl)-3-amino-1-cyclopropyl-6-fluoro-8-methyl-1H-quinazoline-2,4-dione (0.070 g, 0.145 mmol). The resulting mixture is slowly warmed to room temperature. After 30 hours, the precipitate is filtered, washed with $CH_2Cl_2$ and hexanes, and dried under vacuum to give the desired product.

Example 23

7-[3S-amino-4R-methyl-5,5-dimethyl-piperidinyl]-3-amino-1-cyclopropyl-6-fluoro-8-methyl-1H-quinazoline-2,4-dione hydrochloride

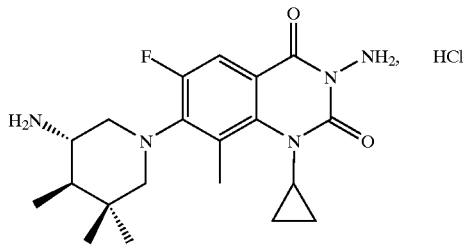

A procedure similar to Example 22 above is used, using 3-amino-1-cyclopropyl-6,7-difluoro-8-methyl-1H-quinazoline-2,4-dione (Precursor K) and 3(S)-tert-butoxycarbonylamino-4(R)-methyl-5,5-dimethyl-piperidine (Precursor R) as the starting materials. The procedure utilizes the same reaction conditions and molar ratio of reactants as Example 22.

VII. Examples

Compositions and Methods of Use

The following non-limiting examples illustrate the compositions and methods of use of the present invention.

Example 16

A tablet composition for oral administration, according to the present invention, is made comprising:

| Component | Amount |
|---|---|
| Compound of Example 1 | 150 mg |
| Lactose | 120 mg |
| Maize Starch | 70 mg |
| Talc | 4 mg |
| Magnesium Stearate | 1 mg |

Other compounds having a structure according to Formula (I) are used with substantially similar results.

Example 17

A capsule containing 200 mg of active for oral administration, according to the present invention, is made comprising:

| Component | Amount (% w/w) |
|---|---|
| Compound of Example 4 | 15% |
| Hydrous Lactose | 43% |
| Microcrystalline Cellulose | 33% |
| Crosspovidone | 3.3% |
| Magnesium Stearate | 5.7% |

Other compounds having a structure according to Formula (I) are used with substantially similar results.

Example 18

A saline-based composition for ocular administration, according to the present invention, is made comprising:

| Component | Amount (% w/w) |
|---|---|
| Compound of Example 7 | 10% |
| Saline | 90% |

Other compounds having a structure according to Formula (I) are used with substantially similar results.

Example 19

An intranasal composition for local administration, according to the present invention, is made comprising:

| Component | Composition (% w/v) |
|---|---|
| Compound of Example 10 | 0.20 |
| Benzalkonium chloride | 0.02 |
| EDTA | 0.05 |
| Glycerin | 2.0 |
| PEG 1450 | 2.0 |
| Aromatics | 0.075 |
| Purified water | q.s. |

Other compounds having a structure according to Formula (I) are used with substantially similar results.

Example 20

An inhalation aerosol composition, according to the present invention, is made comprising:

| Component | Composition (% w/v) |
|---|---|
| Compound of Example 14 | 5.0 |
| Ascorbic acid | 0.1 |
| Menthol | 0.1 |
| Sodium Saccharin | 0.2 |
| Propellant (F12, F114) | q.s. |

Other compounds having a structure according to Formula (I) are used with substantially similar results.

Example 21

A topical opthalmic composition, according to the present invention, is made comprising:

| Component | Composition (% w/v) |
|---|---|
| Compound of Example 15 | 0.10 |
| Benzalkonium chloride | 0.01 |
| EDTA | 0.05 |
| Hydroxyethylcellulose | 0.5 |
| Acetic acid | 0.20 |
| Sodium metabisulfite | 0.10 |
| Sodium chloride (0.9%) | q.s. |

Other compounds having a structure according to Formula (I) are used with substantially similar results.

Example 22

An antimicrobial composition for parenteral administration, according to this invention, is made comprising:

| Component | Amount |
|---|---|
| Compound of Example 12 | 30 mg/mL excipient |
| Excipient: | |
| 50 mm phosphate buffer pH 5 buffer with lecithin | 0.48% |
| carboxymethylcellulose | 0.53 |
| povidone | 0.50 |
| methyl paraben | 0.11 |
| propyl paraben | 0.011 |

The above ingredients are mixed, forming a suspension. Approximately 2.0 mL of the suspension is systemically administered, via intramuscular injection, to a human subject suffering from a lower respiratory tract infection, with *Streptococcus pneumoniae* present. This dosage is repeated twice daily, for approximately 14 days. After 4 days, symptoms of the disease subside, indicating that the pathogen has been substantially eradicated. Other compounds having a structure according to Formula (I) are used with substantially similar results.

Example 23

An enteric coated antimicrobial composition for oral administration, according to this invention, is made comprising the following core tablet:

| Component | Amount (mg) |
|---|---|
| Compound of Example 5 | 350.0 |
| Maltodextrine | 30.0 |
| Magnesium Stearate | 5.0 |
| Microcrystalline Cellulose | 100.0 |
| Colloidal Silicon Dioxide | 2.5 |
| Povidone | 12.5 |

The components are admixed into a bulk mixture. Compressed tablets are formed, using tabletting methods known in the art. The tablet is then coated with a suspension of methacrylic acid/methacrylic acid ester polymer in isopropanol/acetone. A human subject, having a urinary tract infection with *Escherichia coli* present, is orally administered two of the tablets, every 8 hours, for 4 days. Symptoms of the disease then subside, indicating substantial eradication of the pathogen. Other compounds having a structure according to Formula (I) are used with substantially similar results.

All documents cited in the Detailed Description of the Invention, in relevant part, incorporated herein by reference; the citation of any document is not to be construed as an admission that it is prior art with respect to the present invention.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of this invention.

What is claimed is:

1. A compound having a structure according to Formula (I)

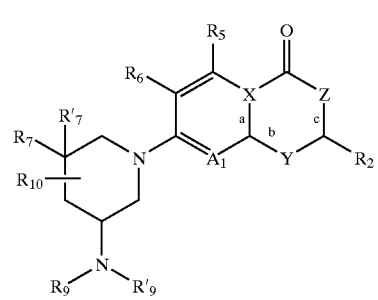

wherein:
(A)(1) $A^1$ is selected from —N— and —C($R^8$)—, where $R^8$ is selected from hydrogen, halo, $C_1$ to about $C_6$ alkyl, $C_2$ to about $C_6$ alkene or alkyne and $C_1$ to about $C_6$ alkoxy, all such alkyl, alkene, alkyne and alkoxy moieties being unsubstituted or substituted with from 1 to about 3 fluoro;
(2) a, b and c are each independently a single or double bond;
(3) (a) X is either from —C— or —N—; where (i) if X is —C—, a is a double bond and b is a single bond, and (ii) if X is —N—, a is a single bond and b is a double bond;
  (b) Y is selected from —N($R^1$)— and —C$R^°R^1$—; wherein $R^°$ is selected from hydrogen and nil, wherein $R^°$ is hydrogen when b is single bond and $R^°$ is nil when b is a double bond;
  (c) Z is selected from —C(CO$R^3$)—, —N($R^3$)— and —N(NH$R^3$)—; where (i) if Z is —C(CO$R^3$)—, c is a double bond, and (ii) if Z is either —N($R^3$)— and —N(NH$R^3$)—, c is a single bond;
  (d) provided that Y is —N($R^1$)— only if X is —C—;
  (e) provided that Y is —C($R^1$)— only if X is —N— and Z is —C(CO$R^3$)—;
(f) provided that Z is either —N($R^3$)— or —N(NH$R^3$)— only if X is —C—, Y is —N($R^1$)— and $A^1$ is —C($R^8$)—;
(4) $R^1$ is selected from $C_3$ to about $C_6$ cycloalkyl, $C_3$ to about $C_6$ heterocycloalkyl, $C_1$ to about $C_6$ alkyl, $C_2$ to about $C_6$ alkene or alkyne, $C_1$ to about $C_6$ alkyloxy, 6-membered aryl and 6-membered heteroaryl, all such alkyl, alkene, alkyne, alkoxy, cycloalkyl, aryl and heteroaryl being unsubstituted or substituted with from 1 to 3 fluoro, all such aryl and heteroaryl also being unsubstituted or substituted with one hydroxy in the 4-position;
(5) $R^2$ is selected from hydrogen, double bond oxygen, $C_1$ to about $C_6$ alkyl, $C_2$ to about $C_6$ alkene or alkyne, $C_1$ to about $C_6$ alkoxy and $C_1$ to about $C_6$ thioalkyl; provided that $R^2$ is double bond oxygen only if Z is either —N(OH)— or —N(NH$R^3$)—;
(6) $R^3$ is selected from hydrogen, hydroxy, $C_1$ to about $C_6$ alkyl, $C_2$ to about $C_6$ alkene or alkyne, $C_1$ to about $C_6$ alkoxy and $C_1$ to about $C_6$ thioalkyl;
(7) $R^5$ is selected from hydrogen, hydroxy, amino, halo, $C_1$ to about $C_6$ alkyl, $C_2$ to about $C_4$ alkene or alkyne and $C_1$ to about $C_4$ alkoxy, all such alkyl, alkene, alkyne and alkoxy moieties being unsubstituted or substituted with from 1 to 3 fluoro;
(8) $R^6$ is selected from hydroxy, aminocarbonyl, fluoro, chloro, bromo, cyano, $C_1$ to about $C_2$ alkyl and $C_2$ to about $C_4$ alkenyl or alkynyl, all such alkyl, alkenyl and alkynyl moieties being unsubstituted or substituted with from 1 to about 3 fluoro;
(9) $R^7$ and $R^{7'}$ are each independently selected from:
(a) hydrogen, $C_1$ to about $C_6$ alkyl, $C_2$ to about $C_6$ alkene or alkyne, $C_1$ to about $C_6$ alkoxy, $C_1$ to about $C_6$ alkylthio and $C_1$ to about $C_6$ heteroalkyl; provided $R^7$ and $R^{7'}$ are not both hydrogen;
(b) or $R^7$ and $R^{7'}$ join to form a $C_3$ to about $C_6$ cycloalkyl or heterocyclic ring containing the carbon atom to which they are bonded;
(c) all such alkyl, alkene, alkyne, alkoxy, alkythio, heteroalkyl, cycloalkyl and heterocyclic moieties being unsubstituted or substituted with from 1 to 3 fluoro;
(10) $R^9$ and $R^{9'}$ are each independently selected from hydrogen and $C_1$ to about $C_3$ alkyl, or $R^9$ and $R^{9'}$ join to form a $C_3$ to about $C_6$ heterocyclic ring containing the nitrogen atom to which they are bonded; and
(11) $R^{10}$ represents the moieties on the piperidine ring other than $R^7$, $R^{7'}$ and —$NR^9R^{9'}$, where each $R^{10}$ is independently selected from hydrogen, $C_1$ to about $C_6$ alkyl, $C_2$ to about $C_6$ alkene or alkyne, $C_1$ to about $C_6$ alkoxy and $C_3$–$C_6$ cycloalkyl all such alkyl, alkene, alkyne, alkoxy and cycloalkyl moieties being unsubstituted or substituted with from 1 to 3 fluoro; or
(B) if $A^1$ is —$C(R^8)$—, X is —C— and Y is —$N(R^1)$—, then $R^8$ and $R^1$ can join to form a 6-membered heterocyclic ring, where $R^2$, $R^3$, $R^5$, $R^6$, $R^7$, $R^{7'}$, $R^9$, $R^{9'}$ and $R^{10}$ are as described in (A); or
(C) if $A^1$ is —$C(R^8)$—, X is —C—, Y is —$N(R^1)$—, and Z is —$C(COR^3)$ then $R^1$ and $R^2$ can join to form a monocyclic or bicyclic heterocyclic ring, where $R^3$, $R^5$, $R^6$, $R^7$, $R^{7'}$, $R^8$, $R^9$, $R^{9'}$ and $R^{10}$ are as described in (A); or
(D) if $A^1$ is —$C(R^8)$—, X is —C—, Y is —$N(R^1)$— and Z is —$C(COR^3)$, then $R^2$ and $R^3$ can join to form a 5-membered heterocycloalkyl that is substituted with a carbonyl moiety, where $R^1$, $R^5$, $R^6$, $R^7$, $R^{7'}$, $R^8$, $R^9$, $R^{9'}$ and $R^{10}$ are as described in (A);
or an optical isomer, diastereomer or enantiomer thereof; a pharmaceutically-acceptable salt, hydrate, or biohydrolyzable ester, amide or imide thereof.

2. A compound of claim 1 wherein $R^1$ is selected from $C_3$ to about $C_6$ cycloalkyl, $C_3$ to about $C_6$ heterocycloalkyl, $C_1$ to about $C_4$ alkyl and $C_2$ to about $C_4$ alkene, all such cycloalkyl, heterocycloalkyl, alkyl and alkene, moieties being unsubstituted or substituted with from 1 to 3 fluoro.

3. A compound of claim 2, wherein $R^1$ is selected from cyclopropyl, ethyl, t-butyl, 4-hydroxyphenyl and 2,4-difluorophenyl, such cyclopropyl and ethyl moieties being unsubstituted or substituted with from 1 to about 3 fluoro.

4. A compound of claim 1, wherein Z is —$C(COR^3)$—.

5. A compound of claim 1, wherein $R^5$ is selected from hydrogen, hydroxy, chloro, bromo, amino, methyl, monofluoromethyl, difluoromethyl and trifluoromethyl.

6. A compound of claim 1, wherein each $R^7$ and $R^{7'}$ is selected from hydrogen, $C_1$ to about $C_3$ alkyl and $C_1$ to about $C_3$ alkyloxy; or $R^7$ and $R^{7'}$ join to form a $C_3$ to about $C_6$ cycloalkyl ring containing the carbon atom to which they are bonded.

7. A compound of claim 1, wherein $R^{7'}$ is hydrogen and $R^7$ is selected from methoxy, thiomethoxy, methyl and ethyl, all such methoxy, thiomethoxy, methyl and ethyl moieties being unsubstituted or substituted with from 1 to about 3 fluoro.

8. A compound of claim 7, wherein $R^7$ is methyl and the carbon atom piperidine ring member, to which $R^7$ is attached, is of the S-configuration.

9. A compound of claim 1, wherein $R^9$ and $R^{9'}$ are each independently selected from hydrogen and methyl.

10. A compound of claim 9, wherein $R^9$ and $R^{9'}$ are both hydrogen and the carbon atom piperidine ring member, to which —$NR^9R^{9'}$ is attached, is of the S-configuration.

11. A compound having a structure according to Formula (II)

(II)

wherein:
(A)(1) $A^1$ is selected from —N— and —$C(R^8)$—, where $R^8$ is selected from hydrogen, halo, $C_1$ to about $C_6$ alkyl, $C_2$ to about $C_6$ alkene or alkyne and $C_1$ to about $C_6$ alkoxy, all such alkyl, alkene, alkyne and alkoxy moieties being unsubstituted or substituted with from 1 to 3 fluoro;
(2) $R^1$ is selected from $C_3$ to about $C_6$ cycloalkyl, $C_3$ to about $C_6$ heterocycloalkyl, $C_1$ to about $C_6$ alkyl, $C_2$ to about $C_6$ alkene or alkyne, a 6-membered aryl and a 6-membered heteroaryl, all such alkyl, cycloalkyl, aryl and heteroaryl being unsubstituted or substituted with from 1 to 3 fluoro, all such aryl and heteroaryl also being unsubstituted or substituted with one hydroxy in the 4-position;
(3) $R^2$ is hydrogen;
(4) $R^3$ is hydroxy;
(5) $R^5$ is selected from hydrogen, hydroxy, amino, halo, $C_1$ to about $C_4$ alkyl, $C_2$ to about $C_4$ alkene or alkyne and $C_1$ to about $C_4$ alkoxy; all such alkyl, alkenyl, alkynyl and alkoxy moieties being unsubstituted or substituted with from 1 to about 3 fluoro;
(6) $R^6$ is selected from hydroxy, fluoro, chloro, bromo, $C_1$ to about $C_2$ alkyl; $C_2$ to about $C_4$ alkenyl or alkynyl, all such alkyl, alkenyl and alkynyl moieties being unsubstituted or substituted with from 1 to about 3 fluoro;
(7) $R^7$ and $R^{7'}$ are each independently selected from:
(a) hydrogen, $C_1$ to about $C_6$ alkyl, $C_2$ to about $C_6$ alkene or alkyne, $C_1$ to about $C_6$ alkoxy, $C_1$ to about $C_6$ alkylthio and $C_1$ to about $C_6$ heteroalkyl; provided $R^7$ and $R^{7'}$ are not both hydrogen;
(b) or $R^7$ and $R^{7'}$ join to form a $C_3$ to about $C_6$ cycloalkyl or heterocyclic ring containing the carbon atom to which they are bonded;
(c) all such alkyl, alkene, alkyne, alkoxy, alkythio, heteroalkyl, cycloalkyl and heterocyclic moieties being unsubstituted or substituted with from 1 to 3 fluoro;
(8) $R^{10}$ is selected from $C_1$ to about $C_6$ alkyl, $C_2$ to about $C_6$ alkene or alkyne and $C_1$ to about $C_6$ alkoxy, all such alkyl, alkene, alkyne and alkoxy moieties being unsubstituted or substituted with from 1 to 3 fluoro; or
(B) $R^8$ and $R^1$ join to form a 6-membered heterocyclic ring, where $R^5$, $R^6$, $R^{7'}$, $R^7$, $R^{10}$ are as described in part (A);

or an optical isomer, diastereomer or enantiomer thereof, or a pharmaceutically-acceptable salt, hydrate, or biohydrolyzable ester, amide or imide thereof.

12. A compound of claim 11, wherein $A^1$ is —C($R^8$)—.

13. A compound of claim 12, wherein $R^6$ is selected from hydroxy, fluoro, chloro, bromo and methyl.

14. A compound of claim 12, wherein $R^8$ and $R^1$ do not join to form a 6-membered heterocyclic ring.

15. A compound of claim 14, wherein $R^1$ is selected from cyclopropyl, ethyl, t-butyl, 4-hydroxyphenyl and 2,4-difluorophenyl, such cyclopropyl and ethyl moieties being unsubstituted or substituted with form 1 to about 3 fluoro.

16. A compound of claim 13, wherein $R^5$ is selected from hydrogen, hydroxy, chloro, bromo, amino, methyl, monofluoromethyl, difluoromethyl and trifluoromethyl.

17. A compound of claim 13, wherein $R^{7'}$ is hydrogen and $R^7$ is selected from methoxy, thiomethoxy, methyl and ethyl, all such methoxy, thiomethoxy, methyl and ethyl moieties being unsubstituted or substituted with from 1 to about 3 fluoro.

18. A compound of claim 17, wherein $R^7$ is methyl and the carbon atom piperidine ring member, to which $R^7$ is attached, is of the S-configuration.

19. A compound of claim 13, wherein $R^9$ and $R^{9'}$ are both hydrogen and the carbon atom piperidine ring member, to which —$NR^9R^{9'}$ is attached, is of the S-configuration.

20. A compound of claim 19, wherein the carbon atom piperidine ring member to which $R^{10}$ is attached is of the S-configuration.

21. A compound having a structure according to Formula (III)

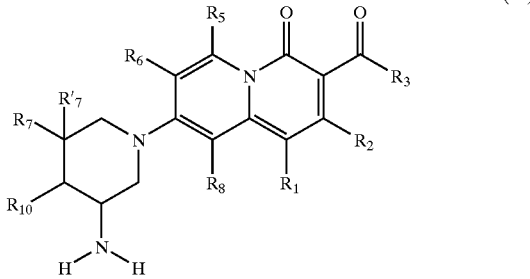

wherein:
(A)(1) $R^8$ is selected from hydrogen, halo, $C_1$ to about $C_6$ alkyl, $C_2$ to about $C_6$ alkene or alkyne and $C_1$ to about $C_6$ alkoxy, all such alkyl, alkene, alkyne and alkoxy moieties being unsubstituted or substituted with from 1 to 3 fluoro;
(2) $R^1$ is selected from $C_3$ to about $C_6$ cycloalkyl, $C_3$ to about $C_6$ heterocycloalkyl, $C_1$ to about $C_6$ alkyl, $C_1$ to about $C_6$ alkene, a 6-membered aryl and a 6-membered heteroaryl; all such alkyl, cycloalkyl, aryl and heteroaryl being unsubstituted or substituted with from 1 to 3 fluoro, all such aryl and heteroaryl also being unsubstituted or substituted with one hydroxy in the 4-position;
(3) $R^2$ is hydrogen;
(4) $R^3$ is hydroxy;
(5) $R^5$ is selected from hydrogen, hydroxy, amino, halo, $C_1$ to about $C_4$ alkyl, $C_2$ to about $C_4$ alkene or alkyne and $C_1$ to about $C_4$ alkoxy; all such alkyl, alkenyl, alkynyl and alkoxy moieties being unsubstituted or substituted with from 1 to about 3 fluoro;
(6) $R^6$ is selected from is selected from hydroxy, fluoro, chloro, bromo, $C_1$ to about $C_2$ alkyl; $C_2$ to about $C_4$ alkenyl or alkynyl, all such alkyl, alkenyl and alkynyl moieties being unsubstituted or substituted with from 1 to about 3 fluoro;
(7) $R^7$ and $R^{7'}$ are each independently selected from:
(a) hydrogen, $C_1$ to about $C_6$ alkyl, $C_2$ to about $C_6$ alkene or alkyne, $C_1$ to about $C_6$ alkoxy, $C_1$ to about $C_6$ alkylthio and $C_1$ to about $C_6$ heteroalkyl; provided $R^7$ and $R^{7'}$ are not both hydrogen;
(b) or $R^7$ and $R^{7'}$ join to form a $C_3$ to about $C_6$ cycloalkyl or heterocyclic ring containing the carbon atom to which they are bonded;
(c) all such alkyl, alkene, alkyne, alkoxy, alkythio, heteroalkyl, cycloalkyl and heterocyclic moieties being unsubstituted or substituted with from 1 to 3 fluoro;
(8) $R^{10}$ is selected from $C_1$ to about $C_6$ alkyl, $C_2$ to about $C_6$ alkene or alkyne and $C_1$ to about $C_6$ alkoxy, all such alkyl, alkene, alkyne and alkoxy moieties being unsubstituted or substituted with from 1 to 3 fluoro;

or an optical isomer, diastereomer or enantiomer thereof, or a pharmaceutically-acceptable salt, hydrate, or biohydrolyzable ester, amide or imide thereof.

22. A compound of claim 21 wherein $R^6$ is selected from hydroxy, fluoro, bromo, chloro and methyl.

23. A compound of claim 21 wherein $R^1$ is selected from cyclopropyl, ethyl, t-butyl, 4-hydroxyphenyl and 2,4-difluorophenyl, such cyclopropyl and ethyl moieties being unsubstituted or substituted with form 1 to about 3 fluoro.

24. A compound of claim 21 wherein $R^5$ is selected from hydrogen, hydroxy, chloro, bromo, amino, methyl, monofluoromethyl, difluoromethyl and trifluoromethyl.

25. A compound of claim 22 wherein $R^{7'}$ is hydrogen and $R^7$ is selected from methoxy, thiomethoxy, methyl and ethyl, all such methoxy, thiomethoxy, methyl and ethyl moieties being unsubstituted or substituted with from 1 to about 3 fluoro.

26. A compound of claim 25 wherein $R^7$ is methyl and the carbon atom piperidine ring member, to which $R^7$ is attached, is of the S-configuration.

27. A compound of claim 21, wherein $R^9$ and $R^{9'}$ are both hydrogen and the carbon atom piperidine ring member, to which —$NR^9R^{9'}$ is attached, is of the S-configuration.

28. A compound of claim 27, wherein the carbon atom piperidine ring member to which $R^{10}$ is attached is of the S-configuration.

29. A compound having a structure according to Formula (IV)

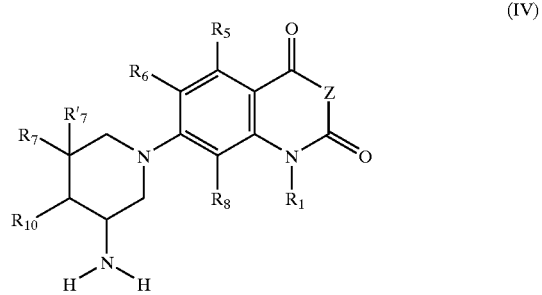

wherein:
(A)(1) $R^8$ is selected from hydrogen, halo, $C_1$ to about $C_6$ alkyl, $C_2$ to about $C_6$ alkene or alkyne and $C_1$ to about $C_6$ alkoxy, all such alkyl, alkene, alkyne and alkoxy moieties being unsubstituted or substituted with from 1 to 3 fluoro
(2) $R^1$ is selected from $C_3$ to about $C_6$ cycloalkyl, $C_3$ to about $C_6$ heterocycloalkyl, $C_1$ to about $C_6$ alkyl, $C_1$ to about C₆ alkene, a 6-membered aryl and a 6-membered heteroaryl, all such alkyl, cycloalkyl, aryl and heteroaryl being unsubstituted or substituted with from 1 to 3 fluoro, all such aryl and heteroaryl also being unsubstituted or substituted with one hydroxy in the 4-position;
(3) Z is either —N($R^3$)— or —N(NH$R^3$)—;
(4) $R^3$ is selected from hydrogen, hydroxy and $C_1$ to about $C_6$ alkyl;
(5) $R^5$ is selected from hydrogen, hydroxy, amino, halo, $C_1$ to about $C_4$ alkyl, $C_2$ to about $C_4$ alkene or alkyne and $C_1$ to about $C_4$ alkoxy; all such alkyl, alkenyl, alkynyl and alkoxy moieties being unsubstituted or substituted with from 1 to about 3 fluoro;
(6) $R^6$ is selected from hydroxy, fluoro, chloro, bromo, $C_1$ to about $C_2$ alkyl; $C_2$ to about $C_4$ alkenyl or alkynyl, all such alkyl, alkenyl and alkynyl moieties being unsubstituted or substituted with from 1 to about 3 fluoro;
(7) $R^7$ and $R^{7'}$ are each independently selected from:
(a) hydrogen, $C_1$ to about $C_6$ alkyl, $C_2$ to about $C_6$ alkene or alkyne, $C_1$ to about $C_6$ alkoxy, $C_1$ to about $C_6$ alkylthio and $C_1$ to about $C_6$ heteroalkyl; provided $R^7$ and $R^{7'}$ are not both hydrogen;
(b) or $R^7$ and $R^{7'}$ join to form a $C_3$ to about $C_6$ cycloalkyl or heterocyclic ring containing the carbon atom to which they are bonded;
(c) all such alkyl, alkene, alkyne, alkoxy, alkythio, heteroalkyl, cycloalkyl and heterocyclic moieties being unsubstituted or substituted with from 1 to 3 fluoro;
(8) $R^{10}$ is selected from $C_1$ to about $C_6$ alkyl, $C_2$ to about $C_6$ alkene or alkyne and $C_1$ to about $C_6$ alkoxy, all such alkyl, alkene, alkyne and alkoxy moieties being unsubstituted or substituted with from 1 to 3 fluoro;

or an optical isomer, diastereomer or enantiomer thereof, or a pharmaceutically-acceptable salt, hydrate, or biohydrolyzable ester, amide or imide thereof.

30. A compound of claim 29 wherein $R^6$ is selected from hydroxy, fluoro, bromo, chloro and methyl.

31. A compound of claim 29 wherein $R^1$ is selected from cyclopropyl, ethyl, t-butyl, 4-hydroxyphenyl and 2,4-difluorophenyl, such cyclopropyl and ethyl moieties being unsubstituted or substituted with form 1 to about 3 fluoro.

32. A compound of claim 29 wherein $R^5$ is selected from hydrogen, hydroxy, chloro, bromo, amino, methyl, monofluoromethyl, difluoromethyl and trifluoromethyl.

33. A compound of claim 30 wherein $R^{7'}$ is hydrogen and $R^7$ is selected from methoxy, thiomethoxy, methyl and ethyl, all such methoxy, thiomethoxy, methyl and ethyl moieties being unsubstituted or substituted with from 1 to about 3 fluoro.

34. A compound of claim 33 wherein $R^7$ is methyl and the carbon atom piperidine ring member, to which $R^7$ is attached, is of the S-configuration.

35. A compound of claim 30, wherein $R^9$ and $R^{9'}$ are both hydrogen and the carbon atom piperidine ring member, to which —N$R^9R^{9'}$ is attached, is of the S-configuration.

36. A compound of claim 35, wherein the carbon atom piperidine ring member to which $R^{10}$ is attached is of the S-configuration.

37. A compound of claim 1, selected from the group consisting of:

7-[3S-amino-5S-methyl-piperidinyl]-1-cyclopropyl-1,4-dihydro-6-fluoro-8-methoxy-4-oxo-3-quinolinecarboxylic acid;

7-[3S-amino-5R-methyl-piperidinyl]-1-cyclopropyl-1,4-dihydro-6-fluoro-8-methoxy-4-oxo-3-quinolinecarboxylic acid;

7-[3S-amino-5S-ethyl-piperidinyl]-1-cyclopropyl-1,4-dihydro-6-fluoro-8-methoxy-4-oxo-3-quinolinecarboxylic acid;

7-[3S-amino-5R-ethyl-piperidinyl]-1-cyclopropyl-1,4-dihydro-6-fluoro-8-methoxy-4-oxo-3-quinolinecarboxylic acid;

7-[3S-amino-5S-methoxy-piperidinyl]-1-cyclopropyl-1,4-dihydro-6-fluoro-8-methoxy-4-oxo-3-quinolinecarboxylic acid;

7-[3S-amino-5R-methoxy-piperidinyl]-1-cyclopropyl-1,4-dihydro-6-fluoro-8-methoxy-4-oxo-3-quinolinecarboxylic acid;

7-[3S-amino-5,5dimethyl-piperidinyl]-1-cyclopropyl-1,4-dihydro-6-fluoro-8-methoxy-4-oxo-3-quinolinecarboxylic acid;

7-[3S-amino-5,5diethyl-piperidinyl]-1-cyclopropyl-1,4-dihydro-6-fluoro-8-methoxy-4-oxo-3-quinolinecarboxylic acid;

7-[3S-amino-4S-methyl-5R-methyl-piperidinyl]-1-cyclopropyl-1,4-dihydro-6-fluoro-8-methoxy-4-oxo-3-quinolinecarboxylic acid;

7-[3S-amino-4S-ethyl-5R-methyl-piperidinyl]-1-cyclopropyl-1,4-dihydro-6-fluoro-8-methoxy-4-oxo-3-quinolinecarboxylic acid;

7-[3S-amino-4S-isopropyl-1R-methyl-piperidinyl]-1-cyclopropyl-1,4-dihydro-6-fluoro-8-methoxy-4-oxo-3-quinolinecarboxylic acid;

7-[7-amino-5-azaspiro[2.5]-octanyl]-1-cyclopropyl-1,4-dihydro-6-fluoro-8-methoxy-4-oxo-3-quinolinecarboxylic acid;

7-[7-amino-8S-methyl-5-azaspiro[2.5]-octanyl]-1-cyclopropyl-1,4-dihydro-6-fluoro-8-methoxy-4-oxo-3-quinolinecarboxylic acid;

7-[7-amino-8S-ethyl-5-azaspiro[2.5]-octanyl]-1-cyclopropyl-1,4-dihydro-6-fluoro-8-methoxy-4-oxo-3-quinolinecarboxylic acid;

7-[8-amino-6-azaspiro[3.5]-nonanyl]-1-cyclopropyl-1,4-dihydro-6-fluoro-8-methoxy-4-oxo-3-quinolinecarboxylic acid;

7-[8-amino-9S-methyl-6-azaspiro[3.5]-nonanyl]-1-cyclopropyl-1,4-dihydro-6-fluoro-8-methoxy-4-oxo-3-quinolinecarboxylic acid;

7-[3S-amino-5S-methyl-piperidinyl]-1-cyclopropyl-1,4-dihydro-6-fluoro-8-methyl-4-oxo-3-quinolinecarboxylic acid;

7-[3S-amino-5R-methyl-piperidinyl]-1-cyclopropyl-1,4-dihydro-6-fluoro-8-methyl-4-oxo-3-quinolinecarboxylic acid;

7-[3S-amino-5S-ethyl-piperidinyl]-1-cyclopropyl-1,4-dihydro-6-fluoro-8-methyl-4-oxo-3-quinolinecarboxylic acid;

7-[3S-amino-5R-ethyl-piperidinyl]-1-cyclopropyl-1,4-dihydro-6-fluoro-8-methyl-4-oxo-3-quinolinecarboxylic acid;

7-[3S-amino-5S-methoxy-piperidinyl]-1-cyclopropyl-1,4-dihydro-6-fluoro-8-methyl-4-oxo-3-quinolinecarboxylic acid;

7-[3S-amino-5R-methoxy-piperidinyl]-1-cyclopropyl-1,4-dihydro-6-fluoro-8-methyl-4-oxo-3-quinolinecarboxylic acid;

7-[3S-amino-5,5dimethyl-piperidinyl]-1-cyclopropyl-1,4-dihydro-6-fluoro-8-methyl-4-oxo-3-

7-[3S-amino-5,5diethyl-piperidinyl]-1-cyclopropyl-1,4-dihydro-6-fluoro-8-methyl-4-oxo-3-quinolinecarboxylic acid;

7-[3S-amino-4S-methyl-5R-methyl-piperidinyl]-1-cyclopropyl-1,4-dihydro-6-fluoro-8-methyl-4-oxo-3-quinolinecarboxylic acid;

7-[3S-amino-4S-ethyl-5R-methyl-piperidinyl]-1-cyclopropyl-1,4-dihydro-6-fluoro-8-methyl-4-oxo-3-quinolinecarboxylic acid;

7-[3S-amino-4S-isopropyl-5R-methyl-piperidinyl]-1-cyclopropyl-1,4-dihydro-6-fluoro-8-methyl-4-oxo-3-quinolinecarboxylic acid;

7-[7-amino-5-azaspiro[2.5]-octanyl]-1-cyclopropyl-1,4-dihydro-6-fluoro-8-methyl-4-oxo-3-quinolinecarboxylic acid;

7-[7-amino-8S-methyl-5-azaspiro[2.5]-octanyl]-1-cyclopropyl-1,4-dihydro-6-fluoro-8-methyl-4-oxo-3-quinolinecarboxylic acid;

7-[7-amino-8S-ethyl-5-azaspiro[2.5]-octanyl]-1-cyclopropyl-1,4-dihydro-6-fluoro-8-methyl-4-oxo-3-quinolinecarboxylic acid;

7-[8-amino-6-azaspiro[3.5]-nonanyl]-1-cyclopropyl-1,4-dihydro-6-fluoro-8-methyl-4-oxo-3-quinolinecarboxylic acid;

7-[8-amino-9S-methyl-6-azaspiro[3.5]-nonanyl]-1-cyclopropyl-1,4-dihydro-6-fluoro-8-methyl-4-oxo-3-quinolinecarboxylic acid;

7-[3S-amino-5S-methyl-piperidinyl]-1-cyclopropyl-1,4-dihydro-6-hydroxy-8-chloro-4-oxo-3-quinolinecarboxylic acid;

7-[3S-amino-5R-methyl-piperidinyl]-1-cyclopropyl-1,4-dihydro-6-hydroxy-8-chloro-4-oxo-3-quinolinecarboxylic acid;

7-[3S-amino-5S-ethyl-piperidinyl]-1-cyclopropyl-1,4-dihydro-6-hydroxy-8-chloro-4-oxo-3-quinolinecarboxylic acid;

7-[3S-amino-5R-ethyl-piperidinyl]-1-cyclopropyl-1,4-dihydro-6-hydroxy-8-chloro-4-oxo-3-quinolinecarboxylic acid;

7-[3S-amino-5S-methoxy-piperidinyl]-1-cyclopropyl-1,4-dihydro-6-hydroxy-8-chloro-4-oxo-3-quinolinecarboxylic acid;

7-[3S-amino-5R-methoxy-piperidinyl]-1-cyclopropyl-1,4-dihydro-6-hydroxy-8-chloro-4-oxo-3-quinolinecarboxylic acid;

7-[3S-amino-5,5dimethyl-piperidinyl]-1-cyclopropyl-1,4-dihydro-6-hydroxy-8-chloro-4-oxo-3-quinolinecarboxylic acid;

7-[3S-amino-5,5diethyl-piperidinyl]-1-cyclopropyl-1,4-dihydro-6-hydroxy-8-chloro-4-oxo-3-quinolinecarboxylic acid;

7-[3S-amino-4S-methyl-5R-methyl-piperidinyl]-1-cyclopropyl-1,4-dihydro-6-hydroxy-8-chloro-4-oxo-3-quinolinecarboxylic acid;

7-[3S-amino-4S-ethyl-5R-methyl-piperidinyl]-1-cyclopropyl-1,4-dihydro-6-hydroxy-8-chloro-4-oxo-3-quinolinecarboxylic acid;

7-[3S-amino-4S-isopropyl-5R-methyl-piperidinyl]-1-cyclopropyl-1,4-dihydro-6-hydroxy-8-chloro-4-oxo-3-quinolinecarboxylic acid;

7-[7-amino-5-azaspiro[2.5]-octanyl]-1-cyclopropyl-1,4-dihydro-6-hydroxy-8-chloro-4-oxo-3-quinolinecarboxylic acid;

7-[7-amino-8S-methyl-5-azaspiro[2.5]-octanyl]-1-cyclopropyl-1,4-dihydro-6-hydroxy-8-chloro-4-oxo-3-quinolinecarboxylic acid;

7-[7-amino-8S-ethyl-5-azaspiro[2.5]-octanyl]-1-cyclopropyl-1,4-dihydro-6-hydroxy-8-chloro-4-oxo-3-quinolinecarboxylic acid;

7-[8-amino-6-azaspiro[3.5]-nonanyl]-1-cyclopropyl-1,4-dihydro-6-hydroxy-8-chloro-4-oxo-3-quinolinecarboxylic acid;

7-[8-amino-9S-methyl-6-azaspiro[3.5]-nonanyl]-1-cyclopropyl-1,4-dihydro-6-hydroxy-8-chloro-4-oxo-3-quinolinecarboxylic acid;

8-[3S-amino-5S-methyl-piperidinyl]-1-cyclopropyl-7-fluoro-9-methyl-4-oxo-4H-quinolizine-3-carboxylic acid;

8-[3S-amino-5R-methyl-piperidinyl]-1-cyclopropyl-7-fluoro-9-methyl-4-oxo-4H-quinolizine-3-carboxylic acid;

8-[3S-amino-5S-ethyl-piperidinyl]-1-cyclopropyl-7-fluoro-9-methyl-4-oxo-4H-quinolizine-3-carboxylic acid;

8-[3S-amino-5R-ethyl-piperidinyl]-1-cyclopropyl-7-fluoro-9-methyl-4-oxo-4H-quinolizine-3-carboxylic acid;

8-[3S-amino-5S-methoxy-piperidinyl]1-cyclopropyl-7-fluoro-9-methyl-4-oxo-4H-quinolizine-3-carboxylic acid;

8-[3S-amino-5R-methoxy-piperidinyl]-1-cyclopropyl-7-fluoro-9-methyl-4-oxo-4H-quinolizine-3-carboxylic acid;

8-[3S-amino-5,5dimethyl-piperidinyl]-1-cyclopropyl-7-fluoro-9-methyl-4-oxo-4H-quinolizine-3-carboxylic acid;

8-[3S-amino-5,5diethyl-piperidinyl]-1-cyclopropyl-7-fluoro-9-methyl-4-oxo-4H-quinolizine-3-carboxylic acid;

8-[3S-amino-4S-methyl-5R-methyl-piperidinyl]-1-cyclopropyl-7-fluoro-9-methyl-4-oxo-4H-quinolizine-3-carboxylic acid;

8-[3S-amino-4S-ethyl-5R-methyl-piperidinyl]-1-cyclopropyl-7-fluoro-9-methyl-4-oxo-4H-quinolizine-3-carboxylic acid;

8-[3S-amino-4S-isopropyl-5R-methyl-piperidinyl]-1-cyclopropyl-7-fluoro-9-methyl-4-oxo-4H-quinolizine-3-carboxylic acid;

8-[7-amino-5-azaspiro[2.5]-octanyl]-1-cyclopropyl-7-fluoro-9-methyl-4-oxo-4H-quinolizine-3-carboxylic acid;

8-[7-amino-8S-methyl-5-azaspiro[2.5]-octanyl]-1-cyclopropyl-7-fluoro-9-methyl-4-oxo-4H-quinolizine-3-carboxylic acid;

8-[7-amino-8S-ethyl-5-azaspiro[2.5]-octanyl]-1-cyclopropyl-7-fluoro-9-methyl-4-oxo-4H-quinolizine-3-carboxylic acid;

8-[8-amino-6-azaspiro[3.5]-nonanyl]-1-cyclopropyl-7-fluoro-9-methyl-4-oxo-4H-quinolizine-3-carboxylic acid;

8-[8-amino-9S-methyl-6-azaspiro[3.5]-nonanyl]-1-cyclopropyl-7-fluoro-9-methyl-4-oxo-4H-quinolizine-3-carboxylic acid;

7-[3S-amino-5S-methyl-piperidinyl]-3-amino-1-cyclopropyl-6-fluoro-8-methyl-1H-quinazoline-2,4-dione;

7-[3S-amino-5R-methyl-piperidinyl]-3-amino-1-cyclopropyl-6-fluoro-8-methyl-1H-quinazoline-2,4-dione;

7-[3S-amino-5S-ethyl-piperidinyl]-3-amino-1-cyclopropyl-6-fluoro-8-methyl-1H-quinazoline-2,4-dione;

7-[3S-amino-5R-ethyl-piperidinyl]-3-amino-1-cyclopropyl-6-fluoro-8-methyl-1H-quinazoline-2,4-dione;

7-[3S-amino-5S-methoxy-piperidinyl]-3-amino-1-cyclopropyl-6-fluoro-8-methyl-1H-quinazoline-2,4-dione;

7-[3S-amino-5R-methoxy-piperidinyl]-3-amino-1-cyclopropyl-6-fluoro-8-methyl-1H-quinazoline-2,4-dione;

7-[3S-amino-5,5dimethyl-piperidinyl]-3-amino-1-cyclopropyl-6-fluoro-8-methyl-1H-quinazoline-2,4-dione;

7-[3S-amino-5,5diethyl-piperidinyl]-3-amino-1-cyclopropyl-6-fluoro-8-methyl-1H-quinazoline-2,4-dione;

7-[3S-amino-4S-methyl-5R-methyl-piperidinyl]-3-amino-1-cyclopropyl-6-fluoro-8-methyl-1H-quinazoline-2,4-dione;

7-[3S-amino-4S-ethyl-5R-methyl-piperidinyl]-3-amino-1-cyclopropyl-6-fluoro-8-methyl-1H-quinazoline-2,4-dione;

7-[3S-amino-4S-isopropyl-5R-methyl-piperidinyl]-3-amino-1-cyclopropyl-6-fluoro-8-methyl-1H-quinazoline-2,4-dione;

7-[7-amino-5-azaspiro[2.5]-octanyl]-3-amino-1-cyclopropyl-6-fluoro-8-methyl-1H-quinazoline-2,4-dione;

7-[7-amino-8S-methyl-5-azaspiro[2.5]-octanyl]-3-amino-1-cyclopropyl-6-fluoro-8-methyl-1H-quinazoline-2,4-dione 7-[7-amino-8S-ethyl-5-azaspiro[2.5]-octanyl]-3-amino-1-cyclopropyl-6-fluoro-8-methyl-1H-quinazoline-2,4-dione;

7-[8-amino-6-azaspiro[3.5]-nonanyl]-3-amino-1-cyclopropyl-6-fluoro-8-methyl-1H-quinazoline-2,4-dione;

7-[8-amino-9S-methyl-6-azaspiro[3.5]-nonanyl]-3-amino-1-cyclopropyl-6-fluoro-8-methyl-1H-quinazoline-2,4-dione.

38. A pharmaceutical composition comprising:

(a) a safe and effective amount of a compound of claim 1; and (b) a pharmaceutically-acceptable excipient.

39. A method for treating microbial infection comprising administering to a host in need of such a treatment a safe and antimicrobially effective amount of a compound of claim 1.

\* \* \* \* \*

UNITED STATES PATENT AND TRADEMARK OFFICE
CERTIFICATE OF CORRECTION

PATENT NO. : 6,900,224 B2 Page 1 of 2
APPLICATION NO. : 10/462554
DATED : May 31, 2005
INVENTOR(S) : Benoit Ledoussal et al.

It is certified that error appears in the above-identified patent and that said Letters Patent is hereby corrected as shown below:

Column 24
Line 22, please delete the Formula (C)

"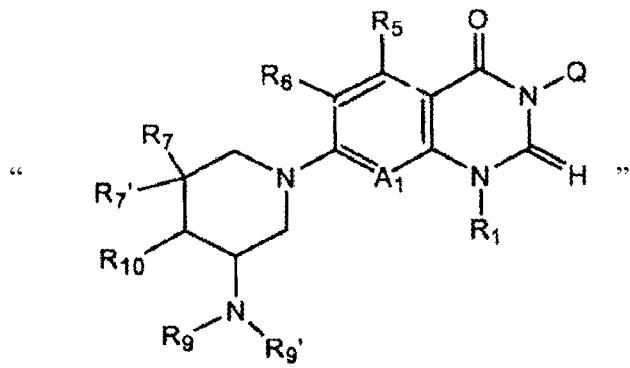"

and insert – Table III contains compounds of Formula (C).

--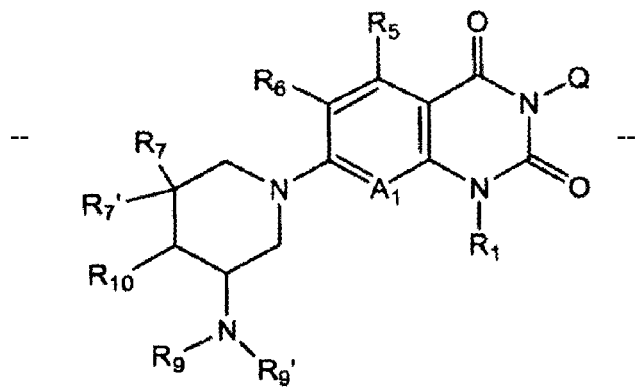--

UNITED STATES PATENT AND TRADEMARK OFFICE
CERTIFICATE OF CORRECTION

PATENT NO.       : 6,900,224 B2
APPLICATION NO.  : 10/462554
DATED            : May 31, 2005
INVENTOR(S)      : Benoit Ledoussal et al.

It is certified that error appears in the above-identified patent and that said Letters Patent is hereby corrected as shown below:

<u>Column 110</u>
Line 27, please delete "7-[3S-amino-4S-isopropyl-1R-methyl-piperidinyl]-" and insert --7-[3S-amino-4S-isopropyl-5R-methyl-piperidinyl]- --.

<u>Column 112</u>
Line 27, please delete "8-[3S-amino-5S-methoxy-piperidinyl]1-cyclopropyl-7-" and insert -- 8-[3S-amino-5S-methoxy-piperidinyl]-1-cyclopropyl-7- --.

Signed and Sealed this

Twenty-sixth Day of August, 2008

JON W. DUDAS
*Director of the United States Patent and Trademark Office*